(12) United States Patent
Nordsiek et al.

(10) Patent No.: US 10,238,634 B2
(45) Date of Patent: *Mar. 26, 2019

(54) AQUEOUS-BASED METRONIDAZOLE GEL FORMULATIONS

(71) Applicant: CHEMO RESEARCH, S.L., Madrid OT (ES)

(72) Inventors: Michael T. Nordsiek, Wayne, PA (US); Kodumudi S. Balaji, Landsdale, PA (US)

(73) Assignee: CHEMO RESEARCH, S.L., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,737

(22) Filed: Oct. 23, 2015

(65) Prior Publication Data

US 2016/0106714 A1    Apr. 21, 2016

Related U.S. Application Data

(63) Continuation of application No. 13/593,386, filed on Aug. 23, 2012, now Pat. No. 9,198,858, which is a continuation of application No. 13/536,960, filed on Jun. 28, 2012, now Pat. No. 8,946,276.

(60) Provisional application No. 61/508,058, filed on Jul. 14, 2011, provisional application No. 61/502,285, filed on Jun. 28, 2011.

(51) Int. Cl.
| | |
|---|---|
| *A61K 31/4168* | (2006.01) |
| *A61K 31/4164* | (2006.01) |
| *A61K 9/00* | (2006.01) |
| *A61K 9/06* | (2006.01) |
| *A61K 47/10* | (2017.01) |
| *A61K 47/14* | (2017.01) |
| *A61K 47/32* | (2006.01) |

(52) U.S. Cl.
CPC ........ *A61K 31/4168* (2013.01); *A61K 9/0034* (2013.01); *A61K 9/06* (2013.01); *A61K 31/4164* (2013.01); *A61K 47/10* (2013.01); *A61K 47/14* (2013.01); *A61K 47/32* (2013.01)

(58) Field of Classification Search
CPC ............ A61K 31/4164; A61K 31/4168; A61K 47/10; A61K 47/14; A61K 47/32; A61K 9/0034; A61K 9/06

See application file for complete search history.

(56) References Cited

U.S. PATENT DOCUMENTS

| | | | |
|---|---|---|---|
| 4,837,378 A | 6/1989 | Borgman | |
| 5,536,743 A | 7/1996 | Borgman et al. | |
| 5,840,744 A | 11/1998 | Borgman | |
| 6,126,959 A | 10/2000 | Levine et al. | |
| 6,348,203 B1 | 2/2002 | Goodman et al. | |
| 6,423,307 B2 | 7/2002 | Saettone et al. | |
| 6,468,989 B1 | 10/2002 | Chang et al. | |
| 6,881,726 B2 | 4/2005 | Chang et al. | |
| 7,348,317 B2 | 3/2008 | Chang et al. | |
| 7,368,122 B1 | 5/2008 | Dow et al. | |
| 7,456,207 B2 | 11/2008 | Bentley et al. | |
| 7,704,518 B2 | 4/2010 | Tamarkin et al. | |
| 7,893,097 B2 | 2/2011 | Yang et al. | |
| 7,981,916 B2 | 7/2011 | Mallard et al. | |
| 2002/0012674 A1 | 1/2002 | Saettone et al. | |
| 2003/0119783 A1 | 1/2003 | Chang et al. | |
| 2005/0080038 A1 | 4/2005 | Bentley et al. | |
| 2005/0186142 A1 | 8/2005 | Tamarkin et al. | |
| 2006/0093675 A1 | 5/2006 | Ebmeier et al. | |
| 2006/0269485 A1 | 11/2006 | Friedman et al. | |
| 2007/0105788 A1 | 5/2007 | Mraz-Gernhard et al. | |
| 2007/0224226 A1 | 9/2007 | Levinson et al. | |
| 2007/0231358 A1 | 10/2007 | Ebmeier et al. | |
| 2008/0154030 A1 | 6/2008 | Chang et al. | |
| 2008/0287513 A1 | 11/2008 | Zhang | |
| 2008/0287514 A1 | 11/2008 | Zhang | |
| 2008/0287515 A1 | 11/2008 | Zhang | |
| 2008/0312304 A1 | 12/2008 | Zhang | |
| 2009/0030060 A1 | 1/2009 | Ebmeier et al. | |
| 2009/0197896 A1* | 8/2009 | Yang ................... | A61K 9/0014 514/254.07 |
| 2010/0048645 A1 | 2/2010 | Mallard et al. | |
| 2010/0048659 A1 | 2/2010 | Chang et al. | |
| 2010/0105750 A1 | 4/2010 | Aksamit et al. | |
| 2011/0082179 A1 | 4/2011 | Yang et al. | |
| 2011/0217357 A1 | 9/2011 | Mallard et al. | |
| 2011/0237637 A1 | 9/2011 | Mallard et al. | |

(Continued)

FOREIGN PATENT DOCUMENTS

| | | |
|---|---|---|
| EP | 0537784 | 3/1995 |
| FR | 2899475 | 10/2007 |
| WO | 1988006888 | 9/1988 |

(Continued)

OTHER PUBLICATIONS

Malvern Instruments, Bohlin CVO, Rheological Instruments Backed with Rheological Experience, 2010, pp. 1-4 (2010).

Tirnaksiz, F., et al., Preparation and Evaluation of Topical Microemulsion System Containing Metronidazole for Remission in Rosacea, Chemical & Pharmaceutical Bulletin, 60(5):583-592 (2012).

Centers for Disease Control and Prevention, 1993 Sexually Transmitted Diseases Treatment Guidelines, Morbidity and Mortality Weekly Report, 42/RR-14: 1-102 (1993).

Centers for Disease Control and Prevention, 1989 Sexually Transmitted Diseases Treatment Guidelines, Morbidity and Mortality Weekly Report, 1-32 (1989).

(Continued)

Primary Examiner — Sarah Pihonak
(74) Attorney, Agent, or Firm — Florek & Endres PLLC

(57) ABSTRACT

The present disclosure provides mucoadhesive aqueous-based gel formulations of metronidazole useful for a variety of purposes, including intravaginal application as a therapeutic approach towards the treatment of individuals suffering from and/or diagnosed with bacterial vaginosis.

9 Claims, 16 Drawing Sheets

(56) References Cited

U.S. PATENT DOCUMENTS

Figure 1:
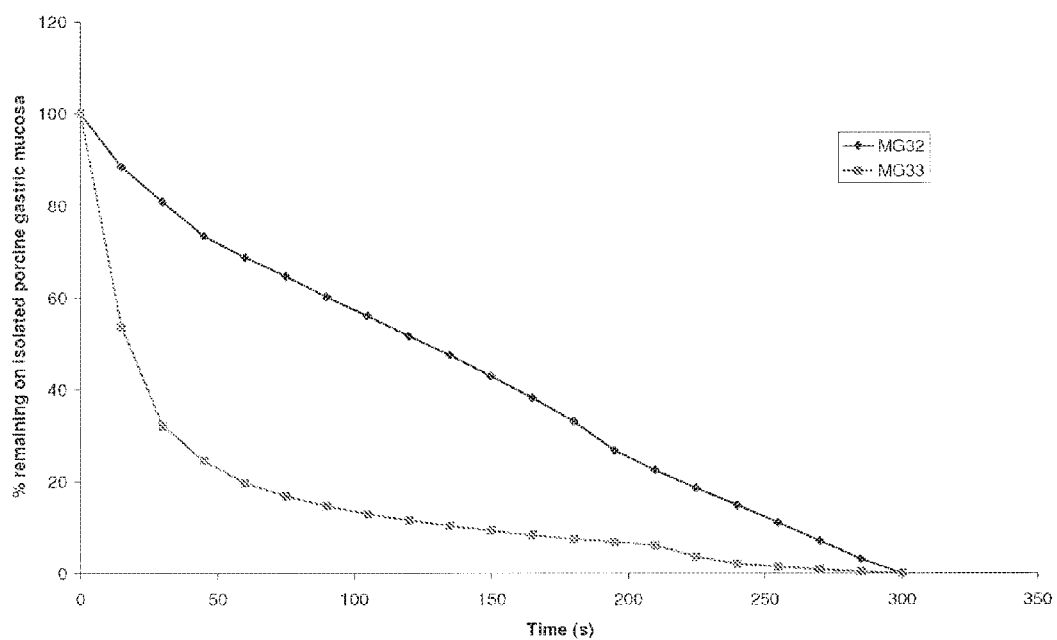

2011/0237638 A1      9/2011    Mallard et al.

FOREIGN PATENT DOCUMENTS

| WO | 1990014832 | 12/1990 |
| --- | --- | --- |
| WO | 1998014768 | 4/1998 |
| WO | 1998027960 | 7/1998 |
| WO | 2002006349 | 1/2002 |
| WO | 2003057135 | 7/2003 |
| WO | 2006050303 | 5/2006 |
| WO | 2006089804 | 8/2006 |
| WO | 2007039825 | 4/2007 |
| WO | 2007072216 | 6/2007 |
| WO | 2007099396 | 9/2007 |
| WO | 2008038140 | 4/2008 |
| WO | 2009097143 | 8/2009 |
| WO | 2010047831 | 4/2010 |
| WO | 2011109469 | 9/2011 |

OTHER PUBLICATIONS

Centers for Disease Control and Prevention, 1985 Sexually Transmitted Diseases Treatment Guidelines, Morbidity and Mortality Weekly Report, 34/4S 75S-108S (1985).

Centers for Disease Control and Prevention, 1998 Sexually Transmitted Diseases Treatment Guidelines, Morbidity and Mortality Weekly Report, 47/RR-1: 1-118 (1998).

Centers for Disease Control and Prevention, Sexually Transmitted Diseases Treatment Guidelines, Morbidity and Mortality Weekly Report, 59/RR-12: 1-110 (2010).

Centers for Disease Control and Prevention, Sexually Transmitted Diseases Treatment Guidelines, Morbidity and Mortality Weekly Report, 55/RR-11:1-94 (2006).

Centers for Disease Control and Prevention, Sexually Transmitted Diseases Treatment Guidelines, Morbidity and Mortality Weekly Report, 51/RR-6: 1-80 (2002).

Joesoeff, M.R., et al., Bacterial Vaginosis: Review of Treatment Options and Potential Clinical Indication for Therapy, CID 20 (Suppl. 1) S27-S79 (1995).

Label of Flagyl (metronidazole), 1-9 (1999).

Menard, J.P., Antibacterial Treatment of Bacterial Vaginosis: Current and Emergent Therapies, Int. J. Women's Health 3: 295-305, Aug. 23, 2011.

The International Search Report for PCT/US2012/044738, dated Sep. 7, 2012.

Abass, et al., Metronidazole Bioadhesive Vaginal Suppositories: Formulation, in vitro and in vivo Evaluation, Int. J. Pharmcy Pharm. Sci. 4(1): 344-353, Jan. 18, 2012.

Acarturk, Mucoadhesive Vaginal Drug Delivery Systems, Recent Pat. Drug Deliv. Formulation 3(3): 193-205, Dec. 10, 2009.

Alam, et al., Development and Evaluation of Acid-buffering Bioadhesive Vaginal Tablet for Mixed Vaginal Infections, AAPS PharmSciTech 8(4) Article 109:E1-E8, 2007.

Aronson, et al., Evaluation of Topucal Metronidazole Gel in Acne Rosacea, Ann Pharmacother 21(4): 346-351, Apr. 1, 1987.

Bhowmik, et al., Formulation Development and Characterization of Metronidazole Microencapsulated Bioadhesive Vaginal Gel. Int. J. Pharmcy Pharm. Sci. 1(1): 240-257, 2009.

Boeck, et al., Perioral Dermatisis in Children—Clinical Presentation, Pathogenisis-related Factors and Response to Topical Metronidazole, Dermatology 195(3): 235-38, 1997.

Bouckaert, et al., Preliminary Efficacy Study of a Bioadhesive Vaginal Metronidazole Tablet in the Treatment of Bacterial Vaginosis, J. Pharm. Pharmacol. 47:970-71, 1995.

Brandt, et al., Intravaginally Applied Metronidazole is as Effective as Orally Applied in the Treatment of Bacterial Vaginosis, But Exhibits Significantly Less Side Effects, European Journal of Obstetrics & Gynecology and Reproductive Biology 141(2): 158-162, Dec. 2008.

Bukusi, et al., Topical Penile Microbicide Used by Men to Prevent Recurrent Bacterial Vaginosis in Sex Partners: A Randomized Clinical Trial, Sex. Transm. Dis. 38(6): 483-89, Jun. 1, 2011.

Conde, et al., Managing Rosacea: A Review of the Use of Metronidazole Alone and in Combination with Oral Antibiotics, J. Drugs Dermatol 6(5): 495-98, May 2007.

Dahl, et al., Once-daily Topical Metronidazole Cream Formulations in the Treatment of the Papules and Pustules of Rosacea, J. Am. Acad. Dermatol 45(5): 732-30, Nov. 2001.

Das Neves, et al., Gels as Vaginal Drug Delivery Systems, Int. J. Pharm. 318:1-14, Mar. 17, 2006.

Del Rosso, Cutaneous Tolerability of Metronidazole Topical Gel 0.75% for Rosacea, Cosmet. Dermatol 18 (8):559-62, 2005.

Dias, et al., Sustained Release System from Vaginal Bioadhesive Matrix Tablets Containing Metronidazole, Rev. Cienc. Farm. Basica Apl. 26(3): 217-220, Dec. 1, 2005.

Elewski, Percutaneous Absorption Kinetics of Topical Metronidazole Formulations in vitro in the Human Cadaver Skin Model, Adv. Ther. 24(2): 239-46, 2007.

Eftaiha, et al., Bioadhesive Controlled Metronidazole Release Matrix Based on Chitosan and Xanthan Gum, Mar Drugs 8:1716-1730, May 25, 2010.

El-Kamel, et al., Chitosan and Sodium Alginate-Based Bioadhesive Vaginal Tablets, AAPS PharmSci 4(4)7, Nov. 6, 2002.

Hani, et al., Formulation Design and Evaluation of Metronidazole Microspheres in a Bioadhesive Gel for Local Therapy of Vaginal Candidiasis, Lat. Am. J. Pharm. 30(1):161-167, Apr. 14, 2011.

Hanson, et al., Metronidazole for Bacterial Vaginosis: A Comparison of Vaginal Gel v. Oral Therapy, J. Reprod. Med. Obstet. Gynecol. 45(11): 889-96, Dec. 13, 2000.

Hussain, et al., The Vagina as a Route for Systemic Drug Delivery, J. Control. Release 103:301-313, Jan. 13, 2005.

Ibrahim, et al., Development and Characterization of Thermosensitive Pluronic-based Metronidazole in situ Gelling Formulations for Vaginal Application, Acta. Pharm. 62(1): 59-70, Mar. 1, 2012.

Jain, et al., Mucoadhesive Liposomes Bearing Metronidazole for Controlled and Localized Vaginal Delivery, Proc. Control. Release Soc. 23:701-02, Nov. 1, 1996.

Jansen, et al., Rosacea: Classification and Treatment, J R Soc. Med. 90(3): 144-150, Mar. 1997.

Jel Vehgari, et al., Evaluation of Mechanical and Rheological Properties of Metronidazole Gel as Local Delivery System, Arch Pharm. Res. 34(6): 931-40, Jun. 2011.

Joesoeff, et al., Bacterial Vaginosis: Review of Treatment Options and Potential Clinical Indications for Therapy, Clinical Infectious Diseases 28(Suppl 1): S57-S65, 1999.

Kailasam, et al., Formulation and Evaluation of Once Daily Mucoadhesive Vaginal Tablet of Metronidazole, Int. J. Res. Pharm. Sci. 1(3): 308-12, Sep. 1, 2010.

Kissinger, et al., A Randomized Treatment Trial: Single versus 7-day Dose of Metronidazole for the Treatment of Trichomonas Vaginalis among HIV-infected Women, J. Acquired Immune Defic. Syndr. 55(5): 565-71, Dec. 15, 2010.

Livengood, et al., Comparison of Once-daily and Twice-daily Dosing of 0.75% Metronidazole Gel in the Treatment of Bacterial Vaginosis, Sex. Transm. Dis. 26(3): 137-42, Mar. 1999.

Lugo-Miro, et al., Comparison of Different Metronidazole Therapeutic Regimens for Bacterial Vaginosis: A Meta-analysis, J. Am. Med. Assoc 268(1) 92-95, Jul. 1, 1992.

Novakov Mikic, et al., Comparison of Local Metronidazole and Local Antiseptic in the Treatment of Bacterial Vaginosis, Arch. Gynecol. Obster 282:43-47, Oct. 7, 2009.

Pavelic, et al., Characterization and in vitro Evaluation of Bioadhesive Liposome Gels for Local Therapy of Vaginitis, Int. J. Pharm. 301:140-48, Jul. 15, 2005.

Perioli, et al., FG90 Chitosan as a New Polymer for Metronidazole Mucoadhesive Tablets for Vaginal Administration, Int. J. Pharm. 377:120-27, Jul. 30, 2009.

Schwebke, et al., Tinidazole versus Metronidazole for the Treatment of Bacterial Vaginosis, Am. J. Obstet. Gynecol. 204(3) 211.e1-211.e6, Mar. 1, 2011.

(56) References Cited

OTHER PUBLICATIONS

Shaaban, et al., Pilot Randomized Trial for Treatment of Bacterial Vaginosis Using in situ Forming Metronidazole Vaginal Gel, J. Obstet. Gynecol. Res. 37(7): 874-81, Jul. 1, 2011.
Shankar, et al., Development and Characterization of Bioadhesive Gel of Microencapsulated Metronidazole for Vaginal Use, Iran J. Pharm. Res. 9(3): 209-19, Nov. 24, 2010.
Shilpa, et al., Design of Mucoadhesive Vaginal Metronidazole Films, Acta Pharm. Sci. 52:181-89, Aug. 5, 2010.
Skalko, et al., Liposomes with Metronidazole for Topical Use: The Choice of Preparation Method and Vehicle, Journal of Liposome Research 8(2): 283-93, 1998.
Matsumoto et al., Pharmaceutical Sciences, Nanzando Co., Ltd., 1989, p. 60.
Fukuyo Torii, Office Action in Japanese Patent Application No. 2016-154,117, Japanese Patent Office (dated May 29, 2017).

\* cited by examiner

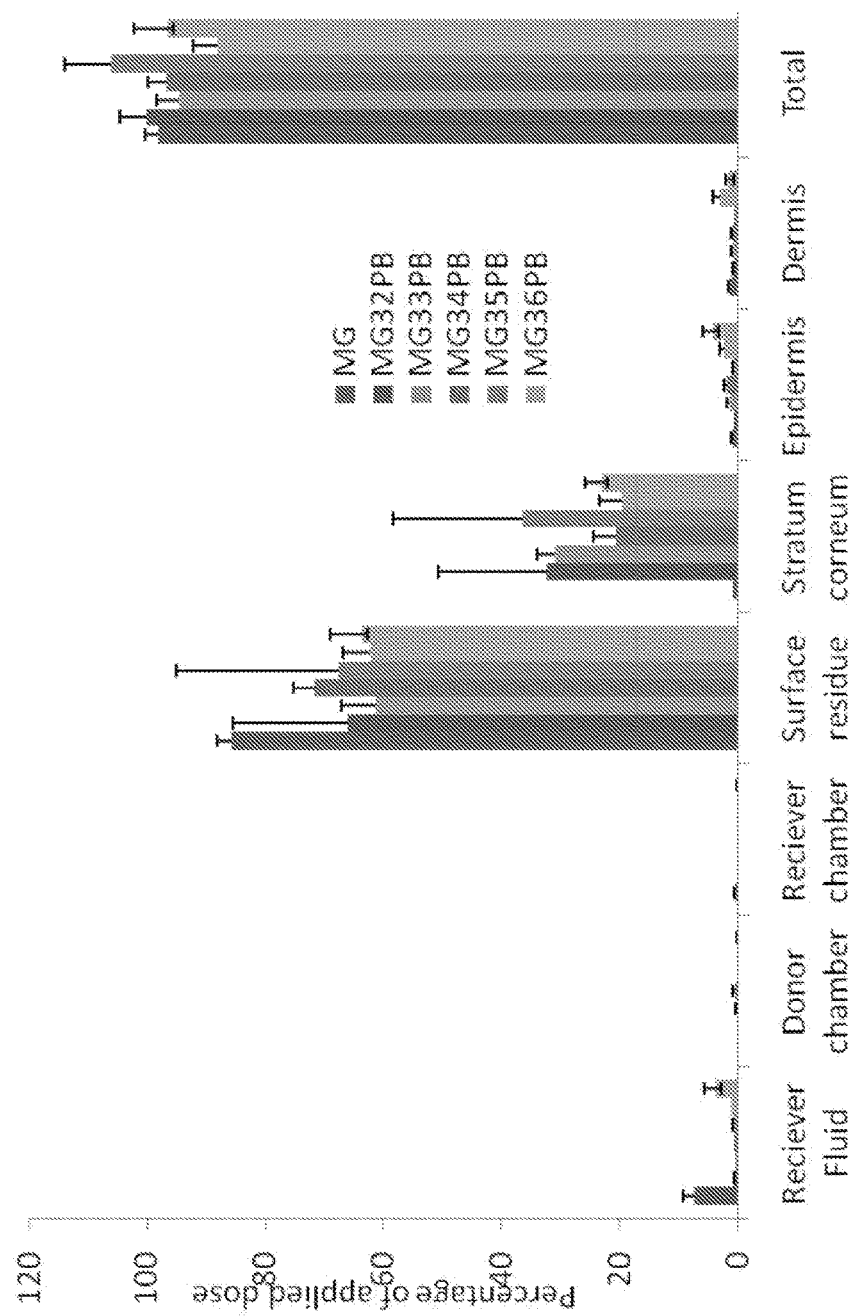

AQUEOUS-BASED METRONIDAZOLE GEL FORMULATIONS

1. CROSS REFERENCE TO RELATED APPLICATIONS

This application is a continuation of application Ser. No. 13/536,960, filed Jun. 28, 2012, which claims the benefit of U.S. Provisional Application No. 61/502,285, filed Jun. 28, 2011 and U.S. Provisional Application No. 61/508,058, filed Jul. 14, 2011, the contents of which are incorporated herein by reference in their entireties. This application is also related to application Ser. No. 13/536,973, filed Jun. 28, 2012, which claims the benefit of U.S. Provisional Application No. 61/502,288, filed Jun. 28, 2011 and U.S. Provisional Application No. 61/508,054, filed Jul. 14, 2011, the contents of which are incorporated herein by reference in their entireties.

2. FIELD

The present disclosure relates to aqueous-based gel formulations of metronidazole and their uses, for example to treat bacterial vaginosis.

3. BACKGROUND

Bacterial vaginosis (hereafter "By") is reported to be the most common cause of vaginitis found in women of reproductive age, causing 40-50% of all vaginal infections (Sobel, 1997, "Review Article: Vaginitis," New Engl J Med 337:1896-1903). BV can cause bothersome symptoms, and can at times increase the risk of acquiring sexually transmitted diseases, such as HIV. BV is thought to represent a synergistic polymicrobial bacterial infection characterized by an overgrowth (lOOx-lOOOx) of bacterial species often found as part of normal vaginal micro flora, including *Gardnerella vaginalis, Bacteroides* spp. (some now classified as *Prevotella* spp.), anaerobic Gram-positive cocci, *Mobiluncus* spp. and *Mycoplasma hominis*. Accompanying this increase is a marked decrease in *Lactobacillus* species normally present that are believed to regulate the growth of other vaginal flora. Moreover, hydrogen peroxide-producing strains of *Lactobacillus* that dominate the vaginal flora of healthy women are replaced by non-hydrogen peroxide-producing strains in women with BV (Amsel et al., 1983, Am J. Med 74:14; Sobel el al, 1990, Infect Med May:24). Generally, studies show that there are greater quantitative than qualitative differences in the vaginal micro flora of women with BV as compared to healthy women, indicating that some of the clinical signs and symptoms of BV may be related to quantitative differences in one or more naturally present microbial species (Masfari et al., 1986, Genitourin Med 62:256). The factors responsible for the initial disruption of, and eventual change in, the balance of species in the vaginal ecosystem are not well understood, and the exact locus of the infection is unknown, complicating efforts for developing suitable treatments.

Metronidazole, approved by the FDA on Jul. 18, 1963, and clindamycin are two of the oldest and most commonly used antibiotics that are prescribed to treat women who suffer from and/or are diagnosed with BV ((CDC 2006 STD Treatment Guidelines MMWR 2006; 55 (No. RR-7)).

Metronidazole is available from numerous sources as oral tablets and capsules, injectable solutions, 0.75 wt % topical lotions, creams and gels, 1.0 wt % topical gels and 0.75 wt % vaginal gels. The topical creams, lotions and gels are generally indicated for the treatment or rosacea, wherein the vaginal gels, for example the 0.75 wt % metronidazole vaginal gel sold by Medicis under the brand name METROGEL VAGINAL®), are indicated for the treatment of BV.

Despite their common use, treatment with the 0.75 wt % vaginal metronidazole gels such as METROGEL VAGINAL®) are less than ideal. To be effective, the gels must be applied once or twice a day for a period of five days.

Moreover, recurrence of BV is commonly observed in up to 30% of women within three months of treatment, whether oral or vaginal. The reasons for recurrence remain unclear. See, e.g., Larsson, 1992, Int J Std Aids 3:239-247; Wilson, 2004, Sex Transm Infect 80:8-11. It has been shown in a double-blind, placebo-controlled crossover trial that intravaginal treatment with a 0.75% metronidazole gel resulted in a recurrence rate of about 15% one month following treatment. See, Hillier et al, June 1993, "Efficacy of Intravaginal 0.75% Metronidazole Gel for the Treatment of Bacterial Vaginosis," Obstet Gynecol 81(6):963-967. Vulvovaginal candidiasis, commonly known as a yeast infection, is also observed in approximately 10% of women following treatment for BV.

In view of the fact that BV is currently the most prevalent form of vaginal infection in women of reproductive age, there is a real and immediate need for new therapies that address one or more of the shortcomings of currently available BV treatments. For example, it would be desirable to have available an intravaginal treatment that provides an effective cure in a single application, and/or that provides a more effective cure than currently available 0.75 wt % intravaginal metronidazole gels, reduces the rate of recurrence of BV following a successful course of treatment, and/or reduces the incidence of vulvovaginal candidiasis following a successful course of BV treatment.

4. SUMMARY

It has been surprisingly discovered that formulating metronidazole ("MTZ") in mucoadhesive aqueous-based gel vehicles at concentrations higher than those currently employed to treat bacterial vaginosis ("BV") yields treatments that overcome several of the shortcomings of current intravaginal BV treatments such as METROGEL VAGINAL®. For example, as will be discussed in more detail below, "high dosage" mucoadhesive MTZ aqueous-based gels comprising about 1-2% by weight ("wt %") of MTZ surprisingly deliver significantly higher than expected local concentrations of MTZ, and significantly higher local concentrations of MTZ than are delivered by a 0.75 wt % MTZ gel similar to METROGEL VAGINAL®) in in vitro skin permeation experiments carried out with human cadaver skin. When used to treat women suffering from and/or diagnosed with BV, an embodiment of the high dosage mucoadhesive aqueous-based gels comprising 1.3 wt % MTZ yielded superior results as compared to METROGEL VAGINAL®). For example, when applied once daily for a period of three days, the efficacy achieved with the 1.3 wt % high dosage MTZ gel of the instant disclosure was about the same as that achieved in women treated with the currently available FDA-approved 0.75 wt % MTZ gels in accordance with their standard 5-day treatment regimen. Quite surprisingly, a single application of the high dosage 1.3 wt % MTZ gel of the instant disclosure was found to be as effective as a course of 0.75 wt % MTZ gel applied once a day for a period of five days. This discovery is significant, as it provides for effective treatment of BV with exposure to far less total MTZ, reducing the risk of untoward and even dangerous side effects.

While not intending to be bound by any theory of operation, it is believed that the surprising efficacy of the exemplary 1.3 wt % MTZ aqueous-based gel may be due, in part, to the above-mentioned unexpectedly high levels of MTZ released locally by the novel mucoadhesive aqueous-based gels described herein.

It has also been surprisingly discovered that when the 1.3 wt % MTZ high dosage gel is applied once daily to a vagina of a woman suffering from and/or diagnosed with BV for a period of five days, the efficacy is dramatically increased as compared to METROGEL VAGINAL®), as determined by, for example, any one of increased cure rates, increased time to resolution of symptoms, increased time to recurrence of symptoms, and/or decreased incidence of recurrence. Thus, it has been surprisingly discovered that when a high dosage mucoadhesive MTZ aqueous-based gel is applied once daily to the vagina of a woman who suffers from and/or is diagnosed with BV for a period of five days, the efficacy achieved is far superior to, and the incidence of BV recurrence remarkably reduced, as compared to women treated with the currently available FDA-approved 0.75% metronidazole gels in accordance with their standard 5-day treatment regimen.

Moreover, women suffering from and/or diagnosed with BV treated with the high dosage 1.3 wt % MTZ formulation described herein for a period of five days exhibited another unexpected and remarkable result—virtually no incidence of post-treatment vulvovaginal candidiasis. To the knowledge of the Applicants, this result is unprecedented.

Accordingly, in one aspect, the present disclosure provides novel "high dosage" mucoadhesive MTZ aqueous-based gels that can be applied topically, and in particular intravaginally to a woman, to treat, among other things, BV. The high dosage mucoadhesive MTZ aqueous-based gels generally comprise about 1% to about 2% by weight MTZ, in some specific embodiments, about 1.0%, about 1.1%, about 1.2%, about 1.3%, about 1.4%, about 1.5%, about 1.6%, about 1.7%, about 1.8%, about 1.9%, or about 2.0% by weight MTZ, and one or more gelling polymers and/or agents. The MTZ can be included in the gels in the form of a free base or a salt, such as a salt formed with a pharmaceutically acceptable acid.

The gels typically include a total quantity of gelling polymer(s) sufficient to yield a viscosity in the range of about 200,000-400,000 mPa at 25° C., for example about 250,000-350,000 mPa at 25° C., using the controlled shear rate ramp method, a Bholin CVO 100 rheometer and the rheometer settings provided in Table 11, infra. Depending upon the specific gelling polymer(s) and gelling conditions used, aqueous-based gels having viscosities in this range are generally achieved by including in the gels a total quantity of gelling polymer(s) ranging from about 0.5% to about 5% by weight. In some specific embodiments, the high dosage mucoadhesive MTZ aqueous-based gels described herein will include about 1% to about 3% by weight total gelling polymer(s), and in some specific embodiments about 2% by weight total gelling polymer(s).

Skilled artisans will appreciate that different gelling polymers exhibit different degrees of mucoadhesion. For gels designed for intravaginal application to treat BV, the gelling polymers can be mucoadhesive. The specific mucoadhesive gelling polymer(s) selected are not critical for success and can be selected from amongst any mucoadhesive polymers capable of forming gels in aqueous-based solutions. Exemplary suitable mucoadhesive gelling polymers are described in more detail in the Detailed Description section. All of these mucoadhesive gelling polymers can be used singly or in combinations.

Generally, mucoadhesive gelling polymers should be selected such that, when used to make an aqueous-based gel having a viscosity in the range described above, yield a gel exhibiting a degree of mucoadhesion that is within about ±10% of that observed with exemplary high dosage mucoadhesive MTZ aqueous-based gel MG33PB under the same assay conditions. In a specific exemplary embodiment, the mucoadhesive polymer(s) are selected from the group consisting of a hydroxyalkyl cellulose, a carbomer, a polycarbophil and mixtures thereof. In another specific exemplary embodiment, the mucoadhesive polymer(s) is a polycarbophil.

Skilled artisans will appreciate that while in many embodiments the one or more gelling polymer will have mucoadhesive characteristics, it need not. Polymers capable of forming gels in aqueous-based solutions that do not have mucoadhesive properties, or that yield an insufficient degree of mucoadhesion, can be used in combination with mucoadhesive agents, whether gel-forming or not, to yield high dosage mucoadhesive MTZ aqueous-based gels as described herein.

The high dosage mucoadhesive MTZ aqueous-based gels also comprise a solvent system for the MTZ. It is well-known that MTZ presents solubility problems when attempting to formulate gels useful for topical and vaginal administration with excipients approved by the FDA for use in humans. Others have attempted to solubilize MTZ in aqueous solutions at concentrations of greater than 0.75% or 1.0% by weight. For example, U.S. Pat. No. 6,881,726 describes the use of cyclodextrin and beta-cyclodextrin to enhance the solubility of MTZ in aqueous-based solutions. U.S. Pat. No. 7,348,317 describes the additional use of niacin and niacinamide to enhance the solubility of MTZ in aqueous-based solutions. Still others have attempted to increase the concentration of MTZ in aqueous-based solutions using surfactants. Any of these solvent systems can be used to solubilize the MTZ to the desired concentration in the high dosage mucoadhesive MTZ aqueous-based gels described herein.

Although solubility enhancing agents can be used, it has been surprisingly discovered that MTZ can be solubilized at concentrations sufficient to yield high dosage mucoadhesive MTZ aqueous-based gels containing about 1% to about 2% by weight MTZ without having to use solubility enhancing compounds, such as those described above. This is advantageous, because agents such as cyclodextrins and beta-cyclodextrins in many instances enhance the water-solubility of compounds by forming complexes, yielding complex formulations where the compound is not uniformly dissolved in the formulation, agents such as niacin and niacinamide may themselves have undesired pharmacological properties at certain concentrations, and agents such as surfactants can cause gels to be multiphasic.

Accordingly, also provided is a novel solvent system useful for preparing high dosage MTZ gels as described herein. The novel solvent system yields high dosage mucoadhesive MTZ aqueous-based gels that are homogeneous, i.e., the MTZ is dissolved in the gel, and that are shelf-stable for long periods of time, such as six months or more, when stored at a temperature in the range of about 25° C. to about 40° C. Indeed, a specific exemplary embodiment of a high dosage mucoadhesive MTZ aqueous-based gel comprising 1.3 wt % MTZ has been found to be stable for a period of at least 18 months when stored at temperatures of 25° C. and 40° C.

The novel solvent system generally utilizes one or more solvents that collectively have a saturated MTZ solubility at 25° C. that is sufficient to yield a gel containing the desired concentration of MTZ. Generally, such solvents will each have a saturated MTZ solubility at 25° C. of at least about 10 mg/g, although skilled artisans will appreciate that when solvents are selected that have appreciably higher saturated MTZ solubilities, the novel solvent system may include solvents with lower saturated MTZ solubilities. A non-limiting list of solvents having suitable saturated MTZ solubilities that may be used as components of the novel solvent system are provided in the Examples section.

Certain classes of solvents have been discovered to have saturated MTZ solubilities at 25° C. of at least about 20 mg/g. For example, it has been discovered that certain alcohols, for example lower aliphatic alcohols such as ethanol and lower aromatic alcohols such as benzyl alcohol, certain diols, such as, for example lower aliphatic diols (including, for example, lower aliphatic glycols such as ethylene glycol and propylene glycol) and certain polyethers, such as, for example, polyoxyalkylenes having molecular weights in the range of about 200 to about 600 ("lower polyoxyalkylene") (including, for example, PEG 400) have saturated MTZ solubilities at 25° C. in this range. Indeed, certain lower aromatic alcohols have significantly higher saturated MTZ solubilities at 25° C., for example, at least about 50 mg/g. As a specific example, benzyl alcohol has a saturated MTZ solubility of about 72 mg/g at 25° C. All of these solvents and others having saturated MTZ solubilities at 25° C. of at least about 20 mg/g can be used alone and in various combinations in the novel solvent systems to solubilize MTZ in the high dosage mucoadhesive MTZ aqueous-based gels described herein.

In some embodiments, the novel solvent system comprises at least one solvent having a saturated MTZ solubility at 25° C. of at least about 50 mg/g and optionally one or more solvents having a saturated MTZ solubility at 25° C. of at least about 20 mg/g. In some embodiments, the novel solvent system comprises at least one solvent having a saturated MTZ solubility at 25° C. of at least about 50 mg/g and one or more solvents that collectively have a saturated MTZ solubility at 25° C. of at least about 20 mg/g. In some specific embodiments, each of the solvents has a saturated MTZ solubility at 25° C. of at least about 20 mg/g.

In some specific embodiments, the novel solvent system comprises from about 1 wt % to about 5 wt % of the at least one solvent having a saturated MTZ solubility at 25° C. of at least about 50 mg/ml, with the remaining about 95 wt % to about 99 wt % being composed of the one or more solvents that collectively have a saturated MTZ solubility at 25° C. of at least about 20 mg/ml. In some specific embodiments, the solvent system comprises about 1.0 wt %, about 1.5 wt %, about 2.0 wt %, about 2.5 wt %, about 3.0 wt %, about 3.5 wt %, about 4.0 wt %, about 4.5 wt % or about 5.0 wt % (or any range bracketed by any of these values) of the at least one solvent having a saturated MTZ solubility at 25° C. of at least about 50 mg/ml and the remainder being composed of the one or more solvents that collectively have a saturated MTZ solubility at 25° C. of at least about 20 mg/ml.

It has been discovered that ternary solvent systems utilizing one or more lower aromatic alcohols; one or more lower aliphatic diols; and one or more lower polyoxyalkylenes yield good results. Accordingly, in some specific embodiments, the high dosage mucoadhesive MTZ aqueous-based gels described herein utilize a novel solvent system for MTZ that comprises one or more lower aromatic alcohols, one or more lower aliphatic diols and one or more lower polyoxyalkylenes.

In some specific embodiments, the solvent systems described herein do not include, or are substantially free of, other agents known to enhance the solubility of MTZ in aqueous-based solutions, such as cyclodextrins, beta-cyclodextrins, niacin, niacinamide and/or surfactants. In some specific embodiments, the solvent system is a ternary solvent system that consists only of one or more lower aromatic alcohol(s), one or more the lower alkylene diol(s) and one or more polyoxyalkylene(s) and does not include any other additional agents or solvents.

The one or more lower aromatic alcohol can be a phenolic, primary, secondary or tertiary alcohol, and therefore may include aliphatic or heteroaliphatic groups in addition to an aromatic group. The one or more lower aliphatic diols and lower polyoxyalkylenes can be saturated or unsaturated and can include primary, secondary and/or tertiary alcohol groups. Exemplary lower aromatic alcohols, lower aliphatic diols and lower polyoxyalkylenes useful in this specific embodiment of the novel solvent system and high dosage mucoadhesive MTZ aqueous-based gels described herein are described in more detail in the Detailed Description section. In some specific embodiments, the one or more lower aromatic alcohol is benzyl alcohol, the one or more lower aliphatic diol is propane-1,2-diol (propylene glycol) and the one or more lower polyoxyalkylene is polyethylene glycol having a MW of about 400 (PEG 400).

In some specific embodiments, the solvent system comprises about 3.5% to about 5% by weight total lower aromatic alcohol(s) and about 95% to about 96.5% by weight total lower aliphatic diol(s), about 95% to about 96.5% by weight total lower polyoxyalkylene(s) or about 95% to about 96.5% by weight of a mixture of total lower aliphatic diol(s) and total lower polyoxyalkylene(s). When mixtures are used, the weight ratio of total lower aliphatic diol(s) to total lower polyoxyalkylene(s) may typically range from about 1:1 to about 1:2, and in some specific embodiments is about 1:1.67.

The solvent system will generally compose about 30% to about 60% by weight of the high dosage mucoadhesive MTZ aqueous-based gel. The exact amount used will depend, at least in part, on the desired amount of MTZ to be included in the gel. In some specific embodiments, the solvent system represents about 40-45% by weight of the high dosage mucoadhesive MTZ aqueous-based gel.

The quantities of the components of the solvent system can also be described relative to the high dosage mucoadhesive MTZ aqueous-based gels. In some specific embodiments, the high dosage mucoadhesive MTZ aqueous-based gels comprise from about 1.5% to about 2% by weight total lower aromatic alcohol(s) (for example, benzyl alcohol), about 15% to about 25% by weight total lower aliphatic diol(s) (for example, propane-1,2-diol) and/or about 15% to about 25% by weight total lower polyoxyalkylene/s) (for example, PEG 400). In some specific embodiments, the high dosage mucoadhesive MTZ aqueous-based gels comprise about 1.5% to about 2% by weight total lower aromatic alcohol(s) (for example, benzyl alcohol), about 15% by weight total lower aliphatic diol(s) (for example, propane-1,2-diol) and/or about 25% by weight total lower polyoxyalkylene/s) (for example, PEG 400). Other specific embodiments are described in the Detailed Description section, as are additional solvents and agents useful to solubilize MTZ in connection with the high dosage mucoadhesive MTZ aqueous-based gels described herein.

The pH of the high dosage mucoadhesive MTZ aqueous-based gels described herein should generally match the pH of the intended area of application, for example, when intended for intravaginal application, the pH of a healthy vagina. While not intending to be bound by any particular theory, it is believed that matching the pH of the healthy vagina permits beneficial *Lactobacillus* to flourish. Accordingly, for gels intended for intravaginal application, the pH should generally be in the range of about pH 3 to about pH 5, for example a pH of about pH 4. The pH can be adjusted and/or maintained with the aid of acids, bases and buffers, as is well-known in the art.

For example, the pH of the gel may be adjusted and/or maintained by utilizing as the aqueous phase of the gel a buffer having a suitable normality and pH. Alternatively, the pH of the aqueous phase may be adjusted with an acid or base prior to adding the gelling agent. After gelling, the pH may be adjusted further with an acid or base. This latter method may be advantageous for preparing gels utilizing gelling agents that gel most efficiently outside the desired pH range of the resultant gel. For example, carbomers gel most efficiently around neutral pH. High dosage mucoadhesive MTZ aqueous-based gels suitable for intravaginal application may be obtained by adjusting the pH of the gelling solution to approximately neutral for gelling and then adjusting the pH of the resultant gel to within a range of about pH 3 to about pH 5 with an acid. However, it has been discovered that high dosage mucoadhesive MTZ aqueous-based gels utilizing certain pH-sensitive mucoadhesive gelling polymers, such as, for example, carbomer and polycarbophil polymers, having a pH in the desired range for intravaginal application can be obtained without the aid of a buffer or pH adjustment.

The high dosage mucoadhesive MTZ aqueous-based gels described herein can also include other additional components, such as, for example, one or more preservatives, as is well-known in the art. When used, preservative(s) should generally comprise no more than about 1% or 2% by weight of the high dosage mucoadhesive MTZ aqueous-based gel. The choice of preservative(s) is not critical. Suitable useful preservatives are described in more detail in the Detailed Description section. In some specific embodiments the one or more preservative(s) are esters of 4-hydroxy benzoic acid, also known as parabens. Suitable parabens include lower alkyl esters of 4-hydroxy benzoic acid, such as, for example, methyl 4-hydroxybenzoate (methyl parben), ethyl 4-hydroxybenzoate (ethyl paraben) and propyl 4-hydroxy-benzoate (propyl paraben).

Skilled artisans will appreciate that solvents used to solubilize the MTZ in the high dosage mucoadhesive MTZ aqueous-based gels described herein may also have preservative properties. As a specific example, benzyl alcohol has well known preservative properties. When used as a solvent in the novel solvent system, the preservative properties can be used to advantage. Indeed, gels including solvents with preservative properties need not necessarily include additional preservatives. Gels that utilize the preservative properties of system solvents should, in cases where the solvent may degrade or oxidize over time, include an amount of overage that takes into account the degradation and/or oxidation such that the gel retains an amount of undegraded or unoxidized solvent having effective preservative properties after a desired period of time. For example, benzyl alcohol is known to oxidize to benzaldehyde, which does not have preservative properties. In embodiments of the high dosage mucoadhesive MTZ aqueous-based gels described herein that employ benzyl alcohol as both an MTZ solvent and as a preservative, an amount of benzyl alcohol should be included in the gel that, in addition to solubilizing the MTZ, yields a preservative effect for the duration of the expected shelf life of the gel. Overage amounts of benzyl alcohol or other solvents employed in the solvent system that are being used in part as preservatives can be determined based upon the degradation and/or oxidation properties and kinetics of the particular solvent under the desired conditions of storage.

Embodiments of high dosage mucoadhesive MTZ aqueous-based gels that include solvents having preservative properties may also include one or more additional preservatives, and/or preservatives designed to protect the solvent from degradation and/or oxidation. For example, in the case of benzyl alcohol, the high dosage gels described herein may include one or more additional preservatives that have antioxidant properties, in part to protect the benzyl alcohol from oxidation. In a specific embodiment, high dosage mucoadhesive MTZ aqueous-based gels comprising benzyl alcohol or other solvents that oxidize include one or more parabens as additional preservatives. In some specific embodiments the high dosage mucoadhesive MTZ aqueous-based gels comprise about 0.1% by weight total parabens, and in some specific embodiments about 0.02% by weight methyl paraben and about 0.08% by weight propyl paraben.

The high dosage mucoadhesive MTZ aqueous-based gels also include water, either in the form of pure water, or in the form of an aqueous buffer. Typically, the amount of water included in the gel will be less than about 70% by weight, more typically less than about 60% by weight, and in some specific embodiments in the range of about 45% to about 55% by weight.

As noted above, several embodiments of high dosage mucoadhesive MTZ aqueous-based gels prepared with the novel solvent system described herein deliver unexpectedly high local concentrations of MTZ, and significantly higher local concentrations of MTZ than a conventional 0.75 wt % MTZ gel, in in vitro skin permeation experiments carried out in a Franz Cell with human cadaver skin (and also silicone membranes). Indeed, as is described in more detail in the Examples section, virtually every high dosage MTZ aqueous-based gel tested locally delivered in the range of about 25- to about 55-fold more MTZ, when normalized for concentration, to the stratum corneum than a conventional 0.75 wt % MTZ gel. Despite the higher local MTZ concentrations delivered by the high dosage mucoadhesive MTZ aqueous-based gels described herein, significantly less MTZ was observed in receiver fluid as compared to a conventional 0.75 wt % MTZ gel in in vitro skin permeation experiments carried out in a Franz Cell with human cadaver skin. As is described in more detail in the Detailed Description section, virtually every high dosage MTZ gel tested yielded in the range of about 1- to about 20-fold less MTZ in receiver fluid, when normalized for concentration, than a conventional 0.75 wt % MTZ gel in this experiment.

Although not intending to be bound by any theory, it is believed that these properties may be significant and/or important to therapeutic applications, as they permit high local concentrations of MTZ to be delivered, potentially increasing efficacy, while at the same time in certain topical applications reducing systemic exposure, thereby reducing untoward side effects. Accordingly, in some embodiments, the various components of the high dosage mucoadhesive MTZ aqueous-based gels are selected so as to yield a high dosage gel in which the surface levels of MTZ measured in an in vitro Franz cell skin permeation study carried out with human cadaver skin or a silicone membrane, when normalized for concentration, are at least about 25-fold higher, and in some specific embodiments about 55-fold higher, than the level measured with a conventional 0.75 wt % MTZ gel, such as METROGEL VAGINAL®. In some embodiments, the various components of the high dosage mucoadhesive MTZ aqueous-based gels are selected so as to yield a high dosage gel in which the levels of MTZ measured receiver fluid in an in vitro Franz cell skin permeation study carried out with human cadaver skin, when normalized for concentration, are at least about 1-fold lower, and in some specific embodiments about 20-fold lower, than the level measured with a conventional 0.75 wt % MTZ gel, such as METROGEL VAGINAL®. A specific in vitro Franz cell experiment that can be used for the comparative studies described in Example 6.

The high dosage mucoadhesive MTZ aqueous-based gels described herein can be used for any purpose where topical treatment with MTZ is desirable. Due to their degree of mucoadhesion, they are especially useful for treating women suffering from and/or diagnosed with BV.

Accordingly, in another aspect, the present disclosure provides methods of treating women suffering from and/or diagnosed with BV using the high dosage mucoadhesive MTZ aqueous-based gels described herein. The methods generally involve applying intravaginally to a woman suffering from and/or diagnosed with BV an amount of a high dosage mucoadhesive MTZ aqueous-based gel as described herein sufficient to provide therapeutic benefit. The clinical criteria for diagnosis, as well as criteria for establishing therapeutic benefit, are described in more detail in the Detailed Description section. In some specific embodiments, the amount of high dosage mucoadhesive MTZ aqueous-based gel applied in a single application contains from about 60 mg to about 100 mg MTZ. In other specific embodiments, the amount of high dosage mucoadhesive MTZ aqueous-based gel applied in a single application contains from about 60 mg to about 90 mg MTZ, in still other specific embodiments from about 60 mg to about 80 mg MTZ, and in still other specific embodiments from about 60 mg to about 70 mg MTZ. In still other specific embodiments, the amount of high dosage mucoadhesive MTZ aqueous-based gel applied in a single application contains about 65 mg MTZ.

The frequency and duration of application can vary, and may depend upon the desired outcome. Generally, the gel is applied once per day for a period of one, two, three, four or five days, ft has been found that significant therapeutic benefit is achieved with a single application of high dosage mucoadhesive MTZ aqueous-based gel containing about 65 mg MTZ. Accordingly, in some embodiments the high dosage mucoadhesive MTZ aqueous-based gel is applied as a single application, ft has also been found that application of a high dosage mucoadhesive MTZ aqueous-based gel containing about 65 mg MTZ once per day for a period of five days yielded less incidence of BV recurrence than a similar course of treatment with an FDA-approved 0.75 wt % MTZ gel, and virtually no incidence of vulvovaginal candidiasis post-therapy. Accordingly, in some embodiments the high dosage mucoadhesive MTZ aqueous-based gel is applied once per day for a period of five days.

For use, the high dosage mucoadhesive MTZ aqueous-based gels can be packaged in any form that is convenient for the desired mode of application. In specific embodiments useful for intravaginal application, the high dosage mucoadhesive MTZ aqueous-based gel may be packaged in unit dosage form, as a specific example as a pre-filled, single dose syringe-type applicator.

When used to treat women suffering from and/or diagnosed with BV, the high dosage mucoadhesive MTZ aqueous-based gels described herein provide numerous surprising advantages, including, for example: (1) effective treatment of BV following a single application, unlike existing therapies with 0.75 wt % MTZ gels, for example, METROGEL VAGINAL®, which requires administration once or twice daily for 5 days to achieve a therapeutic effect; (2) increased efficacy as compared to METROGEL VAGINAL®) following application once per day for 5 days, as determined by any one of increased cure rates, decreased time to resolution of symptoms, increased time to recurrence of symptoms, and/or lower incidence of vulvovaginal candidiasis.

It should be understood that the above summary is not intended to describe every embodiment or every implementation of the various inventions disclosed herein. The Detailed Description and Examples section further exemplify illustrative embodiments. The various embodiments described herein are intended to be disclosed in combinations, as if each specific combination were explicitly disclosed. The Examples are representative only and should not be interpreted as exclusive, or limiting the scope of the various inventions disclosed herein.

5. BRIEF DESCRIPTION OF THE FIGURES

FIG. 1 provides a graph illustrating the mucoadhesive properties of exemplary high dosage mucoadhesive MTZ aqueous-based gels MG32PB and MG33PB to porcine gastric mucosa. Data show the percentage of MTZ that remains in the gastric mucosa as a function of time. For this experiment, data were taken every 15 sec for the first 5 min.

Figure 2:
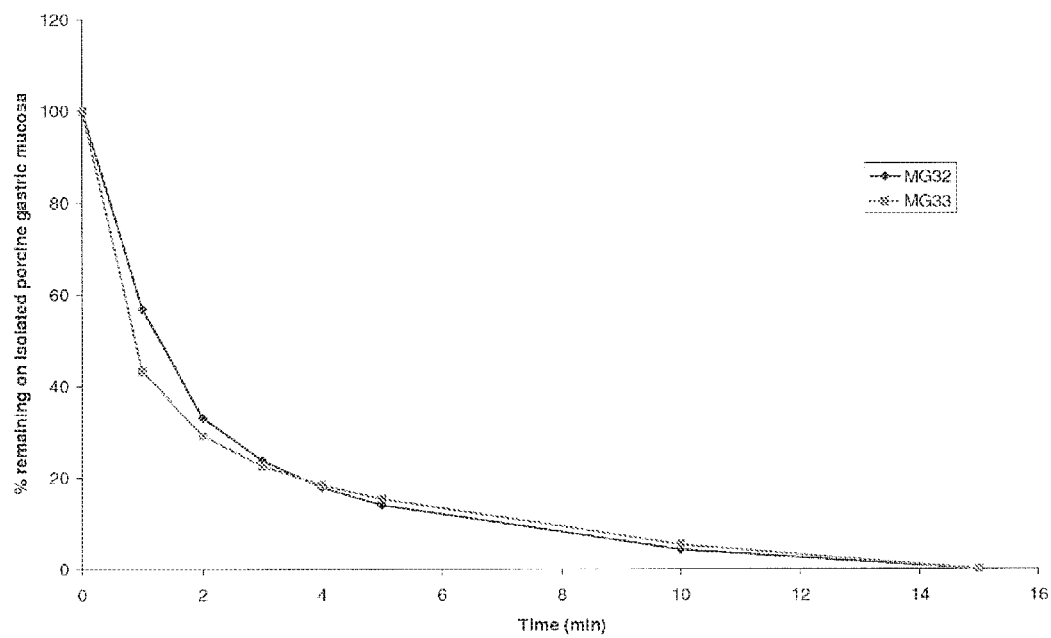

FIG. 2 provides a graph illustrating the mucoadhesive properties of exemplary high dosage mucoadhesive MTZ aqueous-based gels MG32PB and MG33PB to porcine gastric mucosa. Data show the percentage of MTZ that remains in the gastric mucosa as a function of time. For this experiment, data were taken every min for the first 15 min.

Figure 3A:
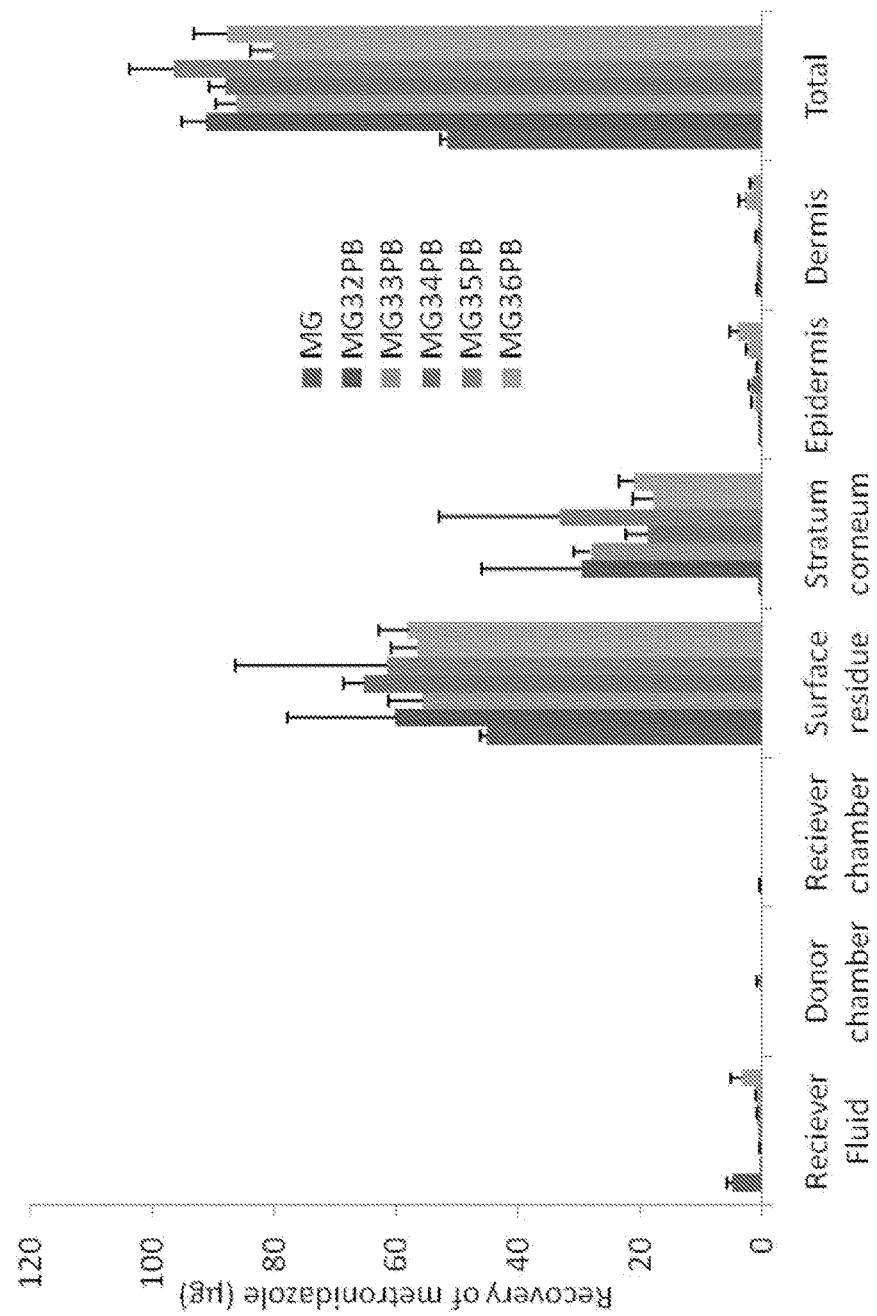
Figure 3B:
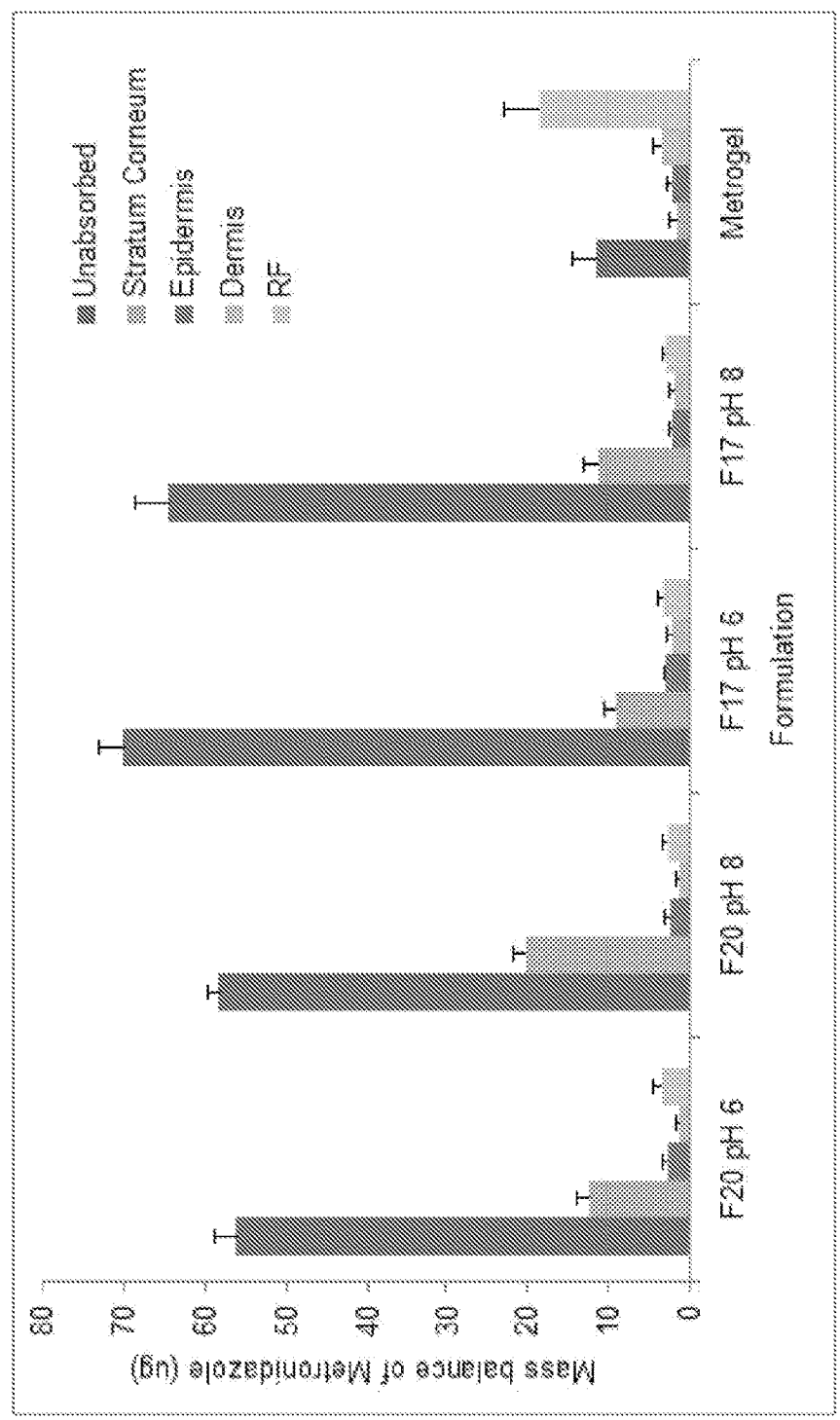

FIGS. 3A-3B provide graphs illustrating the mean amount (µg; ±SEM) of $^{14}$C-labeled MTZ recovered from various skin layers from various exemplary high dosage mucoadhesive MTZ aqueous-based gels in an in vitro Franz cell skin permeation experiment carried out with human cadaver skin.

Figure 4B:
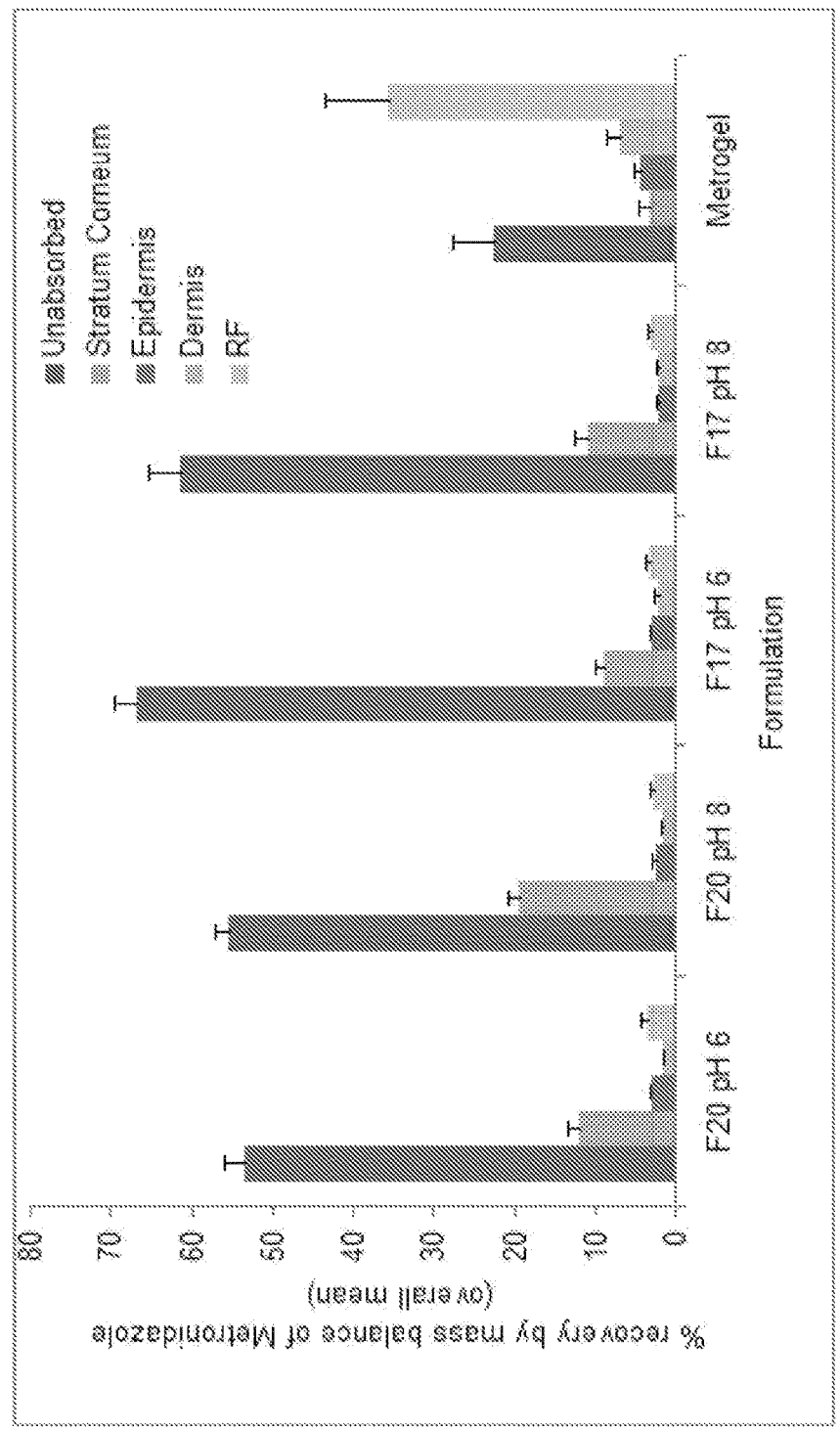

FIGS. 4A-4B provide graphs illustrating the recovery data of FIGS. 3A and 3B, respectively, represented as a mean percentage (±SEM) of the total $^{14}$C-labeled MTZ applied.

Figure 5A:
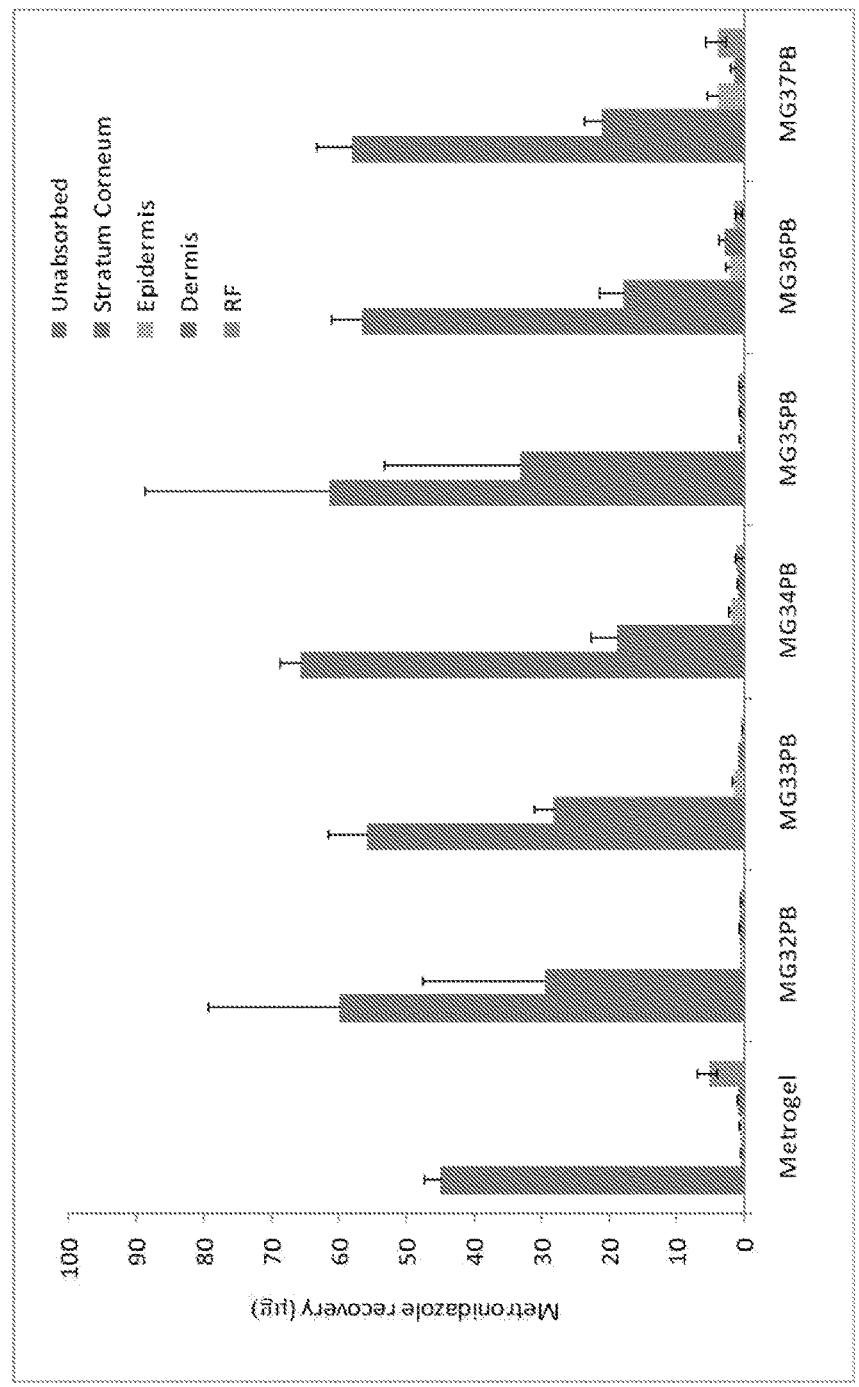
Figure 5B:
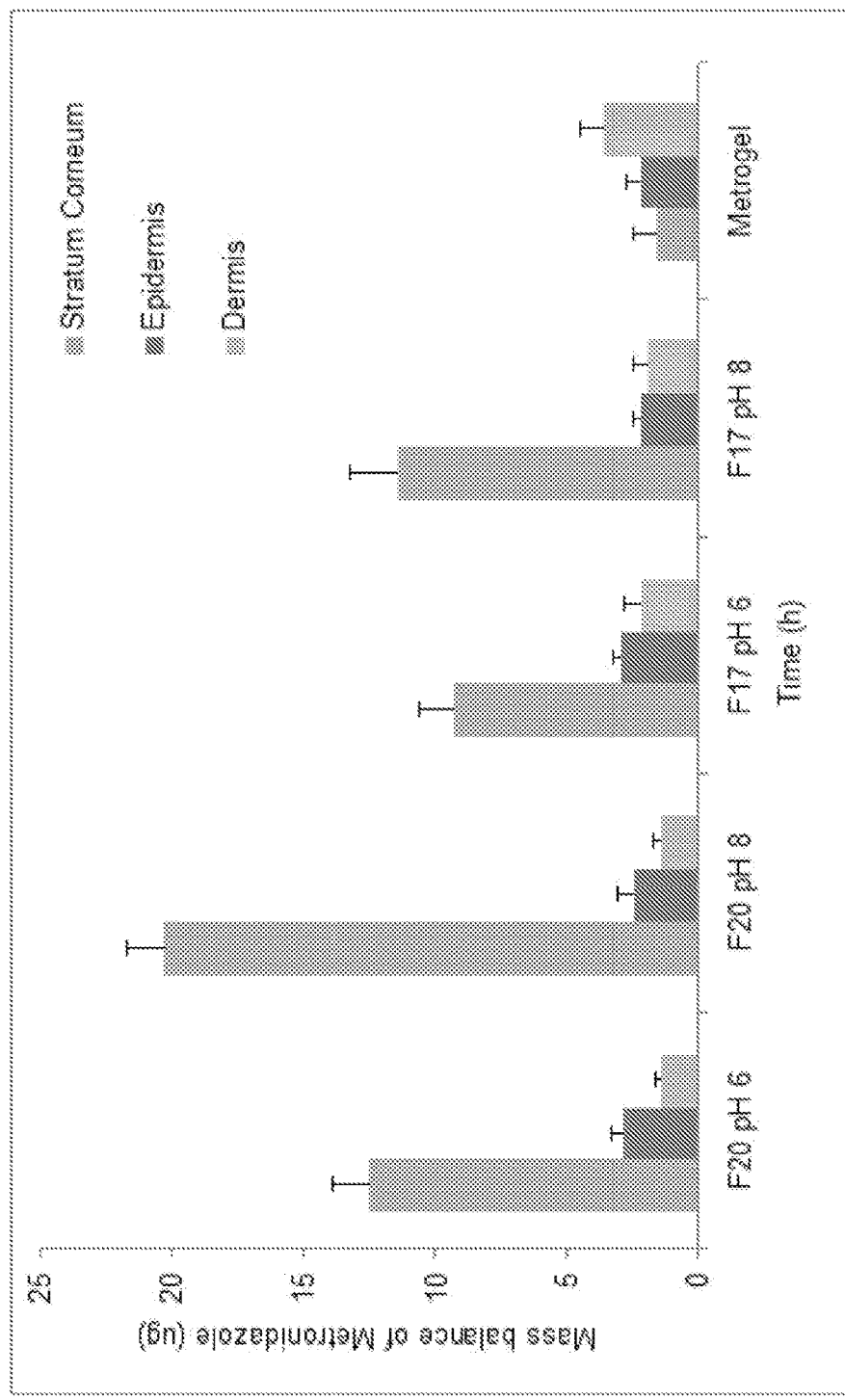

FIGS. 5A-5B provide graphs illustrating different views of the recovery data of FIG. 3A and FIG. 3B, respectively.

Figure 6A:
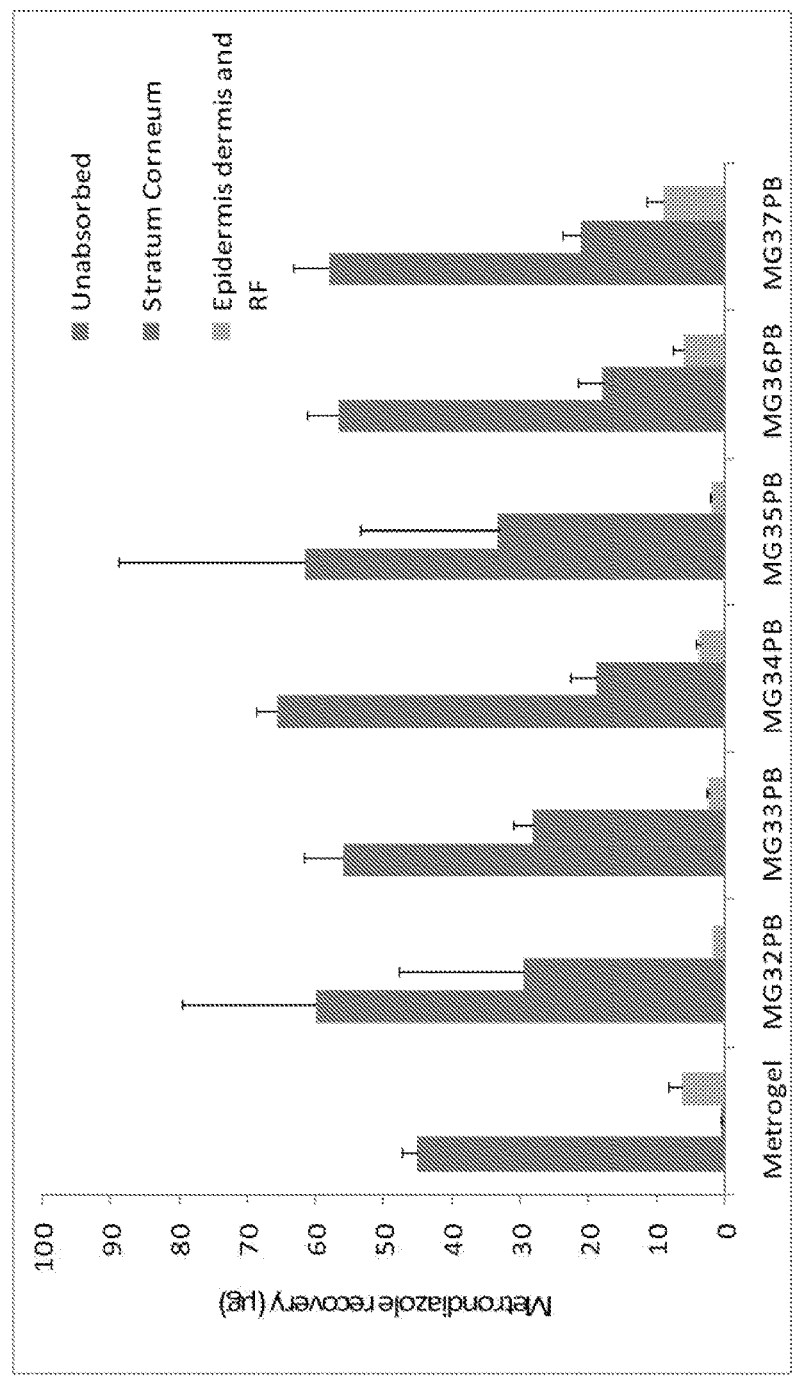
Figure 6B:
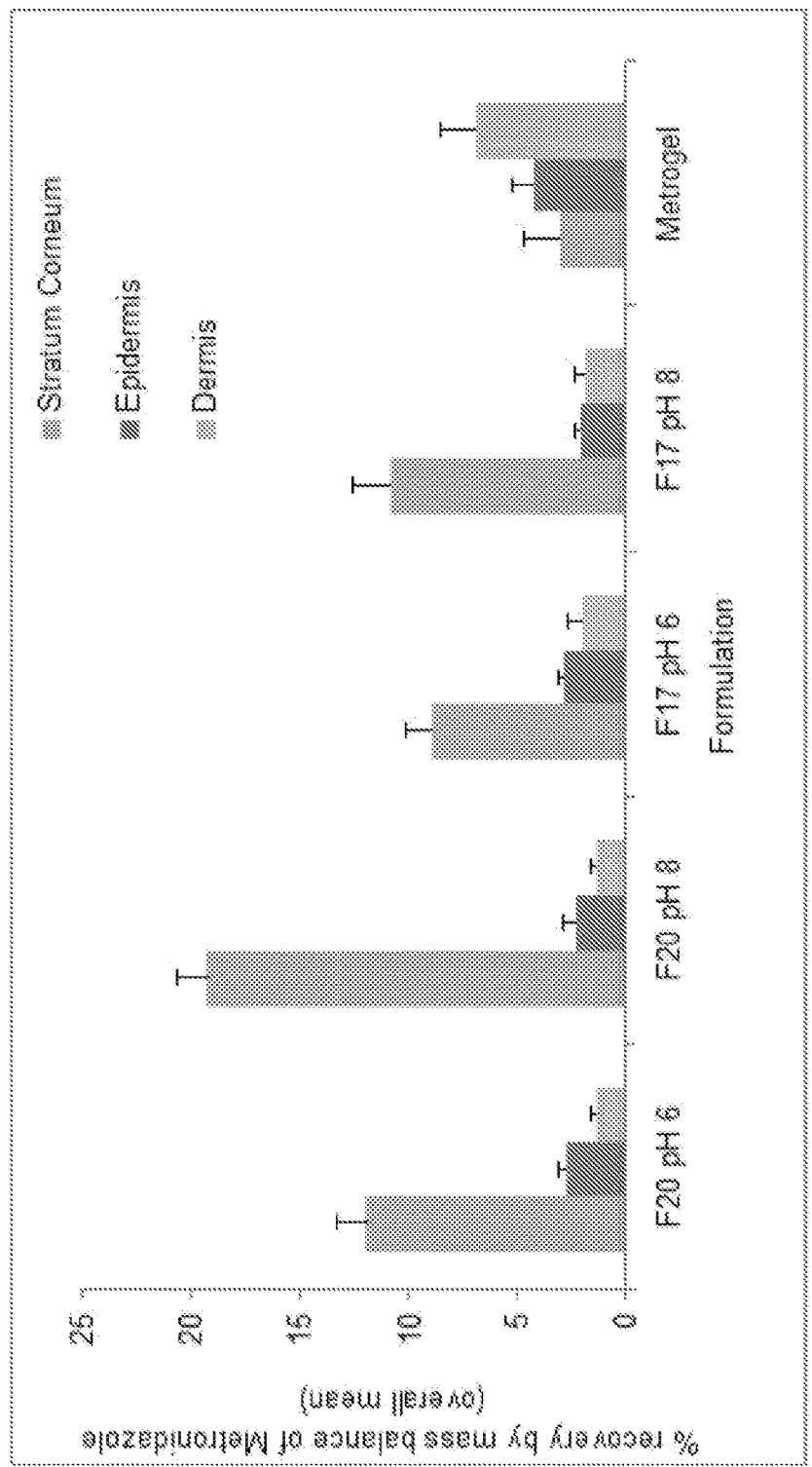

FIGS. 6A-6B provide graphs illustrating different views of the recovery data of FIG. 4A and FIG. 4B, respectively.

Figure 7:
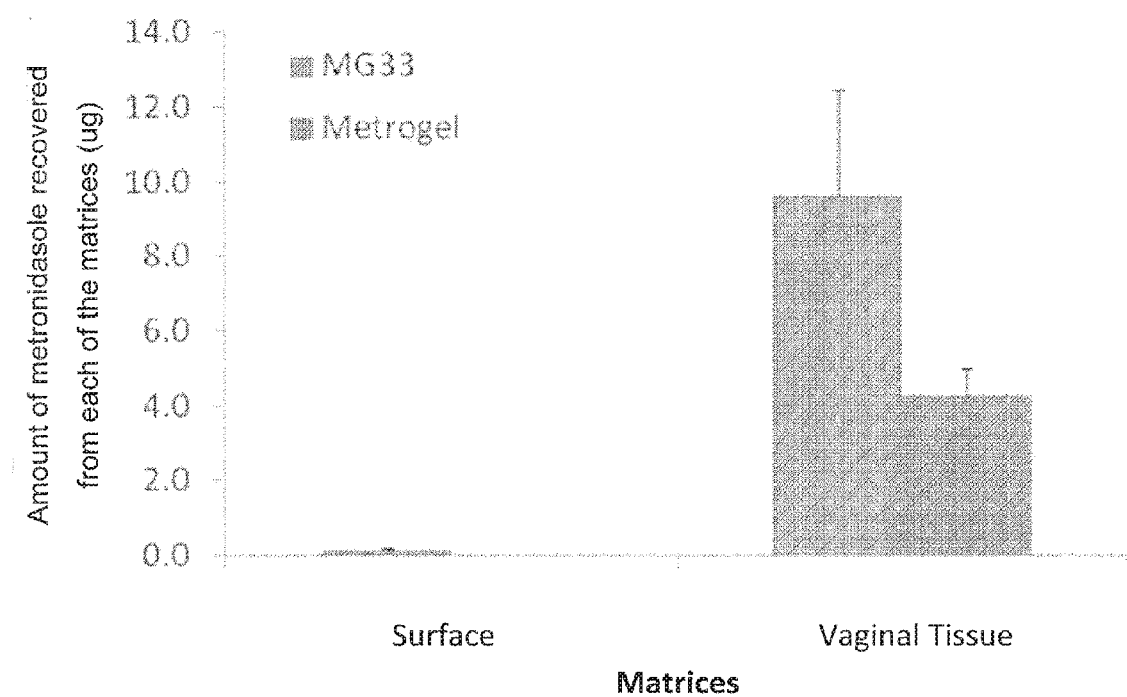

FIG. 7 provides a graph illustrating the mean amount (µg) of MTZ recovered from the surface and within vaginal tissue from an exemplary high dosage MTZ mucoadhesive aqueous-based gel and a control gel 24 hours after application in an in vitro Franz cell experiment carried out with porcine vaginal tissue. Data are mean±SEM (n=5).

Figure 8:
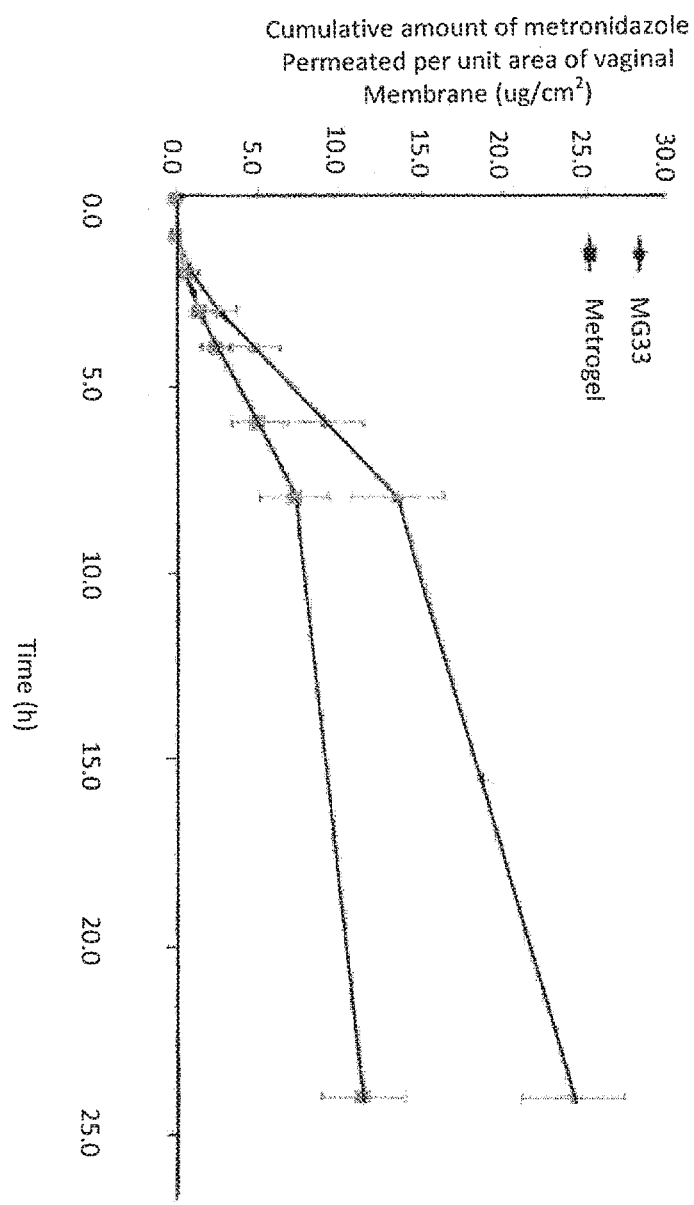

FIG. 8 provides a graph illustrating the mean amount of MTZ that permeated through porcine vaginal tissue (µg/cm$^2$ vaginal tissue) in the Franz cell experiment of FIG. 7. Data are mean±SEM (n=5).

Figure 9:
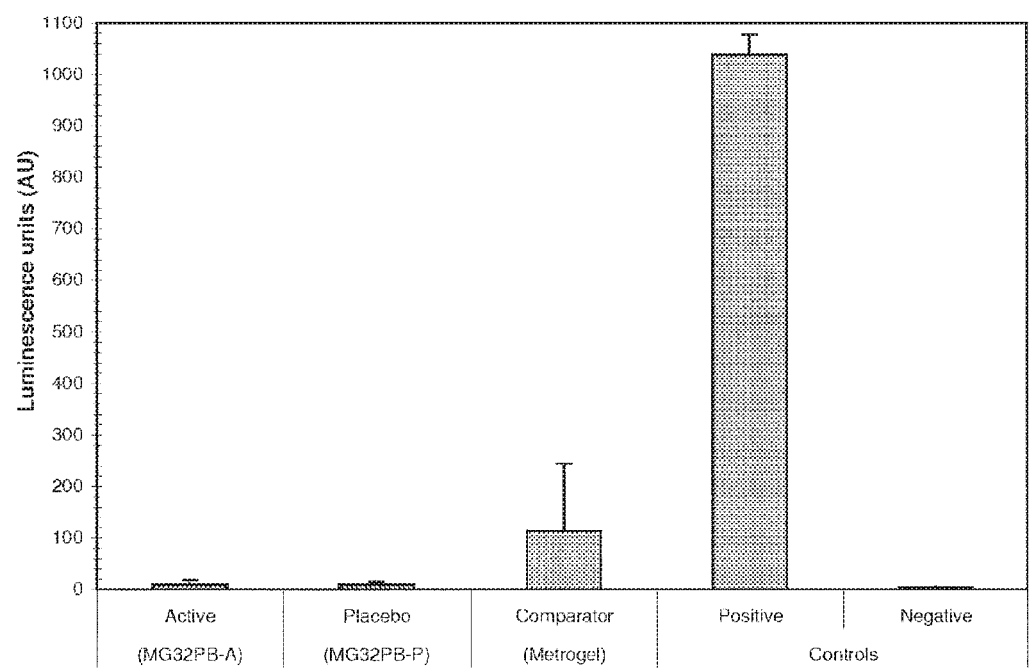

FIG. 9 provides a graph comparing the ATP released from epidermal membrane samples infected with *G. vaginalis* following a 24 hr treatment with different exemplary high dosage mucoadhesive MTZ aqueous-based gels (n=3 for active gels; n=2 for placebo gels and control).

Figure 10:
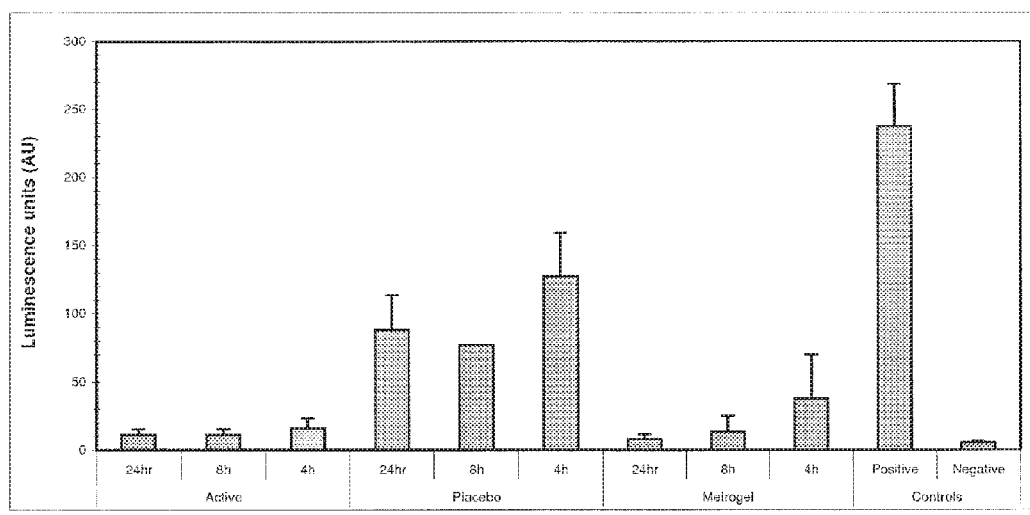

FIG. 10 provides a graph comparing the ATP released from epidermal membrane samples infected with *G. vaginalis* following treatment with exemplary high dosage MTZ gel MG33PB at different dosing times of 4, 8 and 24 hr (n=3 for MG33PB; n=2 for placebo gels and control).

Figure 11:
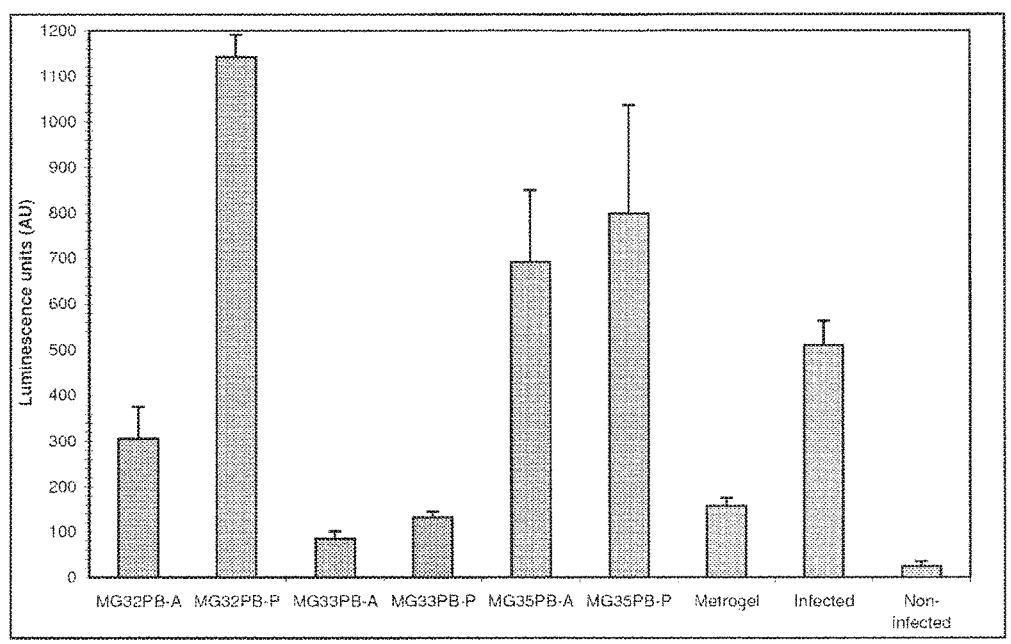

FIG. 11 provides a graph comparing the ATP released from epidermal membrane samples infected with *G. vaginalis* following a 2 hr treatment with different high dosage mucoadhesive MTZ aqueous-based gels (n=6 for active gels and control; n=3 for placebo gels).

Figure 12:
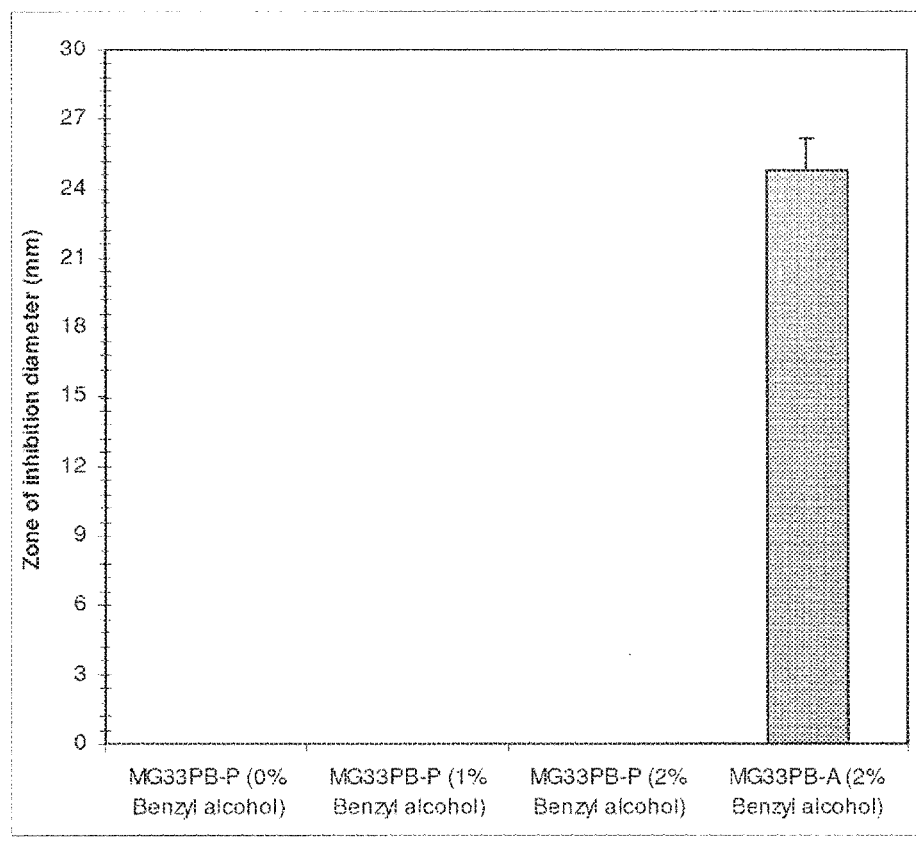

FIG. 12 provides a graph showing the zones of inhibition on the growth of *G. vaginalis* of exemplary high dosage mucoadhesive MTZ aqueous-based gel MG33PB and various placebo versions containing different quantities of benzyl alcohol.

6. DETAILED DESCRIPTION

A more complete appreciation of the various inventions disclosed herein, and many of the attendant advantages thereof, is provided by the detailed description that follows.

6.1. Definitions

As used herein throughout the specification and in the appended claims, the following terms and expressions are intended to have the following meanings:

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

6.2. Detailed Description of Specific Exemplary Embodiments

As noted in the Summary, the present disclosure provides, among other things, high dosage mucoadhesive metronidazole ("MTZ") aqueous-based gels that are useful for topical delivery of MTZ to treat, among other things, various microorganism infections, and in a specific embodiment for intravaginal application as a therapeutic approach towards the treatment of women suffering from, or diagnosed with, bacterial vaginosis ("BV"). The high dosage mucoadhesive MTZ aqueous-based gels generally comprise MTZ and one or more gelling polymers, in specific embodiments one or more mucoadhesive gelling polymers.

MTZ, also known as 2-(2-methyl-5-nitro-1//-imidazol-1-yl)ethanol, is a well-known antimicrobial agent, having activity against anaerobic Gram-negative bacilli including *Fusobacterium* species and *Bacteroides* species (e.g., *B. fragilis, B. distasonis, B. ovatus, B. thetaioaomicron,* and *B. vulgates*)'; anaerobic Gram-positive bacilli including *Clostridium* species and susceptible strains of *Eubacterium*; and anaerobic Gram-positive cocci including *Peptostreptococcus* species.

MTZ can be included in the high dosage gels described herein in the form of a free base or as a salt formed with pharmaceutically acceptable acids. Inorganic acids suitable for forming pharmaceutically acceptable salts include, by way of example and not limitation, hydrohalide acids (e.g., hydrochloric acid, hydrobromic acid, hydriodic, etc.), sulfuric acid, nitric acid, phosphoric acid and the like. Organic acids suitable for forming pharmaceutically acceptable salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-tuluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

MTZ is available commercially or can be synthesized by well-known methods.

The high dosage mucoadhesive MTZ aqueous-based gels described herein generally comprise MTZ in amounts ranging from about 1% by weight to about 2% by weight. In specific embodiments, the gels described herein comprise about 1.0%, about 1.1%, about 1.2%, about 1.3%, about 1.4%, about 1.5%, about 1.6%, about 1.7%, about 1.8%, about 1.9% or about 2.0% by weight MTZ.

The high dosage mucoadhesive MTZ aqueous-based gels also comprise one or more gelling polymers, and in specific embodiments one or more mucoadhesive gelling polymers that impart the gels with their mucoadhesive and gel-like properties. A variety of polymers that form mucoadhesive gels in aqueous-based solutions that are suitable for use in the mucoadhesive aqueous-based gels described herein are known in the art, and include by way of example and not limitation, polysaccharide hydrocolloids (including, for example, mucilages, gums such as xanthan gum and tragacanth, and glucans), celluloses and modified celluloses (including, for example, alkyl celluloses, hydroxyalkyl celluloses, carboxy celluloses and sodium carboxy celluloses), poloxomers (copolymers of polyoxyethylene and polyoxypropylene, also known as PLURONICS®), carbomers (crosslinked polymers of acrylic acid), polycarbophils (polymers of polyacrylic acid crosslinked with divinyl glycol), veegum (magnesium aluminum silicate), polyvinyl alcohol (PVA), gelatin, sodium alginate and polyvinylpyrrolidone (PVP). Exemplary suitable mucilages can be found, for example, in Malviya et al, 2011, "Applications of Mucilages in Drug Delivery-A Review," Advan Biol Res 5(1): 1-7, and the references cited therein, the disclosures of which are incorporated herein by reference.

In some specific embodiments, the gelling polymer(s) are cross-linked polymers of acrylic acids, such as for example carbomers or polycarbophils, and/or cellulosic polymers. Suitable cellulosic polymers include, but are not limited to, carboxy methyl cellulose (CMC), methylcellulose, ethyl cellulose, hydroxyl ethyl cellulose (NEC or HHX), hydroxyl propyl cellulose (HPC) and hydroxyl propyl methyl cellulose (HPMC). Suitable carbomers include, but are not limited to the various polymers sold under the trade name CARBOPOL® by Lubrizol Advanced Materials, Cleveland, Ohio, including, for example, CARBOPOL® homopolymers (polymers of acrylic acid crosslinked with allyl sucrose or allyl pentaerythritol) such as CARBOPOL®) 71G NF, CARBOPOL®) 971P NF, CARBOPOL®) 974P NF, CARBOPOL®) 980 NF, and CARBOPOL®) 981 NF; CARBOPOL®) copolymers (polymers of acrylic acid and C10-C30 alkyl acrylate crosslinked with allyl pentaerythritol) such as PEMULEN™ TR-1 NF and PEMULEN™ TR-2 NF; CARBOPOL®) interpolymers (carbomer homopolymers or copolymers that contain a block copolymer of polyethylene glycol and long chain alkyl acid ester) such as CARBOPOL®) ETD 2020 NF and CARBOPOL®) Ultrez 10 NF; "traditional" carbomers such as carbomer 934 (CARBOPOL®) 934 NF), carbomer 934P (CARBOPOL®) 934P NF), carbomer 940 (CARBOPOL®) 940 NF), carbomer 941 (CARBOPOL®) 941 NF) and carbomer 1342 (CARBOPOL®) 1342P NF); and polycarbophil (NOVEON® AA-1 USP).

Any of these and/or other mucoadhesive gelling polymers can be used, singly or in combinations, in the high dosage mucoadhesive MTZ aqueous-based gels described herein.

The one or more mucoadhesive gelling polymers are typically used in quantities such that the resultant high dosage mucoadhesive MTZ aqueous-based gel has a viscosity in the range of about 200,000-400,000 mPa at 25° C., and in some specific embodiments in the range of about 250,000-350,000 mPa at 25° C., measured using the controlled shear rate ramp method, a Bohlin CVO 100 rheometer and the rheometer settings noted in Table 11 (Example 5, infra). Depending upon the specific gelling polymer(s) and gelling conditions used, aqueous-based gels having viscosities in this range are generally achieved by including in the gels a total quantity of gelling polymer(s) ranging from about 0.5% to about 5% by weight. In some specific embodiments, the high dosage mucoadhesive MTZ aqueous-based gels described herein will include about 1% to about 3% by weight total gelling polymer(s), and in some specific embodiments about 2% by weight total gelling polymer(s).

Gels designed for intravaginal application should ideally exhibit a degree of mucoadhesion to prevent the gel from leaking when applied. Gels utilizing cellulosic and/or acrylic acid mucoadhesive gelling polymers that have viscosities in the ranges discussed above should have a suitable degree of mucoadhesion. Different gelling polymers exhibit different degrees of mucoadhesion. Gelling polymers yielding a high dosage mucoadhesive MTZ aqueous-based gel that have a degree of mucoadhesion that is within about ±10% of that of exemplary gel MG33PB (described in Example 2 and Table 5) can suitably be used. In a specific exemplary embodiment, the mucoadhesive polymer(s) are selected from the group consisting of a hydroxyalkyl cellulose, a carbomer, a polycarbophil and mixtures thereof. In another specific exemplary embodiment, the mucoadhesive polymer(s) is a polycarbophil, such as, for example, the polycarbophil sold under the trade name NOVEON® AA-1 Polycarbophil by Lubrizol, Inc.

High dosage mucoadhesive MTZ aqueous-based gels having suitable viscosities, mucoadhesion and other desirable properties utilizing carbomer 934, hydroxyethyl cellulose or polycarbophil as the mucoadhesive gelling polymer are provided in Example 2.

As noted in the Summary, the solubility of MTZ presents problems when attempting to formulate MTZ in aqueous-based formulations, such as aqueous-based gels. Specific embodiments of the high dosage mucoadhesive MTZ aqueous-based gels described herein utilize a novel solvent system which has been discovered to yield homogenous gels containing MTZ at concentrations as high as 2% or more by weight that are stable for long periods of time, for example at least about 6 months, when stored at temperatures ranging from about 25° C. to about 40° C. Surprisingly, such high dosage mucoadhesive MTZ aqueous-based gels can be prepared without the aid of agents commonly used to enhance the solubility of MTZ in aqueous solutions, such as cyclodextrins, beta cyclodextrins, niacin, niacinamide and/or surfactants.

As used herein, "stable" means that the gel exhibits the following properties: (1) an MTZ purity of at least about 95% when stored at a temperature of about 25° C. for a period of at least 6 weeks; (2) no appreciable increase (e.g., no more than about a 2-fold to 3-fold increase) in formation of crystals and/or particulates upon microscopic visual inspection at a magnification of 40× when stored at a temperature of about 25° C. for a period of at least 6 weeks, as compared to a baseline value and (3) a change in viscosity of no more than about ±50% as measured at 25° C. when stored at a temperature of about 25° C. for a period of about 6 weeks, as compared to a baseline value or a control sample stored at a temperature in the range of about 2-8° C. In addition, it is desirable, but not required, that stable gels exhibit the following additional properties: (4) a change of pH less than about ±0.3 pH units when stored at a temperature of about 25° C. for a period of 6 weeks, as compared to a baseline value or a control sample stored at a temperature in the range of about 2-8° C.; (5) a change in the efficacy of the preservative of no more than about ±20% when stored at about 25° C. for a period of at least about 6 weeks, as compared to a baseline value or a control sample stored at a temperature in the range of about 2-8° C. Assays suitable for measuring the stability of high dosage mucoadhesive MTZ aqueous-based gels are provided in Examples 4 and 5. Typically, the specific components and quantities of the novel solvent system are selected so as to yield a high dosage mucoadhesive MTZ aqueous-based gel that is stable as defined herein. Guidance for selecting solvent systems useful for preparing stable high dosage MTZ aqueous-based gels having specific quantities of MTZ is provided by way of the various exemplary high dosage gels disclosed in the Examples section.

In some specific embodiments, the components and quantities of the novel solvent system are selected to yield a stable high dosage mucoadhesive MTZ aqueous-based gel having the MTZ purity, homogeneity and viscosity properties discussed above, and optionally the pH and preservative efficacy properties discussed above, when stored at a temperature of about 40° C. for a period of about 6 weeks. In other specific embodiments, the components and quantities of the novel solvent system are selected to yield a stable high dosage mucoadhesive MTZ aqueous-based gel having the above-discussed MTZ purity, homogeneity and viscosity properties, and optionally the above-discussed pH and preservative efficacy properties, when stored at a temperature of in the range of about 25-40° C., and in specific embodiments at a temperature of about 25° C. or about 40° C., for a period of 6 months, or even more, for example, for periods as long as 18 months. In yet other specific embodiments, the components and quantities of the novel solvent system are selected to yield a stable high dosage mucoadhesive MTZ aqueous-based gel having the above-described MTZ purity, homogeneity, viscosity, pH and optionally preservative efficacy properties discussed above when stored at a temperature in the range of about 25-40° C., and in specific embodiments at a temperature of about 25° C. or about 40° C., for a period of about 6 months, or even more, for example, for periods as long as about 18 months.

Various novel solvent systems are described in the Summary section, supra. In some specific embodiments, the novel solvent system is a ternary system that comprises one or more lower aromatic alcohol, one or more lower aliphatic diol and/or one or more polyoxyalkylene having a MW in the range of about 200 to about 600 ("lower polyoxyalkylene").

As used herein, "lower alcohol" includes saturated and unsaturated non-aromatic and aromatic alcohols having from 1 to 15 carbon atoms and that may optionally include one or more heteroatoms, for example, one or more oxygen atoms, replacing the carbon atom(s). Lower nonaromatic alcohols may include straight-chained, branched or cyclic primary, secondary or tertiary lower aliphatic alcohols and lower heteroapliphatic alcohols. Examples of lower aliphatic alcohols include, but are not limited to, methanol, ethanol, propan-1-ol, propan-2-ol, butan-1-ol, butan-2-ol, 2-methylpropan-1-ol, 2-methylpropan-2-ol, pentan-1-ol, pental-2-ol, pentan-3-ol, 3-methylbutan-1-ol, hexan-1-ol, hexan-2-ol, hexan-3-ol, and cyclohexanol. Examples of lower heteroaliphatic alcohols include, but are not limited to, alkylene glycol monoalkyl ethers such as, for example, ethylene glycol monoalkyl ethers, propylene glycol monoalkyl ethers and tetraglycol. In some specific embodiments, lower nonaromatic alcohols such as lower aliphatic and lower heteroaliphatic alcohols contain from one to 8 non-hydrogen atoms, including any heteroatoms.

Lower aromatic alcohols include lower alcohols that have aromatic character, which may be contributed by an aromatic (e.g., phenyl, naphthyl, etc.) pendant group on a non-aromatic alcohol, such as an aliphatic alcohol or a heteroaliphatic alcohol. Accordingly, the alcohol group may be phenolic, primary, secondary or tertiary. Examples of lower aromatic alcohols include, but are not limited to, phenol, benzyl alcohol, 2-methylbenzyl alcohol, and phenoxyethanol.

As used herein, "lower aliphatic diol" includes saturated or unsaturated, straight-chained, branched or cyclic aliphatic diols containing from two to ten carbon atoms. The alcohol groups may be, independently of each other, primary, secondary or tertiary. In some specific embodiments, the lower aliphatic diol is a saturated or unsaturated straight-chain or branched diol, referred to herein as a "lower alkylene diol" (also referred to as "lower glycols"). In some specific embodiments, the lower alkylene diol is a saturated straight-chained or branched diol, referred to herein as a "lower alkyl diol." In some specific embodiments, the lower alkyl diol is a straight-chain diol, referred to herein as a "lower 77-alkyl diol." Specific examples of lower aliphatic diols useful in the solvent systems and gels described herein include, but are not limited to, ethane-1,2-diol (ethylene glycol), propane-1,2-diol (propylene glycol), propane-1,3-diol, butane-1,2-diol, butane-1,3-diol, butane-2,3-diol, butane-1,4-diol, pentane-1,5-diol, pentane-1,2-diol, 2-methyl-2,4-pentanediol, etc.

As used herein, "lower polyoxyalkylene" includes polymers formed from lower aliphatic diols and that have a molecular weight in the range of about 200 to about 600. Specific examples of lower polyoxyalkylenes useful in the solvent systems and gels described herein include, but are not limited to, polyethylene glycol (for example, PEG 200, PEG 400 and PEG 600), polypropylene glycol (for example PPG-9) and dipropylene glycol.

The novel ternary solvent system generally comprises about 3.5% to about 5% by weight total lower aromatic alcohol(s), and about 95% to about 96.5% by weight of a mixture of total lower aliphatic diols and polyoxyalkylenes, where the weight ratio of the total lower aliphatic diols to total polyoxyalkylenes is in the range of about 1:1 to about 1:2, and in some specific embodiments about 1:1.67.

The solvent system may include additional agents and solvents, such as, for example, additional agents or solvents that enhance the solubility of MTZ in aqueous solutions, such as, for example, cyclodextrins, beta-cyclodextrins, niacin and/or niacinamide. However, it has been discovered that high dosage MTZ aqueous-based gels that are homogeneous and have good shelf stability properties can be prepared using solvent systems that do not include such additional solubilizing agents, and in specific embodiments include only lower aromatic alcohols, lower aliphatic diols and lower polyoxyalkylenes. Accordingly, in some specific embodiments, the solvent system and resultant gels are substantially free of agents that enhance the solubility of MTZ in aqueous solutions, such as cyclodextrins, beta-cyclodextrins, niacin and/or niacinamide. In other specific embodiments, the solvent system is a ternary system that consists only of one or more lower aromatic alcohol(s), one or more lower aliphatic diol(s) and one or more lower polyoxyalkylene(s).

The solvent system will generally represent about 30% to about 60% by weight of the high dosage mucoadhesive MTZ aqueous-based gel, in certain embodiments about 40% to about 50% by weight of the gel, and in some specific embodiments about 40% to about 45% by weight of the gel, although the gel may include higher or lower amounts of total solvents.

A particularly useful ternary solvent system comprises benzyl alcohol as the one or more lower aromatic alcohol, propane-1,2-diol (propylene glycol) as the one or more lower aliphatic diol and polyethylene glycol having a MW of 400 (PEG 400) as the one or more lower polyoxyalkylene.

In some specific embodiments, solvent systems useful for solubilizing MTZ in the high dosage mucoadhesive aqueous-based gels described herein comprise, relative to the resultant high dosage mucoadhesive MTZ aqueous-based gel: (a) a polyoxyalkylene such as polyethylene glycol, e.g., PEG 400, at a concentration of from about 10% to about 50% by weight, and for example from about 20% to about 40% by weight, or from about 20% to about 30% by weight, and in a specific embodiment, about 25% by weight; (b) a lower aromatic alcohol such as phenoxyethanol or benzyl alcohol, and in a specific embodiment benzyl alcohol, from about 1.3% to about 2.5% by weight, or from about 1.5%-2.0% by weight, and in a specific embodiment about 2.0% by weight; and/or (c) a lower aliphatic diol, such as propane-1,2-diol, at a concentration of greater than about 3% to about 20% by weight, for example from about 15%-20% by weight, and in a specific embodiment about 15% by weight.

In still other specific embodiments, the solvent systems comprise: (a) PEG 400; (b) PEG 400 and a lower aromatic alcohol, such as benzyl alcohol; (c) PEG 400, a lower aromatic alcohol, such as benzyl alcohol and propane-1,2-diol; (d) a lower aromatic alcohol, such as benzyl alcohol; and/or (e) propane-1,2-diol.

In still other specific embodiments, the solvent systems comprise, relative to the resultant high dosage MTZ mucoadhesive aqueous-based gel: (a) about 25% PEG 400 by weight; (b) about 25% PEG 400 by weight and about 2% benzyl alcohol by weight; or (c) about 25% PEG 400 by weight, about 2% benzyl alcohol by weight and about 15% propane-1,2-diol by weight.

For gels designed for intravaginal application, it is preferable to use concentrations of benzyl alcohol that do not cause irritation at the target site in the vaginal area. Accordingly, in some specific embodiments in which the solvent system includes benzyl alcohol, the amount of benzyl alcohol included in the gel ranges from about 1.3% to about 2.5% by weight, for example about 1.5% to about 2% by weight, and in a specific embodiment about 2% by weight.

In still other specific embodiments, the high dosage mucoadhesive MTZ aqueous-based gels described herein comprise propane-1,2-diol at a concentration of at least about 3% and up to about 20% by weight, for example from about 15% to about 20% by weight, and in a specific embodiment about 15% by weight. In yet other specific embodiments, the gels comprise about 1.3% MTZ by weight and about 25% PEG 400 by weight. In yet other specific embodiments they comprise about 1.3% MTZ by weight, about 25% PEG 400 by weight, and about 2% benzyl alcohol by weight. In yet other specific embodiments they comprise about 1.3% MTZ by weight, about 25% PEG 400 by weight, about 2% benzyl alcohol by weight, and about 15% propylene glycol by weight.

In still other specific embodiments, solvent systems useful to make the high dosage mucoadhesive MTZ aqueous-based gels described herein comprise, relative to the gel, any one of (a) PEG 400 at a concentration of from about 10% to about 50% by weight, for example between about 20% and about 40% by weight or between about 20% and about 30% by weight, and in a specific embodiment about 25% by weight; (b) benzyl alcohol from about 1.3% to about 2.5% by weight, for example from about 1.5% to about 2% by weight, and in a specific embodiment about 2% by weight; (c) propane-1,2-diol at a concentration of at least about 3% and up to about 20% by weight, for example from about 15% to about 20% by weight, and in a specific embodiment about 15% by weight; (d) about 25% PEG 400 by weight; (e) about 25% PEG 400 by weight and about 2% benzyl alcohol by weight; and (f) about 25% PEG 400 by weight, about 2% benzyl alcohol by weight and about 15% propylene glycol by weight.

The pH of the high dosage mucoadhesive MTZ aqueous-based gels described herein should generally match the pH of the intended area of application, for example, when intended for intravaginal application, the pH of a healthy vagina. Accordingly, for gels intended for intravaginal application, the pH should generally be in the range of about pH 3 to about pH 5, for example a pH of about pH 4. The pH may be adjusted and/or maintained with the aid of acids, bases buffers and other pH-adjusting agents, as is well-known in the art and discussed in the Summary section.

The high dosage mucoadhesive MTZ aqueous-based gels described herein can also include other additional components, such as, for example, one or more preservatives, as is well-known in the art. When used, preservative(s) should generally comprise no more than about 1% or 2% by weight of the high dosage mucoadhesive MTZ aqueous-based gel, and will typically comprise about 0.25% to about 1.0% by weight of the high dosage mucoadhesive MTZ aqueous-based gel. The choice of preservative(s) is not critical. Numerous preservatives suitable for use in pharmaceutical formulations are well-known to those of skill. Any of these preservatives, and in some specific embodiments those having antimicrobial properties, can be used singly or in combinations in the high dosage mucoadhesive MTZ aqueous-based gels described herein. In some specific embodiments the one or more preservative(s) are esters of 4-hydroxy benzoic acid, also known as parabens. Suitable parabens include lower alkyl esters of 4-hydroxy benzoic acid, such as, for example, methyl 4-hydroxybenzoate (methyl parben), ethyl 4-hydroxybenzoate (ethyl paraben) and propyl 4-hydroxy-benzoate (propyl paraben).

Skilled artisans will appreciate that solvents used to solubilize the MTZ in the high dosage mucoadhesive MTZ aqueous-based gels described herein may also have preservative properties. For example, benzyl alcohol has well known preservative properties. When used as a solvent in the novel solvent system, the preservative properties can be used to advantage. Indeed, gels including solvents with preservative properties need not include additional preservatives. Gels that utilize the preservative properties of solvents included in the solvent system should, in cases where the solvent may degrade and/or oxidize over time, include an amount of overage that takes into account the degradation and/or oxidation such that the gel retains an amount of undegraded and/or unoxidized solvent having, in addition to effective MTZ-solubilizing properties, effective preservative properties after a desired period of time. For example, benzyl alcohol is known to oxidize to benzaldehyde, which does not have preservative properties. In embodiments of the high dosage MTZ gels described herein that employ benzyl alcohol as an MTZ solvent and as a preservative, an amount of benzyl alcohol should be included in the gel that not only solubilizes the MTZ, but that yields a preservative effect for the duration of the expected shelf life of the gel. Overage amounts of benzyl alcohol, or other solvents employed in the solvent system in part as preservatives, can be determined based upon the degradation and/or oxidation properties and kinetics of the particular solvent under the desired conditions of storage.

Embodiments of high dosage mucoadhesive MTZ aqueous-based gels that include solvents having preservative properties may also include one or more additional preservatives, and/or preservatives designed to protect the solvent from degradation and/or oxidation. For example, in the case of benzyl alcohol, the high dosage mucoadhesive MTZ aqueous-based gels described herein may include one or more additional preservatives that have antioxidant properties, in part to protect the benzyl alcohol from oxidation. In a specific embodiment, high dosage mucoadhesive MTZ aqueous-based gels comprising benzyl alcohol include one or more parabens as additional preservatives. In some specific embodiments the high dosage mucoadhesive MTZ aqueous-based gels comprise about 0.1% by weight total parabens, and in some specific embodiments about 0.02% by weight methyl paraben and about 0.08% by weight propyl paraben.

The high dosage mucoadhesive MTZ aqueous-based gels also include water, either in the form of pure water, or in the form of an aqueous buffer. Typically, the amount of water included in the gel will be less than about 70% by weight, more typically less than about 60% by weight, and in some specific embodiments in the range of about 45% to about 55% by weight.

A specific exemplary high dosage mucoadhesive MTZ aqueous-based gel comprises:
(a) at least 1.3% MTZ by weight; from about 1.2% to about 2% MTZ by weight; from about 3% to about 1.5% MTZ by weight; or about 1.3% MTZ by weight and
(b) one or more mucoadhesive gelling polymers.

Another specific exemplary high dosage mucoadhesive MTZ aqueous-based gel comprises:
(a) from about 1.2% to about 2% MTZ by weight, for example about 1.3% to about 1.5% MTZ by weight, and in a specific embodiment about 1.3% MTZ by weight; and
(b) one or more mucoadhesive gelling polymers and
(i) about 25% PEG 400 by weight; and/or (ii) about 2% benzyl alcohol by weight; and/or (iii) about 15% propane-1,2-diol by weight.

Another specific exemplary high dosage mucoadhesive MTZ aqueous-based gel comprises:

(a) about 1.3% MTZ by weight and 25% PEG 400 by weight;

(b) about 1.3% MTZ by weight, about 25% PEG 400 by weight, and about 2% benzyl alcohol by weight; or (c) about 1.3% MTZ by weight, about 25% PEG 400 by weight, about 2% benzyl alcohol by weight, and about 15% propane-1,2-diol by weight.

6.3. Methods of Making Gels

The high dosage mucoadhesive MTZ aqueous-based gels described herein may generally be prepared by dissolving the water-soluble components of the gel in water or buffer to yield an aqueous solution, mixing the components of the MTZ solvent system and dissolving the desired quantity of MTZ in the MTZ solvent system to yield an MTZ solution, mixing together the required amounts of the aqueous solution and MTZ solution, and adding the desired quantity of gelling agent to the mixture. Depending upon the gelling polymers used, it may be desirable to adjust the pH of the MTZ solution to within a specified range with acid and/or base prior to adding the gelling polymer(s), and then adjusting the pH of the resultant gel to within a desired specified range with acid or base. Specific methods for making high dosage mucoadhesive MTZ aqueous-based gels are provided in Example 2.

6.4. Uses

The high dosage mucoadhesive MTZ aqueous-based gels described herein can be used to topically administer MTZ in any context where such administration would be beneficial. In specific embodiments described further below, the gels can be advantageously used intravaginally to treat women suffering from or diagnosed with BV.

As used herein, a woman is said to be "suffering from" or diagnosed with BV if she experiences one or more of the accepted symptoms, conditions or presentations associated with BV. Individuals with BV typically present with, among other things, an unpleasant "fishy smelling" off-white, thin and homogeneous vaginal discharge without an inflammatory response. Individuals also present with a reduction in the prevalence and concentration of *Lactobacilli* (especially hydrogen peroxide producing forms) and a concomitant increase in *Gardnerella vaginalis, Mobiluncus* spp., anaerobic Gram-positive rods (of the genera *Bacteroides, Prevotella* and *Porphyromonas*), *Peptostreptococcus* spp. and *Mycoplasma hominis*. Predisposing factors are non-white ethnicity, prior pregnancy, use of an IUD, sexual activity, new sexual partners, and recent antibiotic use. BV is also associated with concurrent trichomoniasis.

Criteria for establishing a clinical diagnosis of BV are provided in, among other articles, a draft FDA guidance titled, "Guidance for Industry: Bacterial Vaginosis-Developing Antimicrobial Drugs for Treatment," draft dated July, 1998, which is incorporated herein by reference in its entirety (hereafter the "FDA Guidance"). As per the FDA Guidance, a clinical diagnosis of BV includes the following observations:

1. off-white (milky or gray), thin, homogeneous discharge with minimal or absent pruritus and inflammation of the vulva and vagina;

2. the presence of "clue cells" in >20% of the total epithelial cells on microscopic examination of a saline "wet mount";

3. vaginal secretion pH of >4.5; and 4. a fishy odor of the vaginal discharge with the addition of a drop of 10% KOH (i.e., a positive "whiff test").

These observations are commonly referred to as "Amsel criteria," and women presenting all four criteria are referred to herein as "Amsel Positive."

Women experiencing vaginosis thought to be BV also typically have a Gram's stain slide Nugent score of ≥4. The Nugent score is based upon the weighted sum of the following three bacterial morphotypes score calculated from slide exam under oil immersion at 1000× magnification:

*Lactobacillus*: large Gram-positive rods

*Gardnerella/Bacteroides* spp.: Small Gram-variable coccobacillUsmall Gram-negative Rods

*Mobiluncus* spp.: thin, curved, Gram variable rods

The criteria for BV according to Nugent's criteria is a total score of ≥7; a score of 4-6 is considered intermediate and a score of 0-3 is considered normal. A score of ≥3 is considered by the FDA to be abnormal.

Morphotypes are scored as the average number seen per oil immersion field (a minimum of 10-20 fields should be examined). Each morphotype is then given a numerical score as follows:

0=no morphotypes seen; 1+=<1 morphotype per field; 2+=1 to 4 morphotypes per field; 3+=5 to 30 morphotypes per field; and 4+=>30 morphotypes per field. The total Nugent score is calculated by summing the score of the individual morphotypes. For more information about the Nugent scoring system, see Nugent et al., 1991, "Reliability of Diagnosing Bacterial Vaginosis is Improved by a Standardized Method of Gram Stain Interpretation," J Clin Micrbiol 29(2):297-301. A woman with a Nugent score of >4 is referred to herein as "Nugent Positive."

In some embodiments, an individual who presents with at least 3 of the above Amsel criteria is considered to be suffering from and/or diagnosed with BV. In some embodiments, an individual who is Nugent Positive is considered to be suffering from and/or diagnosed with BV. In specific embodiments, an individual suffering from and/or diagnosed with BV is Amsel Positive. In still other specific embodiments, an individual suffering from and/or diagnosed with BV is both Amsel Positive and Nugent Positive.

Preferably, an individual who is suffering from and/or diagnosed with BV will not have other vaginal infections, including but not limited to *Chlamydia, trichomonas,* gonorrhea, and *Candida*. Preferably, an individual who is suffering from and/or diagnosed with BV is not being treated for other vaginal infections, including but not limited to *Chlamydia, trichomonas,* gonorrhea, and *Candida*. In one embodiment, an individual who is suffering from and/or diagnosed with BV is being treated with fluconazole.

The methods generally involve applying intravaginally to a woman suffering from and/or diagnosed with BV an amount of a high dosage mucoadhesive MTZ aqueous-based gel as described herein for a number of applications sufficient to provide a therapeutic benefit. As used herein, a "therapeutic benefit" is achieved when one or more of the symptoms of BV and/or one or more of the clinical manifestations of BV, including, for example, one or more of the Amsel criteria or the Nugent score, are ameliorated, eliminated, eradicated or improved. A treatment regimen can provide therapeutic benefit to a subject without curing the underlying BV condition.

As used herein, a symptom or manifestation of BV is ameliorated if it is decreased in magnitude after therapy, or moves closer to a level considered normal. For example, the Amsel criteria are ameliorated if the vaginal discharge returns to normal; the number of clue cells in a wet mount is less than about 20% of vaginal epithelial cells, for example, less than about 19%, 18%, 17%, 16%, 15%, 10%, 5% or even less; the pH of the vaginal secretion is reduced from about pH 4.7 to about pH 5.3 prior to treatment to within a range of about pH 4.0 to about pH 4.5, for example, pH 4.3, pH 4.2, pH 4.1, or pH 4.0 after treatment; and/or the whiff test produces no appreciable amine or "fishy" odor. Symptoms of BV are considered eliminated or eradicated if the symptoms are no longer detectable using well-known detection means (see, e.g., the various detection means provided in the Examples section and those disclosed in the FDA Guidance).

As used herein, a "therapeutically effective amount" refers to a treatment regimen with a high dosage mucoadhesive MTZ aqueous-based gel that provides therapeutic benefit.

In some embodiments, an amount of high dosage mucoadhesive MTZ aqueous-based gel is applied for a number of applications sufficient to provide an improvement in at least one Amsel criteria, and preferably at least 2 or 3, and most preferably all 4 Amsel criteria, and/or a result in a Nugent score of less than 4.

In some specific embodiments, an amount of a high dosage mucoadhesive MTZ aqueous-based gel is applied for a number of applications sufficient to yield a clinical cure. As used herein, a "clinical cure" is achieved when all four of the Amsel criteria are neutralized as noted below:

1. original discharge characteristic of BV has returned to a normal physiological discharge which varies in appearance and consistency depending upon the menstrual cycle;
2. a saline wet mount is negative for clue cells;
3. the pH of vaginal secretion is pH <4.7, typically measured using pH paper that measure from pH 4.0 to pH 6.0;
4. the whiff test is negative for any amine ("fishy") odor.

In some specific embodiments, an amount of a high dosage mucoadhesive MTZ aqueous-base gel is applied for a number of applications sufficient to yield a bacteriological cure. As used herein, a "bacteriological cure" is achieved when a Nugent Score of <4, for example, a Nugent Score of 1, 2 or 3, or in the range of 0-3, is achieved.

In still other specific embodiments, an amount of a high dosage mucoadhesive MTZ aqueous-based gel as described herein is applied for a number of applications sufficient to yield a therapeutic cure. As used herein, a "therapeutic cure" is achieved when both a clinical cure and a bacteriological cure are achieved.

In still other specific embodiments, an amount of high dosage mucoadhesive MTZ aqueous-based gel is applied for a number of applications sufficient for a physician to determine that no additional therapy is needed. In yet another specific embodiment, an amount of a high dosage mucoadhesive MTZ aqueous-based gel as described herein is applied for a number of applications sufficient to achieve any level of cure as defined in the FDA Guidance.

In some specific embodiments, the amount of high dosage mucoadhesive MTZ aqueous-based gel applied in a single application contains from about 60 mg to about 100 mg MTZ. In some specific embodiments, the amount of high dosage mucoadhesive MTZ aqueous-based gel applied in a single application contains from about 60 mg to about 80 mg, or from about 60 mg to about 70 mg, MTZ. In some specific embodiments, the amount of high dosage MTZ aqueous-based gel applied in a single application contains about 65 mg MTZ.

The frequency and duration of application can vary, and may depend upon the desired outcome. Generally, the gel is applied once per day for a period of one, two, three, four or five days. It has been found that significant therapeutic benefit is achieved with a single application of high dosage mucoadhesive MTZ aqueous-based gel containing about 65 mg MTZ. Accordingly, in some embodiments the gel is applied in a single application, i.e., in the absence of further application of the high dosage mucoadhesive MTZ aqueous-based gel. It has also been found that application of a high dosage mucoadhesive MTZ aqueous-based gel containing about 65 mg MTZ applied once per day for a period of five days yielded less incidence of BV recurrence than a similar course of treatment with FDA-approved 0.75 wt % metronidazole gel, and virtually no incidence of vulvovaginal candidiasis post therapy. Accordingly, in some embodiments the gel is applied once per day for a period of five days.

As used herein, the term "recurrence" means the reappearance of at least one of the symptoms of BV, as defined herein, following treatment with a high dosage MTZ gel described herein such that a subject is diagnosed, at least a second time, with BV following the conclusion of treatment.

A "decrease in the incidence of recurrence" means an increase in the time to recurrence of symptoms of BV following the conclusion of treatment with a high dosage MTZ gel described herein as compared to time to historical recurrence observed with conventional 0.75 wt % MTZ gels, such as METROGEL VAGINAL®). In specific embodiments, a decrease in the incidence of occurrence means that symptoms of BV are not observed for a period of at least about 19 days, for example 20 days, 21 days, 22 days, 23 days, 24 days, 25 days, 26 days, 27 days, 28 days, 29 days or more, following conclusion of treatment. No recurrence of symptoms of BV for a period of at least 29 days, for example, 30 days, 35 days, 40 days, 45 days, 50 days, 3 months, 6, months, 9 months, one year, or more, following the conclusion of treatment, suggests that there is no recurrence in a subject following conclusion of treatment.

A "decrease in the incidence of recurrence" can also be defined relative to a study population. For example, a treatment regimen with a high dosage mucoadhesive MTZ aqueous-based gel as described herein that yields a statistically significant number of fewer women who experience symptoms of BV at 20 or more days following treatment as compared to the number who report symptoms of BV at 20 or more days following treatment with conventional 0.75 wt % MTZ gels (such as, for example, METROGEL VAGINAL®)) is considered a decreased incidence of recurrence of BV.

For use, the high dosage mucoadhesive MTZ aqueous-based gels can be packaged in any form that is convenient for the desired mode of application. In specific embodiments useful for intravaginal application, the high dosage mucoadhesive MTZ aqueous-based gel is packaged in unit dosage form, as a specific example as a pre-filled, single dose syringe-type applicator.

6.5. Additional Non-Limiting Aspects

Additional non-limiting aspects of the high dosage mucoadhesive MTZ aqueous-based gel compositions and methods of using them to treat women suffering from and/or diagnosed with BV are provided below.

6.5.1. Methods

M1. A method of treating a subject suffering from and/or diagnosed with BV, comprising applying intravaginally to the subject a mucoadhesive aqueous-based gel comprising one or more mucoadhesive gelling polymers, about 1 wt % to about 2 wt % metronidazole (MTZ), and water, wherein the amount of mucoadhesive aqueous-based gel applied in a single application contains from about 60 mg to about 100 mg MTZ.

M2. The method of aspect M1, wherein the levels of MTZ from the mucoadhesive aqueous-based gel measured in the stratum corneum and receiver fluid in an in vitro Franz cell skin permeation experiment carried out with human cadaver skin are at least about 25-55-fold higher and at least about 1-20-fold lower, respectively, when normalized for concentration, than the MTZ levels measured from METROGEL VAGINAL®.

M3. The method of aspect M1, in which the mucoadhesive aqueous-based gel has a viscosity ranging from about 200,000 mPa to about 400,000 mPa, measured at 25° C. using the controlled shear rate method, a Bohlin CVO 100 rheometer and the rheometer settings of Table 11.

M4. The method of aspect M1, in which the mucoadhesive aqueous-based gel has a degree of mucoadhesion within about ±10% of that of MG33PB.

M5. The method of aspect M1, in which the mucoadhesive aqueous-based gel comprises about 30 wt % to about 60 wt % water.

M6. The method of aspect M1, in which the mucoadhesive aqueous-based gel is substantially free of dextrins, cyclodextrins, niacin, and niacinamide.

M7. The method of aspect M1 in which the mucoadhesive aqueous-based gel is stable for a period of at least 6 months at 25° C.

M8. The method of any one of aspects M1-M7 in which the mucoadhesive aqueous-based gel includes about 1 wt % to about 3 wt % total mucoadhesive gelling polymers and about 40-45 wt % of a solvent system for the MTZ.

M9. The method of aspect M8 in which the solvent system comprises one or more solvents having a saturated MTZ solubility at 25° C. of at least about 20 mg/g.

M10. The method of aspect M9 in which the solvent system comprises one or more solvents having a saturated MTZ solubility at 25° C. of at least about 50 mg/g and optionally one or more solvents having a saturated MTZ solubility at 25° C. in a range of about 20 mg/g to about 25 mg/g.

M11. The method of aspect M10 in which the solvent system comprises one or more lower aromatic alcohols and optionally one or more lower aliphatic diols and/or one or more polyoxyalkylenes having a molecular weight ranging from about 200 to about 400 ("lower polyoxyalkylene").

M12. The method of aspect M11 in which the solvent system comprises one or more lower aromatic alcohols, one or more lower aliphatic diols, and/or one or more lower polyoxyalkylenes.

M13. The method of aspect M12 in which the solvent system comprises one or more lower aromatic alcohols, one or more lower aliphatic diols, and one or more lower polyoxyalkylenes.

M14. The method of any one of aspects M11-M13 in which the one or more lower aromatic alcohols are selected from the group consisting of benzyl alcohol, phenoxyethanol, and mixtures thereof.

M15. The method of any one of aspects M11-M14 in which the one or more lower alkylene diols are selected from the group consisting of ethane-1,2-diol (ethylene glycol), propane-1,2-diol (propylene glycol), and mixtures thereof.

M16. The method of any one of aspects M11-M15 in which the one or more lower polyoxyalkylenes are selected from the group consisting of polyoxyethylene (polyethylene glycol), polyoxypropylene (polypropylene glycol), and mixtures thereof.

M17. The method of any one of aspects M11-M16 in which one or more lower aliphatic diols and the one or more lower polyoxyalkylenes are included in the solvent system in a total lower aliphatic diol to total lower polyoxyalkylene weight ratio ranging from about 1:1 to about 1:2.

M18. The method of any one of aspects M13-M17 in which the solvent system comprises about 3.5 wt % to about 5 wt % total lower aromatic alcohols, and about 95 wt % to about 95.5 wt % of a mixture of the one or more lower alkylene diols and the one or more lower polyoxyalkylenes.

M19. The method of aspect M18 in which the weight ratio of total lower alkylene diols to total lower polyoxyalkylenes ranges from about 1:1 to about 1:1.67.

M20. The method of any one of aspects M8-M19 in which the solvent system consists of benzyl alcohol, propane-1,2-diol and PEG 400.

M21. The method of any one of aspects M8-M20 in which the solvent system consists of about 3.5 wt % to about 5 wt % benzyl alcohol and about 95 wt % to about 96.5 wt % of a mixture of propane-1,2-diol and PEG 400, wherein the weight ratio of the propane-1,2-diol to PEG 400 ranges from about 1:1 to about 1:1.67.

M22. The method of any one of aspects M1-M21 in which the mucoadhesive aqueous-based gel further comprises one or more preservatives.

M23. The method of any one of aspects M1-M22 in which the one or more preservative is an ester of 4-hydroxy benzoic acid (a paraben).

M24. The method of aspect M23 in which the one or more preservatives are selected from the group consisting of methyl 4-hydroxybenzoate (methylparaben), propyl 4-hydroxybenzoate (propylparaben), and mixtures thereof.

M25. The method of any one of aspects M1-M23 in which the mucoadhesive aqueous-based gel has a pH in the range about pH 3.0 to about pH 5.0.

M26. The method of aspect M25 in which the mucoadhesive aqueous-based gel has a pH of about pH 4.0.

M27. The method of any one of aspects M1-M26 in which the one or more mucoadhesive gelling polymer is selected from the group consisting of a hydroxyethylcellulose, a carbomer, a polycarbophil, and mixtures thereof.

M28. The method of any one of aspects M1-M27 in which the amount of mucoadhesive aqueous-based gel applied in a single application contains about 65 mg MTZ.

M29. The method of any one of aspects M1-M28 in which the mucoadhesive aqueous-based gel includes about 1 wt % to about 1.5 wt % MTZ.

M30. The method of aspect M29 in which the mucoadhesive aqueous-based gel is applied once per day for a period of one to five days.

M31. The method of aspect M29 in which the mucoadhesive aqueous-based gel is applied once per day for a period of one day.

M32. The method of aspect M29 in which the mucoadhesive aqueous-based gel is applied once per day for a period of five days.

M33. The method of any one of aspects M1-M28 in which the mucoadhesive aqueous-based gel includes about 1.3 wt % MTZ.

M34. The method of aspect M33 in which the mucoadhesive aqueous gel-based is applied once per day for a period of one to five days.

M3 5. The method of aspect M3 3 in which the mucoadhesive aqueous-based gel is applied once per day for a period of one day.

M36. The method of aspect M33 in which the mucoadhesive aqueous gel is applied once per day for a period of five days.

M37. The method of any one of aspects M1-M7 in which the mucoadhesive aqueous-based gel comprises about 1.3 wt % MTZ, about 2 wt % polycarbophil AA-1, about 2 wt % benzyl alcohol, about 15 wt % propane-1,2-diol, about 25 wt % PEG 400, about 0.02 wt % methyl 4-hydroxybenzoate, and about 0.08 wt % propyl 4-hydroxybenzoate.

M3 8. The method of aspect M3 7 in which the mucoadhesive aqueous-based gel is applied once per day for a period of one to five days.

M39. The method of aspect M37 in which the mucoadhesive aqueous-based gel is applied once per day for a period of one day.

M40. The method of aspect M37 in which the mucoadhesive aqueous-based gel is applied once per day for a period of five days.

M41. The method of any one of aspects M37-M40 in which the amount of mucoadhesive aqueous-based gel applied in a single application contains about 65 mg MTZ.

M42. A method of treating a subject suffering from and/or diagnosed with BV, comprising applying intravaginally to the subject an amount of an aqueous-based gel for a number of applications sufficient to achieve a clinical cure, wherein the aqueous-based gel comprises one or more mucoadhesive polymers, about 1.3 wt % MTZ, and water, and has one or more features or characteristics selected from the following group:
 (a) the levels of MTZ from the mucoadhesive aqueous-based gel measured in the stratum corneum and receiver fluid in an in vitro Franz cell skin permeation experiment carried out with human cadaver skin are at least about 25-55-fold higher and at least about 1-20-fold lower, respectively, when normalized for concentration, than the MTZ levels measured from METROGEL VAGINAL®;
 (b) a viscocity ranging from about 200,000 mPa to about 400,000 mPa, measured at 25° C. using the controlled shear rate ramp method, a Bohlin CVO 100 rheometer and the rheometer settings of Table 11;
 (c) a degree of mucoadhesion within about ±10% of that of MG33PB;
 (d) comprises about 30 wt % to about 60 wt % water;
 (e) is substantially free of dextrins, cyclodextrins, niacin and niacinamide;
 (f) is stable for a period of at least 6 months at 25° C.; and
 (g) includes about 1 wt % to about 3 wt % total mucoadhesive polymers and about 40-45 wt % of a solvent system for the MTZ.

M43. The method of aspect M42 in which an amount of the aqueous-based gel is applied for a number of applications sufficient to achieve a therapeutic cure.

M44. A method of treating a woman suffering from and/or diagnosed with BV, comprising applying intravaginally to the woman a single application of a mucoadhesive MTZ aqueous-based gel comprising about 1.3% by weight MTZ, about 1% to about 2% weight of one or more mucoadhesive gelling polymers, about 40% to about 50% weight of a solvent system for the MTZ, and about 50% to about 55% by weight water, where the solvent system comprises about 3% to about 5% by weight of one or more solvents having a saturated MTZ solubility at 25° C. of at least about 50 mg/g and about 95% to about 97% by weight of one or more solvents that collectively have a saturated MTZ solubility at 25° C. in the range of about 20 mg/g to about 25 mg/g, and wherein the amount of the mucoadhesive MTZ aqueous-based gel applied contains about 60 mg to about 100 mg MTZ.

M45. The method of aspect M44 in which the amount of mucoadhesive MTZ aqueous-based gel applied contains about 65 mg MTZ.

M46. The method of any one of aspects M43-M45 in which the one or more solvents having a saturated MTZ solubility at 25° C. of at least about 50 mg/g is benzyl alcohol.

M47. The method of any one of aspects M43-M46 in which the one or more solvents that collectively have a saturated MTZ solubility at 25° C. in the range of about 20 mg/g to about 25 mg/g are each selected from the group consisting of a lower aliphatic diol and a lower polyoxyalkylene.

M48. The method of any one of aspects M43-M47 in which the solvent system comprises about 3% to about 5% by weight benzyl alcohol and about 95% to about 97% by weight of a mixture of a lower aliphatic diol and a lower polyoxyalkylene, where the weight ratio of the lower aliphatic diol to lower polyoxyalkylene is in the range of about 1:1 to about 1:2.

M49. The method of aspect M48 in which the weight ratio of the lower aliphatic diol to the lower polyoxyalkylene is about 1:1.67.

M50. The method of any one of aspects M48-M49 in which the lower aliphatic diol is propane-1,2-diol and the lower polyoxyalkylene is PEG 400.

M51. The method of any one of aspects M43-M50 in which the one or more mucoadhesive gelling polymers are each selected from the group consisting of a cross-linked acrylic acid polymer and a cellulosic polymer.

M52. The method of any one of aspects M43-M51 in which the one or more mucoadhesive gelling polymers are each selected from the group consisting of a carbomer and a polycarbophil.

M53. The method of any one of aspects M43-M52 in which the one or more mucoadhesive gelling polymer is a polycarbophil.

M54. The method of any one of aspects M43-M53 in which the mucoadhesive MTZ aqueous-based gel comprises about 1.3% by weight MTZ, about 2% by weight polycarbophil AA-1, about 2% by weight benzyl alcohol, about 15% by weight propane-1,2-diol, about 25% by weight PEG 400, about 0.1% by weight of one or more preservatives, and about 54.6% by weight water.

M55. The method of M54 in which the one or more preservatives are each a paraben.

M56. The method of aspect M55 in which the one or more preservatives are methylparaben and propylparaben.

M57. The method of any one of aspects M43-M56 in which the mucoadhesive MTZ aqueous-based gel comprises about 1.3% by weight MTZ, about 2% by weight polycarbophil AA-1, about 2% by weight benzyl alcohol, about 15% by weight propane-1,2-diol, about 25% by weight PEG 400, about 0.08% by weight methylparaben, about 0.02% by weight propylparaben, and about 54.6% by weight water.

M58. A method of treating a subject suffering from and/or diagnosed with BV with a single application of a composition suitable therefor, comprising applying intravaginally to the subject a mucoadhesive aqueous-based gel comprising one or more mucoadhesive gelling polymers, water, and about 1.3 wt % MTZ, wherein the amount of mucoadhesive aqueous-based gel applied in the single application contains about 65 mg of MTZ; and the single application is sufficient to treat or cure the BV in the complete or substantial absence of further treatments or applications.

M59. A method of treating a subject suffering from and/or diagnosed with BV, comprising applying intravaginally to the subject a single administration of a mucoadhesive aqueous-based MTZ gel, wherein the mucoadhesive aqueous-based MTZ gel comprises one or more mucoadhesive gelling polymers, about 1.3% by weight MTZ, and water, and the amount of mucoadhesive aqueous-based gel applied in the single administration contains about 65 mg MTZ.

M60. A method of treating a subject suffering from and/or diagnosed with BV, comprising applying intravaginally to the subject a mucoadhesive aqueous-based MTZ gel, wherein (i) the mucoadhesive aqueous-based MTZ gel comprises one or more mucoadhesive gelling polymers, about 1.3% by weight MTZ, and water, (ii) the amount of the mucoadhesive aqueous-based MTZ gel applied contains about 65 mg MTZ, and (iii) the mucoadhesive aqueous-based MTZ gel is applied a single time without further applications.

M61. A method of treating a subject suffering from and/or diagnosed with BV, comprising applying intravaginally to the subject a mucoadhesive aqueous-based MTZ gel, wherein (i) the mucoadhesive aqueous-based MTZ gel comprises one or more mucoadhesive gelling polymers, about 1.3% by weight MTZ and water, (ii) the amount of the mucoadhesive aqueous-based gel applied in a single application contains about 65 mg MTZ, and (iii) the mucoadhesive aqueous-based MTZ gel is applied once per day for a total of one day.

M62. A method of treating a subject suffering from and/or diagnosed with BV, comprising applying intravaginally to the subject a mucoadhesive aqueous-based MTZ gel at least once a day for a period of 5 total days, wherein (i) the mucoadhesive aqueous-based MTZ gel comprises one or more mucoadhesive gelling polymers, about 1.3% by weight MTZ, and water, and (ii) the amount of the mucoadhesive aqueous-based MTZ gel applied in a single application contains about 65 mg MTZ.

M63. A method of treating a subject suffering from and/or diagnosed with BV, comprising applying intravaginally to the subject a single application of an amount of a mucoadhesive aqueous-based MTZ gel sufficient to cure the BV, wherein the mucoadhesive aqueous-based MTZ gel comprises one or more mucoadhesive gelling polymers, about 1.3% by weight MTZ, and water.

M64. The method of any one of aspects M58-M63 in which the mucoadhesive aqueous-based MTZ gel is a gel according to any one of aspects C1-C32, below.

6.5.2. Compositions

C1. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and water, where the levels of MTZ from the mucoadhesive aqueous-based gel measured in the stratum corneum and receiver fluid in an in vitro Franz cell skin permeation experiment carried out with human cadaver skin are at least about 25-55-fold higher and at least about 1-20-fold lower, respectively, when normalized for concentration, than the MTZ levels measured from METROGEL VAGINAL®.

C2. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and water, wherein the mucoadhesive aqueous-based gel has a viscosity ranging from about 200,000 mPa to about 400,000 mPa, measured at 25° C. using the controlled shear rate method, a Bohlin CVO 100 rheometer and the rheometer settings off able 11.

C3. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and water, wherein the mucoadhesive aqueous-based gel has a degree of mucoadhesion within about ±10% of that of MG33PB.

C4. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and about about 30 wt % to about 60 wt % water.

C5. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and water, wherein the mucoadhesive aqueous-based gel is substantially free of dextrins, cyclodextrins, niacin and niacinamide, and optionally also surfactants.

C6. A mucoadhesive aqueous-based gel comprising about 1 wt % to about 2 wt % MTZ, about 1 wt % to about 3 wt % of one or more mucoadhesive gelling polymers, about 30 wt % to about 60 wt % of a solvent system for the MTZ, and water, wherein the mucoadhesive aqueous-based gel is stable for a period of at least 6 months at 25° C.

C7. The gel of any one of aspects C1-C6 in which the mucoadhesive aqueous-based gel includes about 1 wt % to about 3 wt % total mucoadhesive gelling polymer and about 40-45 wt % of a solvent system for the MTZ.

C8. The gel of aspect C7 in which the solvent system comprises one or more solvents having a saturated MTZ solubility at 25° C. of at least about 20 mg/g.

C9. The gel of aspect C8 in which the solvent system comprises one or more solvents having a saturated MTZ solubility at 25° C. of at least about 50 mg/g and optionally one or more solvents having a saturated MTZ solubility at 25° C. in a range of about 20 mg/g to about 25 mg/g.

C10. The gel of aspect C9 in which the solvent system comprises one or more lower aromatic alcohols, and optionally one or more lower aliphatic diols and/or one or more polyoxyalkylenes having a molecular weight ranging from about 200 to about 400 ("lower polyoxyalkylene").

C11. The gel of aspect C10 in which the solvent system comprises one or more lower aromatic alcohols, one or more lower aliphatic diols, and/or one or more lower polyoxyalkylenes.

C12. The gel of aspect C11 in which the solvent system comprises one or more lower aromatic alcohols, one or more lower aliphatic diols, and one or more lower polyoxyalkylenes.

C13. The gel of any one of aspects C10-C12 in which the one or more lower aromatic alcohols are selected from the group consisting of benzyl alcohol, phenoxyethanol, and mixtures thereof.

C14. The gel of any one of aspects C10-C13 in which the one or more lower alkylene diols are selected from the group consisting of ethane-1,2-diol (ethylene glycol), propane-1,2-diol (propylene glycol), and mixtures thereof.

C15. The gel of any one of aspects C10-C14 in which the one or more lower polyoxyalkylenes are selected from the group consisting of polyoxyethylene (polyethylene glycol), polyoxypropylene (polypropylene glycol), and mixtures thereof.

C16. The gel of any one of aspects C10-C15 in which one or more lower aliphatic diols and the one or more lower polyoxyalkylenes are included in the solvent system in a total lower aliphatic diol to total polyoxyalkylene weight ratio ranging from about 1:1 to about 1:2.

C17. The gel of any one of aspects C10-C16 in which the solvent system comprises about 3.5 wt % to about 5 wt % total lower aromatic alcohols and about 95 wt % to about 95.5 wt % of a mixture of the one or more lower alkylene diols and the one or more lower polyoxyalkylenes.

C18. The gel of aspect C17 in which the weight ratio of total lower alkylene diols to total lower polyoxyalkylenes is about 1:1.67.

C19. The gel of any one of aspects C10-C18 in which the solvent system consists of benzyl alcohol, propane-1,2-diol and PEG 400.

C20. The gel of any one of aspects C10-C19 in which the solvent system consists of about 3.5 wt % to about 5 wt % benzyl alcohol and about 95 wt % to about 96.5 wt % of a mixture of propane-1,2-diol and PEG 400, wherein the weight ratio of the propane-1,2-diol to PEG 400 ranges from about 1:1.67 to about 1:1.

C21. The gel of any one of aspects C1-C20 which further comprises one or more preservatives.

C22. The gel of any one of aspects C1-C21 in which the one or more preservative is an ester of 4-hydroxy benzoic acid (a paraben).

C23. The gel of aspect C22 in which the one or more preservatives are selected from the group consisting of methyl 4-hydroxybenzoate (methylparaben), propyl 4-hydroxybenzoate (propylparaben), and mixtures thereof.

C24. The gel of any one of aspects C1-C23 which t has a pH in the range about pH 3.0 to about pH 5.0.

C25. The gel of aspect C24 which has a pH of about pH 4.0.

C26. The gel of any one of aspects C1-C25 in which the one or more mucoadhesive gelling polymers are selected from the group consisting of a hydroxyethylcellulose, a carbomer, a polycarbophil, and mixtures thereof.

C27. The gel of any one of aspects C1-C6 in which the mucoadhesive aqueous-based gel comprises about 1.3 wt % MTZ, about 2 wt % polycarbophil AA-1, about 2 wt % benzyl alcohol, about 15 wt % propane-1,2-diol, about 25 wt % PEG 400, about 0.02 wt % methyl 4-hydroxybenzoate, and about 0.08 wt % propyl 4-hydroxybenzoate.

C28. A mucoadhesive aqueous-based gel comprising about 1.3 wt % MTZ, about 1 wt % to about 3 wt % of one or more mucoadhesive gelling polymesr and about 40 wt % to about 45 wt % of a solvent system for the MTZ, where the solvent system comprises benzyl alcohol, propane-1,2-diol, and PEG 400 and wherein the gel is stable for a period of 18 months when stored at a temperature in the range of about 25° C. to about 40° C.

C29. The gel of aspect C28 in which the one or more mucoadhesive gelling polymers are selected from the group consisting of cross-linked acrylic acid polymers and cellulosic polymers.

C30. The gel of aspect C29 in which the cross-linked acrylic acid polymers are selected from the group consisting of carbomers and polycarbophils.

C31. The gel of any one of aspects C29-C30 in which the cellulosic polymers are selected from the group consisting of hydroxyethyl cellulose, hydroxypropyl cellulose, and hydroxypropyl methyl cellulose.

C32. The gel of any one of aspects C29-C31 which comprises about 2 wt % total mucoadhesive gelling polymers.

6.5.3. Uses

U1. The use of a mucoadhesive aqueous-based gel according to any one of aspects C1-C32 for the treatment of a woman suffering from and/or diagnosed with BV.

U2. The use of aspect U1 in which the mucoadhesive aqueous-based gel is applied intravaginally for a number of applications sufficient to yield a bacteriological cure, a clinical cure, or a therapeutic cure.

U3. The use according to any one of aspects U1-U2 in which the amount of mucoadhesive aqueous-based gel applied in a single application contains about 60 mg to about 100 mg MTZ.

U4. The use of any one of aspects U1-U3, in which the amount of mucoadhesive aqueous-based gel applied in a single application contains about 65 mg MTZ.

U5. The use of any one of aspects U1-U4, in which the mucoadhesive aqueous-based gel is applied intravaginally once per day for a period of from one to five days.

U6. The use of any one of aspects U1-U5, in which the mucoadhesive aqueous-based gel is applied intravaginally once per day for a period of one day.

U7. The use of any one of aspects U1-U5, in which the mucoadhesive aqueous-based gel is applied once per day for a period of five days.

6.5.4. Unit Dosage Forms

D1. A unit dosage form of a high dosage mucoadhesive MTZ aqueous-based gel suitable for intravaginal application, comprising an amount of a gel according to any one of aspects C1-C32 containing about 65 mg to about 100 mg MTZ packaged in a container suitable for intravaginal application.

D2. The unit dosage form of aspect D1 which includes an amount of a gel containing about 65 mg MTZ.

Unless otherwise defined, all technical and scientific terms used herein have the same meaning as commonly understood by one of ordinary skill in the art to which the various inventions described herein belong. Although methods and materials similar or equivalent to those described herein can be used in the practice or testing of the disclosed inventions, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

7. EXAMPLES

Having now generally described the inventions of the disclosure, the same will be more readily understood through reference to the following Examples, which are provided by way of illustration, and are not intended to limit the scope of the inventions described herein.

Example 1: Exemplary Solvents Useful for Solvent Systems The solubility of MTZ in a variety of solvents at 25° C. was determined to identify solvents useful for solubilizing MTZ at the concentrations required for the high dosage mucoadhesive MTZ aqueous-based gels described herein. The saturated MTZ solubility at 25° C. of a number of solvents are provided in Table 1, below. Solvent systems useful for preparing high dosage mucoadhesive MTZ aqueous-based gels having desired concentrations of MTZ can be devised using these saturated solubilities for guidance. Additional solvents suitable for use with these (and other) solvents for preparing high dosage mucoadhesive MTZ aqueous-based gels as described herein may be readily identified based upon their saturated MTZ solubilities. The saturated MTZ solubility at 25° C. in a number of solvent systems that have been mixed with an aqueous phase that are suitable for preparing high dosage mucoadhesive MTZ aqueous-based gels are provided in Table 2, below.

TABLE 1

|  | Solubility at 25° C. (mg/g) (n = 3, mean ± SEM) | Solubility at 25° C. (mg/g) (n = 1) |
| --- | --- | --- |
| Benzyl alcohol |  | 72.69 |
| 2 wt % aq. Benzyl alcohol | 10.81 ± 0.040 |  |
| Deionized water | 8.70 ± 0.09 | 9.37 |
| Ethanol | 16.36 ± 0.12 | 19.96 |
| Ethylene glycol |  | 21.34 |
| Glycerol |  | 8.35 |
| 50 wt % aq. glycerol | 7.62 ± 0.19 |  |
| Propylene glycol | 18.62 ± 0.25 | 20.74 |
| PEG 400 | 18.79 ± 1.23 | 24.78 |
| Phosphate buffer, 50 mM, pH 4 | 8.26 ± 0.45 | 9.09 |
| Phosphate buffer, 50 mM, pH 5 |  | 9.13 |
| Phosphate buffer, 50 mM, pH 6 | 8.57 ± 0.05 | 9.10 |
| Phosphate buffer, 50 mM, pH 7 |  | 9.07 |
| tetraglycol |  | 29.65 |
| 10 wt % aq. Lutrol ® FI27 | 9.15 ± 0.09 |  |
| 1 wt % aq. polysorbate 60 | 9.72 ± 0.08 |  | prepared and subjected to a variety of different homogeneity, rheological, stability, biological and clinical tests as described in later examples. All gels were prepared using a similar process, described below.

Preparation of Gels. Required amounts of preservative(s), for example methyl paraben and propyl paraben, were weighed into a Duran® bottle followed by the aqueous phase (phosphate buffer or deionized water). The contents were thoroughly mixed to dissolve the preservatives. The remaining solvents (e.g., benzyl alcohol, ethanol, propylene glycol and PEG 400) were weighed into a separate Duran® bottle and mixed thoroughly followed by the required amount of metronidazole. The Duran® bottle was then placed in a water bath at 55° C. and stirred continuously until the metronidazole dissolved. The Duran® bottle was removed from the water bath, placed at room temperature and mixing was continued until the solution equilibrated to room temperature. The preservative solution was then added to the MTZ solution under constant stirring. The required amount of gelling agent was weighed into a weighing boat and added to the above solution under constant stirring and stirred until the gelling agent fully hydrated. Care was taken to mix the contents thoroughly to ensure homogeneity.

For gels utilizing pH-sensitive or dependent gelling polymer, the pH of the MTZ solution can be adjusted to value within the optimal range for gelling prior to adding the gelling polymer, and the pH of the gel adjusted as need thereafter.

Preparation of Placebo Gels. In several Experiments discussed herein, placebo gels are used as comparators or as controls. Placebo gels were prepared as described above. For the placebos, the MTZ was omitted and replaced with an equivalent wt % of water or buffer, depending upon the aqueous phase used for the active gel.

Preparation of Phosphate Buffer pH 4. Disodium hydrogen phosphate dihydrate (3.9 g) is weighed into a 500 ml Duran® bottle and 450 ml of deionized water is added. The solution is mixed thoroughly to dissolve the buffer salt. The pH of the solution is adjusted to pH 4 using o-phosphoric acid and made up to volume with deionized water in a 500 ml volumetric flask.

The composition of various exemplary gels containing 1.5 wt % MTZ, 2.0 wt %, 1.3 wt % and 1.18% MTZ are provided in Tables 3, 4, 5 and 6, respectively, below.

TABLE 2

Saturated MTZ Solubility at 25° C. of Solvent Mixtures

|  | 3 | 4 | 5 | 6 | 7 | 18 | 19 | 20 | 21 | 22 | 23 | 24 |
| --- | --- | --- | --- | --- | --- | --- | --- | --- | --- | --- | --- | --- |
| Benzyl alcohol | 5.00 | — | — | 2.00 | — | 1.50 | 1.50 | 1.50 | 1.50 | 1.00 | 1.00 | 1.00 |
| Propylene glycol | 20.0 | 20.0 | 20.0 | 15.0 | — | 10.0 | 20.0 | 20.0 | 20.0 | 20.0 | 20.0 | 20.00 |
| PEG 400 | 20.0 | 20.0 | 20.0 | 25.0 | — | 20.0 | 20.0 | 20.0 | 20.0 | 20.0 | 20.0 | 20.00 |
| ethanol | — | 10.0 | 20.0 | — | — | — | — | — | — | — | — | — |
| Polysorbate 60 | — | — | — | — | — | — | — | — | 1.00 | — | — | — |
| Lutrol ® F127 | — | — | — | — | — | — | — | — | — | 10.0 | — | 10.00 |
| glycerol | — | — | — | — | — | — | — | — | — | — | — | — |
| β-HPC | — | — | — | — | 20.0 | — | — | — | — | — | — | — |
| Deionized water | — | — | — | — | 8.00 | — | — | — | — | — | — | — |
| Phosphate buffer, 50 mM, pH 4 | 55.0 | 50.0 | 40.0 | 58.0 | — | 68.5 | 58.5 | 57.5 |  | 59.0 | 58.0 | 49.00 |
| MTZ solubility (% w/w) | 1.56 | 1.30 | 0.94 | 1.57 | 1.75 | 1.25 | 1.49 | 1.52 | 1.57 | 1.40 | 1.34 | 1.46 |

Example 2: Exemplary High Dosage Mucoadhesive MTZ Aqueous-Based Gels

A number of exemplary high dosage mucoadhesive MTZ aqueous-based gels containing different quantities of MTZ and utilizing a variety of different solvent systems were prepared and subjected to a variety of different homogeneity, Formulations MG03, MG04, MG08 and MG09 listed in Table 3 formed clear thick pale yellow colored gels while MG26 formed a white cream gel. An ideal pH for the Carbomers, polycarbophil AA-1 and Carbomer 974P, to form a gel is neutral. Because the desired pH of gels for intravaginal application is approximately pH 4, high amounts of these gelling agents were used as compared to HEC. MG03 contained β-hydroxypropyl cyclodextrin as a solubilizing agent.

TABLE 3

Exemplary Gels Containing 1.5 wt % MTZ Composition (% w/w)

| | MG03 | MG04 | MG08 | MG09 | MG26 |
|---|---|---|---|---|---|
| Metronidazole | 1.50 | 1.50 | 1.50 | 1.50 | 1.50 |
| β-Hydroxypropyl-cyclodextrin | 20.00 | — | — | — | — |
| Purified Water | 76.70 | 51.70 | 49.45 | 48.45 | 42.00 |
| HEC(HHX) | 1.80 | 1.80 | — | — | — |
| Polycarbophil AA-1 | — | — | 3.00 | 5.00 | — |
| Carbomer 974P | — | — | 1.00 | — | 1.00 |
| EDTA, disodium salt | — | — | 0.05 | 0.05 | — |
| Octyldodecanol | — | — | — | 10.00 | — |
| Benzyl alcohol | — | 5.00 | 5.00 | 5.00 | 5.00 |
| Propylene glycol | — | 20.00 | 20.00 | 20.00 | 20.00 |
| Polyethylene glycol | — | 20.00 | 20.00 | 20.00 | 20.00 |

TABLE 4

Exemplary Gels Containing 2 wt % MTZ Composition (% w/w)

| | MG18 | MG21 | MG23 | MG24 |
|---|---|---|---|---|
| Metronidazole | 2.00 | 2.00 | 2.00 | 2.00 |
| Purified Water | 39.95 | 51.00 | 48.95 | 41.45 |
| HEC(HHX) | — | 1.00 | — | — |
| Polycarbophil AA-1 | 3.00 | — | 3.00 | 1.50 |
| EDTA, disodium salt | 0.05 | — | 0.05 | 0.05 |
| Lutrol ® F127 | 10.00 | — | — | 10.00 |
| Tween ® 60 | — | 1.00 | 1.00 | — |
| Benzyl alcohol | 5.00 | 5.00 | 5.00 | 5.00 |
| Propylene glycol | 20.00 | 20.00 | 20.00 | 20.00 |
| Polyethylene glycol 400 | 20.00 | 20.00 | 20.00 | 20.00 |

TABLE 5

Exemplar Gels Containing 1.3 wt % MTZ Composition (% w/w)

| | MG3 | MG3 | MG3 | MG3 | MG3 | MG3 | MG3 | MG3 | MG3 | MG3 | MG3 | MG37 |
|---|---|---|---|---|---|---|---|---|---|---|---|---|
| Metronidazole | 1.30 | 1.30 | 1.30 | 1.30 | 1.30 | 1.30 | 1.30 | 1.30 | 1.30 | 1.30 | 1.30 | 1.30 |
| Purified Water | — | — | 54.70 | 54.60 | 54.70 | 54.60 | 1.30 | 1.30 | 55.20 | 55.10 | 55.20 | 55.10 |
| Phosphate buffer pH4 | 54.90 | 54.80 | — | — | — | — | 55.40 | 55.30 | — | — | — | — |
| HEC(HHX) | 1.80 | 1.80 | — | — | — | — | 1.80 | 1.80 | — | — | — | — |
| Polycarbophil AA-1 | — | — | 2.00 | 2.00 | — | — | — | — | 2.00 | 2.00 | — | — |
| Carbomer 974P | — | — | — | — | 2.00 | 2.00 | — | — | — | — | 2.00 | 2.00 |
| Methyl paraben | — | 0.08 | — | 0.08 | — | 0.08 | — | 0.08 | — | 0.08 | — | 0.08 |
| Propylparaben | — | 0.02 | — | 0.02 | — | 0.02 | — | 0.02 | — | 0.02 | — | 0.02 |
| Benzyl alcohol | 2.00 | 2.00 | 2.00 | 2.00 | 2.00 | 2.00 | 1.50 | 1.50 | 1.50 | 1.50 | 1.50 | 1.50 |
| Propylene glycol | 15.00 | 15.00 | 15.00 | 15.00 | 15.00 | 15.00 | 20.00 | 20.00 | 20.00 | 20.00 | 20.00 | 20.00 |
| Polyethylene glycol 400 | 25.00 | 25.00 | 25.00 | 25.00 | 25.00 | 25.00 | 20.00 | 20.00 | 20.00 | 20.00 | 20.00 | 20.00 |

TABLE 6

Exemplar Gels Containing 1.18 wt % MTZ Composition (% w/w)

| | MG42 | MG43 | MG44 |
|---|---|---|---|
| Metronidazole | 1.18 | 1.18 | 1.18 |
| Purified Water | 41.82 | 41.72 | 42.32 |
| HEC(HHX) | — | — | 0.90 |
| Polycarbophil AA-1 | 1.40 | — | 0.70 |
| Carbomer 974P | — | 1.50 | — |
| Lutrof F127 | 10.90 | 10.90 | 10.70 |
| Benzyl alcohol | 1.10 | 1.10 | 1.10 |
| Propylene glycol | 21.80 | 21.80 | 21.50 |
| Polyethylene glycol 400 | 21.80 | 21.80 | 21.60 |

Example 3: Mucoadhesive Properties of the Exemplary Gels

The mucoadhesive properties of two exemplary high dosage mucoadhesive MTZ gels (MG32PB and MG33PB) were tested using two different methods: adherence to isolated porcine gastric mucosa and rheological measurements in the presence and absence of mucin. The methods and results are described below.

a. Mucoadhesion Using Isolated Porcine Gastric Mucosa

Methods. For the experiments, a small section (15×10 cm) of fresh porcine gastric mucosa was mounted on a slope at 10° angle and rinsed with pH 4 buffer for 10 min with the aid of a peristaltic pump. A small aliquot (50 μl) of test gel was spread on the mucosal membrane at the top of the slope and left for 10 min. The pump was then switched on and buffer collected after t=1, 2, 3, 4, 5, 10 and 15 min into individual vials at each time point. A blank sample without any test gel was also analyzed for any background or interference. The samples were filtered through 0.45 μm PVDF syringe filters and analyzed by HPLC. The rate of loss of MTZ from the mucosal membrane was plotted against time for each test gel and the resultant data compared to determine the relative mucoadhesion of each test gel. A second experiment was also performed with sampling time points of 15 s intervals over 5 min.

Results. The data are shown in FIGS. 1 and 2. The results show that MG32PB has marginally better mucoadhesivity than MG33PB as determined by the amount of metronidazole remaining on the mucosa at each time point.

b. Rheological Measurements

Methods. Mucin was weighed into a glass vial followed by the gel under investigation. A magnetic follower was placed in the sample and the sample mixed until all the mucin hydrated. Rheological parameters of the test gel with and without mucin were analysed using an oscillation experiment (Bohlin CVO rheometer). An amplitude sweep followed by a frequency sweep using corresponding placebo gels without mucin was initially carried out to determine the linear viscoelastic region. The parameters used to determine the frequency sweep for the gels are given in Table 7.

TABLE 7

Rheometer Settings For Determining Frequency Sweep

| Parameter | Setting |
|---|---|
| Measurement type/diameter | Parallel plate/40 mm |
| Gap size | 1000 μm |
| Temperature mode | Isothermal 25° C. |
| Thermal equilibration time | 60 s |
| Shear mode | Controlled stress |
| Stress | Fixed at 4 Pa |
| Frequency sweep range | 5-20 Hz |
| Frequency increment step | 0.15 Hz |

Test gel (about 1 g) was placed on the bottom plate of the rheometer fitted with a parallel plate. The lower plate was raised so as to trap the sample in the pre-determined gap. The sample was then subjected to a series of sinusoidal oscillations from 5 to 20 Hz in 0.15 Hz increments. The applied torque (4 Pa) was previously determined to be in the linear viscoelastic region for both the highest and the lowest frequency. Each gel was tested three times. At the end of each run, Bohlin computer software (version 6.50.5.7) was used to determine G', the elastic or storage modulus. The data obtained for each parameter was plotted as a function of frequency and the mean values of G' calculated at a fixed frequency of 10 Hz. Using the mean G' value of the active gel with mucin compared to the mean G' value of the active gel without mucin, the ΔG' and log ratio of G' with and without mucin were calculated.

Results. Addition of mucin, which is also a polymer, increased the elastic modulus of the test gels as determined by ΔG' (Table 8). It is assumed that a higher value for log G' ratio correlates to more interaction with mucin and therefore better mucoadhesion. However, this increase could be dependent on the inherent interaction between the gelling polymer used for the preparation of gel and mucin. The log G' ratio, which is the ratio of log G' of the test gel with and without mucin gives an insight into the increase of viscoelastic nature of the formulation.

TABLE 8

Mucoadhesion of Exemplary Gels MG32PB and MG33PB (determined by the effect of mucin on gel)

| | ΔG' | | Log G' ratio | |
|---|---|---|---|---|
| Gel | 1$^{st}$ run (n = 1) | 2$^{nd}$ run (n = 3) | 1$^{st}$ run (n = 1) | 2$^{nd}$ run (n = 3) |
| MG32PB | 265.80 | 228.27 ± 13.35 | 0.049 | 0.041 ± 0.002 |
| MG33PB | 150.65 | 173.59 ± 34.02 | 0.025 | 0.31 0.006 |

Example 4: Short-Term Shelf Stability of the Exemplary Gels

Various different embodiments of exemplary high dosage mucoadhesive MTZ aqueous-based gels were tested for short-term (4 week) shelf stability at 25° C. and 45° C. Gels were stored in Vindon Scientific stability cabinets in sealed amber vials. Parameters tested included homogeneity (visual and microscopic observation for presence of crystals and/or particulates), MTZ stability, preservative efficacy, viscosity and pH. The stability time points tested were t=0, 2 and 4 weeks at 25±2° C. at 60±5% RH and 40±2° C. at 75±5% RH. Placebo gels without MTZ were also stored for the same duration and assessed for physical and chemical stability.

To access MTZ stability, MTZ was extracted from the gel and analyzed by HPLC Method 1 (parameters in Table 9, below). For the extraction, approximately 0.5 g gel was placed in a 50 mL volumetric flask. Approximately 30 mL of HPLC mobile phase 65:35 methanol/60 mM phosphate buffer (prepared as below) was added and the mixture vortexed until the gel was observed to have dispersed into solution. The solution was made up to volume with HPLC mobile phase. For HPLC analysis, an aliquot was filtered through a 0.45 μm PTFE syringe filter, discarding the first 2 ml. The remaining filtrate was analyzed by HPLC Method 1.

TABLE 9

| HPLC Method 1 | |
|---|---|
| HPLC System | Waters 2695D Alliance HPLC System |
| | Waters 996 Photo-diode array detector |
| | Waters Empower Data processing Software (version 5.00.00.00) |
| Column | Zorbax C8 5 μm, 250 × 4.6 mm |
| Guard Column | Zorbax C8 5 μm 20 × 3.9 mm guard column |
| Detection | 254 nm |
| Sample Temperature | 25° C. |
| Column Temperature | 25° C. |
| Flow Rate | 1 ml/min |
| Mobile Phase | 65:35 methanol/60 mM phosphate buffer |
| Injection Volume | 20 μl |
| Run Time | 10 min |
| Needle Wash | 65:35 methanoPwater |
| Pump Wash | 60:40 methanoPwater |

To prepare the mobile phase, 1.5 g sodium phosphate monobasic and 1.3 g sodium phosphate dibasic were weighed into a Duran® bottle and dissolved in 350 ml deionized water. The solution was mixed thoroughly, 650 ml methanol added, the resultant solution mixed thoroughly with a magnetic stirrer and filtered through a 0.22 μm filter.

For the HPLC analysis, the MTZ peak (retention time approx. 3.312 min at 254 nm detection) was integrated and compared to a control sample. The amount of MTZ remaining after storage was quantified as a percentage of the theoretical concentration (TC) at t=0. The measured concentration (MC) was determined using a calibration curve obtained with MTZ stock solutions of known concentrations (prepared by serial dilution of a 1 mg/ml stock).

The physical stability of the gels was assessed using light microscopy (Leica DME SOP 3091). The test gel was compared to a corresponding placebo control gel to assess the presence of particulates.

Results. The percentage of MTZ recovered from the gels is provided in Table 10 below. MTZ was stable in all gels at all concentrations tested. A low recovery was observed in MG37PB, MG42PB and MG43PB from the 4 week 25° C. samples. However, the recovery from the same gels stored at 40° C. was 100%, suggesting a possible extraction/weighing error for the 25° C. samples. The % peak purity for all samples was 100%.

TABLE 10

4-Week Short-Term Stability of Exemplary Gels at 25° C. and 40° C. (n = 3, mean ± SD)

Percentage Recovery of MTZ Compared to Control

| | t = 0 | t = 2 wk 25° C. | t = 2 wk 40 | t = 4 wk 25 | t = 4 wk 40 |
|---|---|---|---|---|---|
| MG32-1.3% | 103.20 ± 0.66 | n/a | 100.53 ± 0.17 | n/a | 101.12 ± 0.36 |
| MG33-1.3% | 105.04 ± 0.35 | n/a | 100.74 ± 0.32 | n/a | 100.98 ± 0.31 |
| MG34-1.3% | 103.33 ± 0.64 | n/a | 100.73 ± 0.10 | n/a | 101.64 ± 0.43 |
| MG35-1.3% | 102.54 ± 0.09 | n/a | 100.86 ± 0.36 | n/a | 101.18 ± 0.31 |
| MG36-1.3% | 103.49 ± 1.17 | n/a | 101.09 ± 0.68 | n/a | 101.01 ± 0.64 |
| MG37-1.3% | 103.46 ± 0.64 | n/a | 94.15 ± 5.88 | n/a | 101.14 ± 0.15 |
| MG42-1.18% | 102.99 ± 1.72 | n/a | 92.44 ± 0.18 | n/a | 101.58 ± 0.80 |
| MG43-1.18% | 102.70 ± 0.81 | n/a | 92.64 ± 0.99 | n/a | 101.30 ± 0.77 |
| MG44-1.18% | 103.39 ± 0.56 | n/a | 98.34 ± 4.17 | n/a | 101.27 ± 0.50 |
| MG03-1.5% | 104.76 ± 0.48 | 106.48 ± 1.01 | 105.86 ± 1.37 | n/a * | 105.78 ± 0.86 |
| MG04-1.5% | 104.74 ± 0.48 | 105.45 ± 2.28 | 104.09 ± 0.50 | 106.27 ± 0.13 | 106.01 ± 0.34 |
| MG08-1.5% | 101.31 ± 2.67 | 99.02 ± 1.35 | 98.39 ± 0.78 | 100.40 ± 1.28 | 98.43 ± 0.81 |
| MG26-1.5% | 104.51 ± 0.56 | 103.34 ± 0.52 | 103.97 ± 1.26 | 104.45 ± 0.23 | 103.97 ± 1.11 |
| MG18-2.0% | 102.42 ± 0.96 | 103.51 ± 0.38 | 104.21 ± 1.00 | 104.71 ± 0.63 | 104.94 ± 0.23 |
| MG21-2.0% | 103.67 ± 0.52 | 104.81 ± 0.63 | 105.46 ± 0.66 | 106.40 ± 0.11 | 106.00 ± 0.17 |
| MG23-2.0% | 104.95 ± 0.52 | 106.18 ± 0.47 | 106.35 ± 1.34 | 107.38 ± 0.23 | 105.78 ± 0.98 |
| MG24-2.0% | 103.07 ± 0.41 | 102.78 ± 0.24 | 105.50 ± 1.39 | 105.21 ± 0.39 | 103.92 ± 1.19 |

* Sample not analyzed due to microbial growth

Example 5: Long-Term Shelf Stability of the Exemplary Gels

Various different embodiments of exemplary high dosage mucoadhesive MTZ aqueous-based gels were tested for long-term stability, at 25° C. and 40° C.

For the study, 20 g of each test gel was stored in a sealed vial at 25±2° C./60±5% RH and 40±2° C./75±5% RH. Back-up samples were also stored at −20° C., 2-8° C. and 30° C./65% RH for analysis upon failure of either real or accelerated time samples. Corresponding placebo gels without MTZ were stored along with the test gels.

Gels were removed from the storage cabinets after 1, 2, 3, 6, 12 and 18 months and tested for physical and chemical stability using microscopic analysis and viscosity analysis, as described below.

Microscopic analysis. Gels were viewed under a light microscope (Leica® DME). A small sample of the gel was placed onto a microscope slide using a micro-spatula. The microscope slide was covered with a cover glass and the gel viewed using the 40× objective. Active gels were compared to placebo gels for the presence of crystals.

If crystals were observed, the particle size was measured using the scale on a calibrated graticule (Olympus,® Objective Micrometer, 0.01 mm). The microscope was set up so that the camera (Nikon Cool Pix® 4500 digital camera) was attached to the relay lens of the microscope and the 40× objective lens was set into place to view the sample. Camera settings: Image size: 1280×960 pixels, Image quality: Fine. Once a clear distinct view was obtained, pictures were taken (×400 magnification).

Viscosity Analysis. The rheology of the gels was measured at each time point (t=0, 1, 2, 3, 6, 12 and 18 months). A cone and plate measurement system is preferable for flow curve measurements as the shear rate is constant across the diameter of the truncated cone. Accordingly, a controlled shear rate ramp method was employed. A point on the flow curves at a shear rate of $0.16^{s-1}$ was used to compare each gel and the viscosity determined. The rheometer settings used are in Table 11 below:

TABLE 11

Rheometer settings for the controlled shear rate ramp

| | |
|---|---|
| Measurement type/diameter | Cone and plate/4°/40 mm |
| Gap size | 150 μm |
| Shear rate range | From 0.001-1.0 s−1 |
| Duration shear rate | 180 s |
| Progression of shear rate | Linear |
| Temperature of sample | 25° C. ± 0.1° C. |
| Isothermal conditions | Measurements forced to wait until sample at temperature, time out after 900 s |
| Thermal equilibration time | 0 s once temperature was 25° C. ± 0.1 before first measurements were made. |

Gels were also tested for MTZ content, benzyl alcohol content, paraben content, preservative efficacy and pH. With the exception of the 18 mos samples, the MTZ content was accessed as described above for the short-term stability samples. For the 18 mos samples, MTZ content was assessed as described below.

For the extraction, 0.5 g±20 mg of gel was weighed into a 25 ml volumetric flask and diluted with approximately 20 ml of sample diluient (3:7 methanol/10 mM $KH_2PO_4$). The mixture was vortexed until the gel dispersed into solution (approximately 5 min). The solution was brought to volume with sample diluents and vortex mixed for approximately 1 minute. Approximately 14 ml of the sample was centrifuged at 3500 rpm for 10 min., the resultant supernatant filtered through a 0.45 μm PTFE syringe filter, discarding the first 2 ml. The remaining filtrate was analyzed by HPLC Method 2 (parameters in Table 12, below). In addition to MTZ, the recovery of benzyl alcohol, methyl paraben and propyl paraben was also determined.

TABLE 12

HPLC Method 2

| | |
|---|---|
| HPLC System | Waters 2695 Alliance HPLC System |
| | Waters 2996 Photo-Diode Array Detector |
| | Waters Empower Data Processing Software (version 6.10.01.00) |
| Column | Phenomenex luna C18(2) 5 μm, 250 × 4.6 mm lot number 479 458-61 |
| Guard Column | Phenomenex Security guard C18, 4 × 3 mm |
| Detection | 254 nm |
| Sample Temperature | 25 ± 2° C. |
| Column Temperature | 25 ± 2° C. |
| Flow Rate | 1 mL/min |
| Mobile Phase | Mobile phase A: 0.01M potassium dihydrogen phosphate dihydrate |
| | Mobile phase B: 100% methanol |

| Gradient | Time (min) | Mobile phase A (%) | Mobile phase B (%) |
|---|---|---|---|
| | 0 | 80 | 20 |
| | 10 | 80 | 20 |
| | 18 | 28 | 72 |
| | 22 | 28 | 72 |
| | 23 | 80 | 20 |
| | 28 | 80 | 20 |

| | |
|---|---|
| Injection Volume | 10 μl |
| Run Time | 28 min |
| MTZ Retention Time | 9.0 min |
| Needle Wash | 60:40 methanol (HPLC grade):deionized water (MilliQ 18.2 MO) |
| Pump Wash | 60:40 methanol (HPLC grade):deionized water (MilliQ 18.2 MO) |

Preservative efficacy testing was carried out in a manner consistent with the EP and US Pharmacopeia specifications. Inoculated samples were tested at t=0 h, 24 h, 48 h, 7 days, 14 days, 21 days and 28 days.

Gels corresponding to MG33PB but including reduced quantities of preservatives were tested for preservative efficacy. The test gels, Table 13, below, were prepared as described in Example 2.

TABLE 13

Composition of Variants of MG33PB

| | MG33 (75%) | MG33 (90%) |
|---|---|---|
| MTZ | 1.1700 | 1.170 |
| Purified water | 54.940 | 55.255 |
| Polycarbophil AA-1 | 2.000 | 2.000 |
| Methyl paraben | 0.072 | 0.060 |
| Propyl paraben | 0.018 | 0.015 |
| Benzyl alcohol | 1.800 | 1.500 |
| Propylene glycol | 15.000 | 15.000 |
| PEG 400 | 25.000 | 25.000 |

Placebo versions of gels MG33 (75%) and MG33 (90%) were also prepared.

pH testing was carried out at t=0, 1, 2, 3, 6, 12 and 18 months.

Results. Table 14 shows the % recovery of MTZ from the gels. The percentage recovery of MTZ from the gels stored at 25° C. and 40° C. for 6 months is comparable to t=0 data. The % peak purity for all the gels is found to be 100%, indicating that MTZ is stable in all the gels tested. The percentage recovery of MTZ from MG33PB and MG32PB stored at 25° C. and 40° C. for 18 months is comparable to t=0 data.

TABLE 14

Stability of Exemplary Gels at 25° C. and 40° C.
Data show % recovery of MTZ from the gel (n = 3, mean ± SEM)

| T (months) | MG32PB | MG33PB | MG34PB | MG35PB | MG36PB | MG37PB |
|---|---|---|---|---|---|---|
| t = 0* | 102.68 ± 0.25 | 102.68 ± 0.26 | 102.07 ± 0.21 | 102.15 ± 0.16 | 101.97 ± 0.53 | 102.68 ± 0.15 |
| t = 1 m 25° C. | 102.19 ± 0.16 | 102.12 ± 0.06 | 101.91 ± 0.23 | 103.13 ± 0.38 | 101.91 ± 0.15 | 101.95 ± 0.09 |
| t = 1 m 40° C. | 102.48 ± 0.06 | 101.3840.18 | 101.50 ± 0.13 | 104.12 ± 0.37 | 101.26 ± 0.20 | 101.85 ± 0.22 |
| t = 2 m 25° C. | 101.9 ± 0.11 | 101.55 ± 0.11 | 101.98 ± 0.13 | 102.29 ± 0.18 | 101.82 ± 0.13 | 102.43 ± 0.20 |
| t = 2 m 40° C. | 101.65 ± 0.35 | 99.59 ± 0.85 | 99.82 ± 0.60 | 101.60 ± 0.20 | 100.61 ± 0.56 | 100.64 ± 0.52 |
| t = 3 m 25° C. | 100.87 ± 0.31 | 100.44 ± 0.04 | 100.83 ± 0.33 | 102.20 ± 0.41 | 101.36 ± 0.04 | 102.02 ± 0.10 |
| t = 3 m 40° C. | 100.70 ± 0.11 | 98.96 ± 0.79 | 98.09 ± 0.44 | 99.7 ± 0.07 | 97.36 ± 0.18 | 98.55 ± 0.05 |
| t = 6 m 25° C. | 101.684 ± 0.5 | 100.87 ± 0.50 | 101.68 ± 0.25 | 101.26 ± 0.11 | 100.77 ± 0.29 | 102.57 ± 0.11 |
| t = 6 m 40° C. | 100.97 ± 0.67 | 101.13 ± 0.42 | 99.87 ± 0.30 | 101.08 ± 0.35 | 99.40 ± 0.37 | 100.46 ± 0.22 |
| t = 12 m 25° C. | n/a | 101.15 ± 0.23 | n/a | n/a | n/a | n/a |
| t = 12 m 40° C. | n/a | 98.25 ± 0.07 | n/a | n/a | n/a | n/a |
| t = 18 m 25° C. | 103.53 ± 2.42 | 99.91 ± 0.77 | n/a | n/a | n/a | n/a |
| t = 18 m 40° C. | 99.85 ± 0.28 | 98.03 ± 1.69 | n/a | n/a | n/a | n/a |

*% recovery at t = 0 was performed n = 6 ± SEM for homogeneity

Physical stability of metronidazole gel formulations. Gels placed at 25° C. and 40° C. were visually and microscopically assessed for the presence of any particulates or crystals after 6 months. Although the gels were observed to be physically stable, there was a small change in color from a very pale yellow to pale yellow in all active gels after 6 months of storage at 40° C. This was absent in the corresponding placebo formulations (Table 17). Small differences in pH were observed in storage. However, no large shift in pH was observed in the active gels, indicating the gels are stable (Table 15) after 6 months.

Flow curves were used to measure the viscosity of the gels. The point on the flow curves at which the viscosities of the gels were compared is at a shear rate of $0.16\ s^{-1}$ (Table 11). After the readings (n=2) were taken at t=0, the curves were examined and a point of comparison selected. All of gels exhibited pseudoplastic behavior or shear thinning, i.e., as the shear rate increased, the viscosity decreased. As the shear rate is increased the instantaneous viscosity of the gels became more and more similar to each other such that there was no longer a marked difference between the viscosities of each gel. A point on the curve was chosen for comparison between the gels where all of the flow curves are different. The viscosity was calculated using the interpolation of the two closest shear rates above and below $0.16^{s-1}$. All gels after 6 months storage at 25° C. and MG33PB at 25° C. up to 18 months were observed to show small variability in viscosity, generally constant between each time point up to 18 months (Table 16). At 40° C. storage, a drop in viscosity was observed, however this was more significant for the placebo gels than the active gels.

The back-up active gels stored at 2-8° C. for 6 months were also inspected for crystal formation, as were placebo gels stored under the same conditions as their corresponding best gels. Large crystals were observed in gels MG32PB and MG35PB. Large sheet like crystals also formed gels MG33PB and MG36PB. A single small crystal formed in gels MG34PB and MG37PB. These data indicate that storage at 2-8° C. is not recommended for the high dosage mucoadhesive MTZ aqueous-based gels. Storage at 25° C. or 40° C. is more suitable, as crystal formulation was not observed at these temperatures.

Observations of the physical appearance of placebo and test formulations stored for 6 mos at 25° C. and 40° C. is provided in Table 17, below.

TABLE 15 pH of Exemplary Gels Stored at 25° C. and 40° C.

| Formulation (Placebos) | t = 0 | t = 1 | | t = 2 m | | t = 3 m | | t = 6 m | | t = 12 m | | t = 18 m | |
|---|---|---|---|---|---|---|---|---|---|---|---|---|---|
| | | 25° C. | 40° C. | 25° C. | 40° C. | 25° C. | 40° C. | 25° C. | 40° C. | 25° C. | 40° C. | 25° C. | 40° C. |
| MG32PB | 5.1 | 4.9 | 5.2 | 5.2 | 5.0 | 5.0 | 4.9 | 5.1 | 4.8 | n/a | n/a | 5.2 | 5.1 |
| MG33PB | 3.9 | 3.8 | 3.9 | 3.9 | 3.8 | 3.7 | 3.7 | 3.8 | 3.8 | 4.1 | 3.8 | 3.9 | 3.9 |
| MG34PB | 4.0 | 3.8 | 3.9 | 4.0 | 3.9 | 3.7 | 3.8 | 3.8 | 3.9 | n/a | n/a | n/a | n/a |
| MG35PB | 5.1 | 5.1 | 5.0 | 5.2 | 4.9 | 5.1 | 4.9 | 5.0 | 4.9 | n/a | n/a | n/a | n/a |
| MG36PB | 3.8 | 3.7 | 3.7 | 3.9 | 3.7 | 3.5 | 3.5 | 3.6 | 3.6 | n/a | n/a | n/a | n/a |
| MG37PB | 3.8 | 3.7 | 3.6 | 3.6 | 3.8 | 3.5 | 3.5 | 3.6 | 3.6 | n/a | n/a | n/a | n/a |

| Formulation (Actives) | t = 0 | t = 1 m | | t = 2 m | | t = 3 m | | t = 6 m | | t = 12 m | | t = 18 m | |
|---|---|---|---|---|---|---|---|---|---|---|---|---|---|
| | | 25° C. | 40° C. | 25° C. | 40° C. | 25° C. | 40° C. | 25° C. | 40° C. | 25° C. | 40° C. | 25° C. | 40° C. |
| MG32PB | 5.1 | 5.1 | 5.1 | 5.2 | 5.1 | 5.1 | 5.1 | 5.1 | 5.0 | n/a | n/a | 5.2 | 5.1 |
| MG33PB | 3.9 | 4.0 | 3.9 | 4.2 | 3.9 | 3.8 | 4.0 | 4.1 | 4.0 | 4.2 | 4.3 | 5.0 | 4.4 |
| MG34PB | 4.0 | 4.1 | 4.0 | 4.1 | 4.1 | 3.7 | 3.9 | 3.9 | 4.0 | n/a | n/a | n/a | n/a |
| MG35PB | 5.2 | 4.9 | 5.1 | 5.3 | 5.2 | 5.2 | 5.1 | 5.1 | 5.1 | n/a | n/a | n/a | n/a |
| MG36PB | 4.0 | 3.9 | 3.9 | 4.1 | 4.0 | 3.7 | 3.7 | 4.0 | 4.1 | n/a | n/a | n/a | n/a |
| MG37PB | 4.0 | 3.9 | 4.0 | 4.1 | 3.9 | 3.8 | 3.9 | 4.1 | 4.0 | n/a | n/a | n/a | n/a |

TABLE 16

Viscosity of Exemplary Gels Stored at 25° C. and 40° C.

| Time (months) | MG32PB | | MG33PB | | MG34PB | | MG35PB | | MG36PB | | MG37PB | |
|---|---|---|---|---|---|---|---|---|---|---|---|---|
| | Placebo | Active | Placebo | Active | Placebo | Active | Placebo | Active | Placebo | Active | Placebo | Active |
| Viscosity (mPas) at 25° C. | | | | | | | | | | | | |
| t = 0 | 299907 | 285766 | 263415 | 316624 | 333411 | 415236 | 287357 | 292432 | 308055 | 291714 | 324138 | 371399 |
| t = 1 | 309065 | 325695 | 270402 | 294917 | 334730 | 375060 | 290940 | 300019 | 271073 | 274503 | 251456 | 339551 |
| t = 2 | 331546 | 263264 | 273861 | 287725 | 333193 | 376395 | 291295 | 268178 | 267250 | 276140 | 231617 | 359769 |
| t = 3 | 311637 | 294178 | 259886 | 276503 | 315363 | 372616 | 305701 | 297965 | 243066 | 258491 | 212763 | 336410 |
| t = 6 | 258433 | 250116 | 261494 | 308102 | 328419 | 374120 | 242216 | 298475 | 247567 | 275626 | 219261 | 337051 |
| t = 12 | n/a | n/a | 215339 | 235108 | n/a | n/a | n/a | n/a | n/a | n/a | n/a | n/a |
| t = 18 | 275223 | 293346 | 194215 | 219741 | n/a | n/a | n/a | n/a | n/a | n/a | n/a | n/a |
| Viscosity (mPas) at 40° C. | | | | | | | | | | | | |
| t = 0 | 299907 | 285766 | 263415 | 316624 | 333411 | 415236 | 287357 | 292432 | 308055 | 291714 | 324138 | 371399 |
| t = 1 | 319774 | 280639 | 361158 | 263315 | 329030 | 360147 | 301443 | 280435 | 305288 | 261720 | 206307 | 335181 |
| t = 2 | 305906 | 242894 | 367321 | 259016 | 376333 | 356693 | 277249 | 243496 | 364213 | 258584 | 287505 | 334457 |
| t = 3 | 281581 | 276653 | 298214 | 253704 | 349430 | 316822 | 256484 | 280481 | 272173 | 219989 | 239640 | 307145 |
| t = 6 | 179966 | 228019 | 254421 | 241973 | 284824 | 315104 | 183874 | 216715 | 191400 | 231610 | 178624 | 280642 |

TABLE 16-continued

Viscosity of Exemplary Gels Stored at 25° C. and 40° C.

| Time (months) | MG32PB Placebo | MG32PB Active | MG33PB Placebo | MG33PB Active | MG34PB Placebo | MG34PB Active | MG35PB Placebo | MG35PB Active | MG36PB Placebo | MG36PB Active | MG37PB Placebo | MG37PB Active |
|---|---|---|---|---|---|---|---|---|---|---|---|---|
| t = 12 | n/a | n/a | 115088 | 187612 | n/a | n/a | n/a | n/a | n/a | n/a | n/a | n/a |
| t = 18 | 57878 | 199306 | 139706 | 198759 | n/a | n/a | n/a | n/a | n/a | n/a | n/a | n/a |

TABLE 17

Physical Appearance of Placebo and Test Gels Stored for 6 Months at 25° C. and 40° C.

| | | Visual appearance (25° C.) | | | | |
|---|---|---|---|---|---|---|
| | | t = 0 | t = 1 m | t = 2 m | t = 3 m | t = 6 m |
| Placebo Gels | MG32PB | Clear gel of high viscosity | Clear gel of high viscosity | Clear gel of high viscosity | Clear gel of high viscosity | Clear gel of high viscosity |
| | MG33PB | Very slightly turbid gel of high viscosity | Slightly turbid gel of high viscosity | Slightly turbid gel of high viscosity | Slightly turbid gel of high viscosity | Slightly turbid gel of high viscosity |
| | MG34PB | Very slightly turbid gel of high viscosity | Slightly turbid gel of high viscosity | Slightly turbid gel of high viscosity | Slightly turbid gel of high viscosity | Slightly turbid gel of high viscosity |
| | MG35PB | Very slightly turbid gel of high viscosity | Slightly turbid gel of high viscosity | Slightly turbid gel of high viscosity | Slightly turbid gel of high viscosity | Slightly turbid gel of high viscosity |
| | MG36PB | Very slightly turbid gel of high viscosity | Slightly turbid gel of high viscosity | Slightly turbid gel of high viscosity | Slightly turbid gel of high viscosity | Slightly turbid gel of high viscosity |
| | MG37PB | Very slightly turbid gel of high viscosity | Slightly turbid gel of high viscosity | Slightly turbid gel of high viscosity | Slightly turbid gel of high viscosity | Slightly turbid gel of high viscosity |
| Test Gels | MG32PB | Very pale yellow clear gel of high viscosity | Very pale yellow clear gel of high viscosity | Very pale yellow clear gel of high viscosity | Very pale yellow clear gel of high viscosity | Very pale yellow clear gel of high viscosity |
| | MG33PB | Very pale yellow very slightly turbid gel of high viscosity | Very pale yellow slightly turbid gel of high viscosity | Very pale yellow slightly turbid gel of high viscosity | Very pale yellow slightly turbid gel of high viscosity | Very pale yellow slightly turbid gel of high viscosity |
| | MG34PB | Very pale yellow very slightly turbid gel of high viscosity | Very pale yellow slightly turbid gel of high viscosity | Very pale yellow slightly turbid gel of high viscosity | Very pale yellow slightly turbid gel of high viscosity | Very Pale yellow slightly turbid gel of high viscosity |
| | MG35PB | Very pale yellow very slightly turbid gel of high viscosity | Very pale yellow slightly turbid gel of high viscosity | Very pale yellow slightly turbid gel of high viscosity | Very pale yellow slightly turbid gel of high viscosity | Very Pale yellow slightly turbid gel of high viscosity |
| | MG36PB | Very pale yellow very slightly turbid gel of high viscosity | Very pale yellow slightly turbid gel of high viscosity | Very pale yellow slightly turbid gel of high viscosity | Very pale yellow slightly turbid gel of high viscosity | Very Pale yellow slightly turbid gel of high viscosity |
| | MG37PB | Very pale yellow very slightly turbid gel of high viscosity | Very pale yellow slightly turbid gel of high viscosity | Very pale yellow slightly turbid gel of high viscosity | Very pale yellow slightly turbid gel of high viscosity | Very Pale yellow slightly turbid gel of high viscosity |

| | | Visual appearance (40° C.) | | | | |
|---|---|---|---|---|---|---|
| | | t = 0 | t = 1 m | t = 2 m | t = 3 m | t = 6 m |
| Placebo Gels | MG32PB | Clear gel of high viscosity | Clear gel of high viscosity | Clear gel of high viscosity | Clear gel of high viscosity | Clear gel of high viscosity |
| | MG33PB | Very slightly turbid gel of high viscosity | Slightly turbid gel of high viscosity | Slightly turbid gel of high viscosity | Slightly turbid gel of high viscosity | Slightly turbid gel of high viscosity |
| | MG34PB | Very slightly turbid gel of high viscosity | Slightly turbid gel of high viscosity | Slightly turbid gel of high viscosity | Slightly turbid gel of high viscosity | Slightly turbid gel of high viscosity |

TABLE 17-continued

Physical Appearance of Placebo and Test Gels Stored for 6 Months at 25° C. and 40° C.

|  |  |  |  |  |  |  |
|---|---|---|---|---|---|---|
|  | MG35PB | Very slightly turbid gel of high viscosity | Slightly turbid gel of high viscosity | Slightly turbid gel of high viscosity | Slightly turbid gel of high viscosity | Slightly turbid gel of high viscosity |
|  | MG36PB | Very slightly turbid gel of high viscosity | Slightly turbid gel of high viscosity | Slightly turbid gel of high viscosity | Slightly turbid gel of high viscosity | Slightly turbid gel of high viscosity |
|  | MG37PB | Very slightly turbid gel of high viscosity | Slightly turbid gel of high viscosity | Slightly turbid gel of high viscosity | Slightly turbid gel of high viscosity | Slightly turbid gel of high viscosity |
| Test Gels | MG32PB | Very pale yellow clear gel of high viscosity | Very pale yellow clear gel of high viscosity | Very pale yellow clear gel of high viscosity | Very pale yellow clear gel of high viscosity | Pale yellow clear gel of high viscosity |
|  | MG33PB | Very pale yellow slightly turbid gel of high viscosity | Very pale yellow slightly turbid gel of high viscosity | Very pale yellow slightly turbid gel of high viscosity | Very pale yellow slightly turbid gel of high viscosity | Pale yellow slightly turbid gel of high viscosity |
|  | MG34PB | Very Pale yellow slightly turbid gel of high viscosity | Very Pale yellow slightly turbid gel of high viscosity | Very pale yellow slightly turbid gel of high viscosity | Very pale yellow slightly turbid gel of high viscosity | Pale yellow slightly turbid gel of high viscosity |
|  | MG35PB | Very Pale yellow slightly turbid gel of high viscosity | Very Pale yellow slightly turbid gel of high viscosity | Very pale yellow slightly turbid gel of high viscosity | Very pale yellow slightly turbid gel of high viscosity | Pale yellow slightly turbid gel of high viscosity |
|  | MG36PB | Very Pale yellow slightly turbid gel of high viscosity | Very Pale yellow slightly turbid gel of high viscosity | Very pale yellow slightly turbid gel of high viscosity | Very pale yellow slightly turbid gel of high viscosity | Pale yellow slightly turbid gel of high viscosity |
|  | MG37PB | Very Pale yellow slightly turbid gel of high viscosity | Very Pale yellow slightly turbid gel of high viscosity | Very pale yellow slightly turbid gel of high viscosity | Very pale yellow slightly turbid gel of high viscosity | Pale yellow slightly turbid gel of high viscosity |

PET testing results for 12-month MG33PB stored at 40° C. The results of the preservative efficacy tests (PET) are summarized in Table 18 and Table 19. Gel MG33PB stored for 12 months at 40° C. meets the required log reductions against all organisms tested as specified by the European Pharmacopeia 6.3.

TABLE 18

Inoculation size for each organism applied to test Gels

| Organism | Stock (Cfu/ml) | Final theoretical concentration in each formulation (Cfu/ml) |
|---|---|---|
| S. aureus | $3.1 \times 10^8$ | $3.1 \times 10^6$ |
| E. coli | $2.1 \times 10^8$ | $2.1 \times 10^6$ |
| Ps. aeruginosa | $1.3 \times 10^8$ | $1.3 \times 10^6$ |
| C. albicans | $1.1 \times 10^7$ | $1.1 \times 10^5$ |
| A. niger | $1.5 \times 10^7$ | $1.5 \times 10^5$ |

TABLE 19

Recovery of organisms from MG33PB stored for 12 months at 40° C.

|  |  | Cfu/ml of organisms recovered | | | | | | |
|---|---|---|---|---|---|---|---|---|
|  | Organism | 0 h | 24 h | 48 h | 7 days | 14 days | 21 days | 28 days |
| MG33PB | S. aureus | $8.0 \times 10^2$ | $0.0 \times 10^0$ | $0.0 \times 10^0$ | $0.0 \times 10^0$ | $0.0 \times 10^0$ | $0.0 \times 10^0$ | $0.0 \times 10^0$ |
|  | E. coli | $2.7 \times 10^3$ | $0.0 \times 10^0$ | $0.0 \times 10^0$ | $0.0 \times 10^0$ | $0.0 \times 10^0$ | $0.0 \times 10^0$ | $0.0 \times 10^0$ |
|  | Ps. | $1.9 \times 10^3$ | $0.0 \times 10^0$ | $0.0 \times 10^0$ | $0.0 \times 10^0$ | $0.0 \times 10^0$ | $0.0 \times 10^0$ | $0.0 \times 10^0$ |
|  | C albicans | $2.7 \times 10^4$ | $4.0 \times 10^2$ | $0.0 \times 10^0$ | $0.0 \times 10^0$ | $0.0 \times 10^0$ | $0.0 \times 10^0$ | $0.0 \times 10^0$ |
|  | huger | $1.9 \times 10^5$ | $8.0 \times 10^0$ | $0.0 \times 10^0$ | $0.0 \times 10^0$ | $0.0 \times 10^0$ | $0.0 \times 10^0$ | $0.0 \times 10^0$ |

Analysis of 12-month with 6-month additional ambient storage and 18-month samples using validated analytical method 2. The sample stored for 12 months at 25° C. was stored for an additional 6 months at ambient temperature and the 18-month samples stored at 25° C. and 40° C. conform to the specification criteria for MTZ and preservatives content (Table 20 and Table 21)

TABLE 20

MTZ Recovered from MG33PB Stored for 18 Mos

| | Recovery (% w/w) (mean ± SEM, n = 3) t = 12 month 25° C. * | Target Conc. (% w/w) | Specification (% w/w) | Comments |
|---|---|---|---|---|
| Metronidazole | 1.291 ± 0.024 | 1.30% | 1.235-1.365% | Conforms |
| Benzyl Alcohol | 2.017 ± 0.039 | 2.00% | 1.900-2.100% | Conforms |
| Methyl paraben | 0.084 ± 0.002 | 0.08% | 0.076-0.084% | Conforms |
| Propyl paraben | 0.021 ± 0.000 | 0.02% | 0.019-0.021% | Conforms |

* t = 12 month samples stored at 25° C. for 12 months and an additional 6 months at ambient temperature (controlled between 15-30° C.).

TABLE 21

MTZ, Benzyl Alcohol, Methyl Paraben and Propyl Paraben Recovered from MG33PB after 18 Mos Storage at 25° C. and 40° C.

| MG33PB | recovery (% w/w) (mean ± SEM, n = 3) Active t = 18 25° C. | recovery (% w/w) (mean ± SEM, n = 3) Active t = 18 m 40° C. | recovery (% w/w) (i = 1) Placebo t = 18 m 25° C. | recovery (% w/w) (i = 1) Placebo t = 18 m 40° C. | Target Conc. (% w/w) | Specification (% w/w) | Comments |
|---|---|---|---|---|---|---|---|
| Metronidazole | 1.296 ± 0.006 | 1.243 ± 0.022 | n/a | 2.008 | 1.30% | 1.235-1.365% | Conforms |
| Benzyl Alcohol | 2.029 ± 0.010 | 1.979 ± 0.037 | 2.045 | 2.008 | 2.00% | 1.900-2.100% | Conforms |
| Methyl paraben | 0.084 ± 0.000 | 0.078 ± 0.001 | 0.083 | 0.084 | 0.08% | 0.076-0.084% | Conforms |
| Propylparaben | 0.02 ± 0.000 | 0.020 ± .001 | 0.21 | 0.21 | 0.02% | 0.019-0.021% | Conforms |

Effect of 75 and 90% w/w preservatives composition on MG33PB. The results for the PET test carried out with variants of exemplary gel MG33PB containing reduced quantities of preservatives, MG33 (75%) and MG33 (90%) are summarized in Table 22 and Table 23. MG33 (70%) and MG33 (90%) conform to the required log reductions against all organisms tested as specified by the European Pharmacopeia 6.3.

TABLE 22

Inoculation Size for Each Organism Applied to Test Gels

| Organism | Stock (Cfu/ml) | Final theoretical concentration in each formulation (Cfu/ml) |
|---|---|---|
| S. aureus | $2.0 \times 10^8$ | $2.0 \times 10^6$ |
| E. coli | $3.3 \times 10^8$ | $3.3 \times 10^6$ |
| Ps. aeruginosa | $3.8 \times 10^8$ | $3.8 \times 10^6$ |
| C. albicans | $1.8 \times 10^8$ | $1.8 \times 10^6$ |
| A.niger | $1.5 \times 10^8$ | $1.5 \times 10^6$ |

TABLE 23

Recovery of organisms from MG33 (75%) and MG33 (90%) after 0, 24 and 48 h and 7, 14, 21 and 28 days

| Formulation | Organism | 0 h | 24 h | 48 h | 7 days | 14 days | 21 days | 28 days |
|---|---|---|---|---|---|---|---|---|
| MG33 (75%) | S. aureus | $8.7 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | E. coli | $1.2 \times 10^6$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | Ps. | $6.0 \times 10^4$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | C. albicans | $3.6 \times 10^6$ | $5.3 \times 10^5$ | $0.0 \times 10^0$ | $0.0 \times 10^0$ | $0.0 \times 10^0$ | $0.0 \times 10^0$ | $0.0 \times 10^0$ |
| | A. niger | $2.5 \times 10^4$ | $2.9 \times 10^4$ | $1.3 \times 10^5$ | $0.0 \times 10^0$ | $0.0 \times 10^0$ | $0.0 \times 10^0$ | $0.0 \times 10^0$ |
| MG33 (90%) | S. aureus | $6.9 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | E. coli | $8.5 \times 10^4$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | Ps. | $2.3 \times 10^4$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | C. albicans | $3.2 \times 10^6$ | $4.1 \times 10^4$ | $0.0 \times 10^0$ | $0.0 \times 10^0$ | $0.0 \times 10^0$ | $0.0 \times 10^0$ | $0.0 \times 10^0$ |
| | A. niger | $2.9 \times 10^5$ | $3.6 \times 10^1$ | $1.0 \times 10^0$ | $0.0 \times 10^0$ | $0.0 \times 10^0$ | $0.0 \times 10^0$ | $0.0 \times 10^0$ |

TABLE 23-continued

Recovery of organisms from MG33 (75%) and MG33 (90%) after 0, 24 and 48 h and 7, 14, 21 and 28 days

| Formulation | Organism | 0 h | 24 h | 48 h | 7 days | 14 days | 21 days | 28 days |
|---|---|---|---|---|---|---|---|---|
| MG33 (75%) Placebo | S. aureus | $1.9 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | E. coli | $3.4 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | Ps. | $1.8 \times 10^4$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | C. albicans | $6.1 \times 10^5$ | $6.1 \times 10^3$ | $0.0 \times 10^0$ | $0.0 \times 10^0$ | $0.0 \times 10^0$ | $0.0 \times 10^0$ | $0.0 \times 10^0$ |
| | A. niger | $3.1 \times 10^5$ | $3.9 \times 10^4$ | $2.0 \times 10^0$ | $0.0 \times 10^0$ | $0.0 \times 10^0$ | $0.0 \times 10^0$ | $0.0 \times 10^0$ |
| MG33 (90%) Placebo | S. aureus | $5.6 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | E. coli | $3.6 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | Ps. | $3.5 \times 10^5$ | $0.0 \times 10^0$ | $0.0 \times 10^0$ | $0.0 \times 10^0$ | $0.0 \times 10^0$ | $0.0 \times 10^0$ | $0.0 \times 10^0$ |
| | C. albicans | $5.0 \times 10^5$ | $2.2 \times 10^5$ | $0.0 \times 10^0$ | $0.0 \times 10^0$ | $0.0 \times 10^0$ | $0.0 \times 10^0$ | $0.0 \times 10^0$ |
| | A. niger | $4.0 \times 10^5$ | $3.6 \times 10^5$ | $1.4 \times 10^0$ | $0.0 \times 10^0$ | $0.0 \times 10^0$ | $0.0 \times 10^0$ | $0.0 \times 10^0$ |

Example 6: Local Delivery and Skin Penetration Properties of the Exemplary Gels The in vitro skin permeation properties of several exemplary high degree mucoadhesive MTZ aqueous-based gels were tested in a Franz cell with a full thickness of human abdominoplasty skin obtained with informed consent. For the studies, all subcutaneous fat was removed with a scalpel and the skin was mounted in-between the donor and receiver compartments.

For the experiment, $^{14}C$ radiolabeled MTZ gels were prepared as described in Example 2 with the quantities of ingredients listed in Table 24, below. In Table 24, all quantities are in mg, which the exception of $^{14}C$-labeled MTZ, which is in μl.

stirring. MTZ (75 mg) was added and stirring continued until all the drug had dissolved. $^{14}C$-labeled MTZ stock solution (465 μl) was then added while stirring.

Carbomer phase: Disodium EDTA (5.03 mg) was weighed into a 28 ml glass vial to which purified water (5.698 g) was added. A magnetic flea was used to stir the formulation until all the disodium EDTA was fully dissolved. Carbomer 974P (200.89 mg) was added and the formulation left stirring overnight to allow the polymer to hydrate.

Combination: The paraben phase was added to the carbomer phase while stirring. The paraben phase was rinsed into the carbomer phase using water (200 mg). The gel was left overnight to cool to room temperature.

TABLE 24

Exact composition of Radio Labelled MTZ formulations

| | MG32PB | MG33PB | MG34PB | MG35PB | MG36PB | MG37PB |
|---|---|---|---|---|---|---|
| Metronidazole | 130.57 | 130.40 | 129.38 | 129.79 | 129.49 | 131.07 |
| $^{11}C$-labeledMTZ (μl) | 465 | 465 | 465 | 465 | 465 | 465 |
| Purified Water | — | 4999.24 | 5007.60 | — | 5049.89 | 5059.36 |
| Phosphate buffer pH 4 | 5013.41 | — | — | 5066.56 | — | — |
| Hydroxyethylcellulose (HHX) | 181.25 | — | — | 180.54 | — | — |
| Polycarbophil AA-1 | — | 200.96 | — | — | 201.23 | — |
| Carbomer 974P | — | — | 205.17 | — | — | 202.52 |
| Methyl paraben | 8.00 | 8.05 | 8.05 | 7.99 | 8.12 | 8.08 |
| Propyl paraben | 2.05 | 2.00 | 2.18 | 2.06 | 2.09 | 1.96 |
| Benzyl alcohol | 208.29 | 207.47 | 203.66 | 158.42 | 144.64 | 143.21 |
| Propylene glycol | 1496.30 | 1502.17 | 1505.17 | 1994.41 | 2008.30 | 2007.37 |
| Polyethylene glycol 400 | 2497.40 | 2495.34 | 2501.84 | 2008.76 | 2018.83 | 2002.24 |
| Total (mg) | 10002.27 | 10010.63 | 10028.05 | 10013.53 | 10027.59 | 10020.81 |
| Result | Clear thick gel | Clear thick gel | Clear thick gel | Clear thick gel | Clear thick gel | Clear thick gel |

The $^{14}C$ radiolabelled MTZ (GE Healthcare) had a specific activity of 57 mCi/mmol with a radiochemical purity of 99.2%. $^{14}C$-labeled MTZ stock solution was prepared by adding 3.5 ml water to 37 MBq of $^{14}C$-labeled MTZ and vortex mixing until the $^{14}C$-labeled MTZ dissolved.

As a control, 10 g of a 0.75 wt % $^{14}C$-labeled MTZ gel corresponding to FDA approved 0.75 wt % MTZ gels (such as, for example, METROGEL VAGINAL®)) was prepared as follows:

Paraben phase: Methyl paraben (8.03 mg), propylparaben (2.05 mg) and propylene glycol (303.28 mg) were weighed into a 28 ml glass vial and stirred until dissolved. The vial was then equilibrated at 55° C. and water (3.5 g) added while For the experiment, a full thickness human skin was mounted in a Franz cell with a Ph 4 phosphate buffer (pH 4) as receiver fluid to ensure sink conditions. A finite dose of test gel equivalent to 10 mg/cm$^2$ was applied to the membrane and the diffusion of $^{14}C$-labeled MTZ determined over time.

The test gels (7 μl) were applied to the surface of the membrane using a positive displacement pipette. Due to the large number of gels tested, the study was split into several separate experiments. Two skin donors were randomly assigned across all experiments so that each gel was tested on both skin donors (n=6 cells per gel).

The receptor compartment of the Franz cells was filled with receiver fluid and the cells fixed in a water bath maintained at 37° C. The receptor chamber contents were continuously agitated by small magnetic followers. At t=1, 2, 3, 4, 6, 8 and 24 h, samples of receiver fluid were taken from the receptor compartment, and replaced with fresh receiver medium and assayed by scintillation counting.

At the end of the experiment, a mass balance was carried out, analysing donor chamber, surface residue, Stratum corneum (SC), remaining epidermis, dermis and receiver chamber. The method involved removal of the SC by tape stripping and processing of the remaining epidermal layer and dermis using standard procedures. The methods are described briefly below.

Unabsorbed formulation: the surface of each Franz cell donor chamber was wiped gently with a cotton bud using 5 clockwise and anti-clockwise movements. The procedure was repeated on four occasions using alternate wet (previously immersed in receiver fluid) and dry cotton buds. The cotton buds were added to scintillation cocktail before analysis. Two tape strips were removed from the skin and regarded as the unabsorbed formulation and included in the total surface activity. The tape strips were placed into a scintillation vial to which 1 mL of water was added. These were left to soak for 72 h to allow the formulation to dissolve and disperse into water. Scintillation cocktail (4 mL) was added to the vial prior to analysis by liquid scintillation (LSC). The surface of each Franz cell receiver chamber was wiped gently with a cotton bud using five clockwise and anti-clockwise movements. This procedure was repeated on two occasions using alternate wet (previously immersed in receiver fluid) and dry cotton buds. The cotton buds were added to scintillation cocktail before analysis.

Stratum corneum (SC): SC was removed by carefully tape stripping the skin ten times using Scotch adhesive tape. The first five tape strips were placed together in one scintillation vial and the second five together in a second vial. 1 mL of water was added to each vial and these were left to soak for 72 h to allow the formulation to dissolve and disperse into the water. Scintillation cocktail (4 mL) was added to the vial prior to analysis by LSC.

Epidermis: The remaining section of the epidermis (following tape stripping) was carefully removed from the dermis with a scalpel. The epidermis was placed into a glass vial containing 2 ml of Soluene 350 and incubated at 50° C. for 72 h before analysis by LSC.

Dermis: The remaining dermal layer was placed in to a glass vial containing 2 ml of Soluene 350 and digested by incubation at 50° C. for 72 h before analysis by LSC.

Results. The amounts of $^{14}$C-labeled MTZ recovered from the various skin layers for each gel tested are provided in Table 25, below. These are represented graphically in FIG. 3A. The same data represented as a percentage of the applied dose are provided in Table 26, below and graphically in FIG. 4A.

Additional graphical representations are provided in FIGS. 5A and 6A.

There was no statistical difference (p>0.05) between the amount of MTZ detected in the donor chamber, receiver chamber, epidermis, and dermis for any of the formulations tested. However, significant differences in the amounts detected in the receiver fluid and the Stratum corneum were observed with the high dosage MTZ gels as compared to 0.75 wt % Metrogel®. The levels of MTZ observed in the receiver fluid following application of Metrogel®) (4.83±0.97 µg) were 4-16 higher (2-9 fold when normalized for concentration; p<0.05) than from the new PB formulations (min 0.31±0.27 µg from MG33PB and max 1.17±0.25 µg from MG36PB), with the possible exception of MG37PB (3.62±2.02 µg). However the levels of $^{14}$C-labeled MTZ in the Stratum corneum following application of the exemplary test gels (min 17.80±3.45 µg from MG36PB and max 33.15±19.86 µg from MG35PB) were 50-90 fold higher (29-53 fold higher when normalized to concentration) than those obtained for Metrogel®) (0.37±0.74 µg). This difference was reflected in the amount of radio-labeled MTZ recovered unabsorbed from the skin surface were the amount of drug recovered from the Metrogel®) formulation (45.03±1.20 µg) was comparable to the exemplary test gels (min 55.69±5.42 µg from MG33PB and max 65.23±3.29 µg from MG34PB) despite the difference in initial concentrations.

A similar experiment was carried out with exemplary gels containing 1.5 wt % MTZ, yielding similar results (provided in FIGS. 3B, 4B, 5B and 6B).

Thus, a greater quantity of MTZ is retained in the superficial layers of the skin with the high dosage mucoadhesive MTZ aqueous-based gels described herein as compared to conventional 0.75 wt % MTZ gels, while at the same time yielding lower levels in receiver fluid, corresponding to expected lower systemic levels when applied topically to skin.

TABLE 25

Mean (±SEM) Recovery (µg) of $^{14}$C MTZ from Gels Applied to Full Thickness Human Skin

| Test Gel | N | Receiver Fluid | Donor Chamber | Receiver Chamber | Surface Residue | Stratum corneum | Epidermis | Dermis | Total |
|---|---|---|---|---|---|---|---|---|---|
| Metrogef | 4 | 4.83 ± 0.97 | 0.01 ± 0.00 | 0.18 ± 0.06 | 45.03 ± 1.20 | 0.37 ± 0.74 | 0.47 ± 0.08 | 0.65 ± 0.17 | 51.54 ± 1.09 |
| MG32PB | 6 | 0.47 ± 0.10 | 0.01 ± 0.00 | 0.01 ± 0.00 | 59.60 ± 17.84 | 29.47 ± 16.56 | 0.54 ± 0.05 | 0.60 ± 0.07 | 91.00 ± 4.03 |
| MG33PB | 6 | 0.31 ± 0.27 | 0.10 ± 0.10 | 0.00 ± 0.00 | 55.69 ± 5.42 | 28.14 ± 2.66 | 1.17 ± 0.48 | 0.72 ± 0.14 | 86.01 ± 3.42 |
| MG34PB | 5 | 1.02 ± 0.11 | 0.35 ± 0.35 | 0.05 ± 0.02 | 65.23 ± 3.29 | 18.78 ± 3.51 | 1.69 ± 0.44 | 0.78 ± 0.18 | 87.77 ± 2.69 |
| MG35PB | 5 | 0.75 ± 0.16 | 0.02 ± 0.01 | 0.02 ± 0.00 | 61.42 ± 24.96 | 33.15 ± 19.86 | 0.61 ± 0.11 | 0.55 ± 0.04 | 96.34 ± 7.21 |
| MG36PB | 5 | 1.17 ± 0.25 | 0.02 ± 0.01 | 0.05 ± 0.00 | 56.47 ± 4.38 | 17.80 ± 3.45 | 2.09 ± 0.55 | 2.66 ± 1.04 | 79.97 ± 3.71 |
| MG37PB | 5 | 3.62 ± 2.02 | 0.03 ± 0.02 | 0.07 ± 0.04 | 57.89 ± 4.95 | 20.98 ± 2.56 | 3.79 ± 1.46 | 1.31 ± 0.58 | 86.47 ± 5.43 |

"N" is the number tested

TABLE 26

Mean Percentage Recovery (±SEM) of $^{14}$C MTZ from Gels Applied to Full Thickness Human Skin

| Gel | N | Receiver Fluid | Donor Chamber | Receiver Chamber | Surface Residue | Stratum corneum | Epidermis | Dermis | Total |
|---|---|---|---|---|---|---|---|---|---|
| Metrogel ® | 4 | 9.20 ± 1.85 | 0.01 ± 0.00 | 0.34 ± 0.11 | 85.78 ± 2.28 | 0.71 ± 0.14 | 0.90 ± 0.15 | 1.24 ± 0.33 | 98.17 ± 2.07 |
| MG32PB | 6 | 0.52 ± 0.11 | 0.01 ± 0.00 | 0.01 ± 0.00 | 65.89 ± 19.60 | 32.38 ± 18.20 | 0.59 ± 0.06 | 0.66 ± 0.08 | 100.00 ± 4.43 |
| MG33PB | 6 | 0.34 ± 0.03 | 0.11 ± 0.11 | 0.00 ± 0.00 | 61.20 ± 5.96 | 30.92 ± 2.92 | 1.29 ± 0.53 | 0.79 ± 0.15 | 94.52 ± 3.76 |
| MG34PB | 5 | 1.12 ± 0.12 | 0.39 ± 0.38 | 0.06 ± 0.02 | 71.68 ± 3.62 | 20.64 ± 3.86 | 1.86 ± 0.48 | 0.86 ± 0.20 | 96.45 ± 2.96 |
| MG35PB | 5 | 0.82 ± 0.18 | 0.02 ± 0.01 | 0.02 ± 0.00 | 67.49 ± 27.43 | 36.43 ± 21.82 | 0.67 ± 0.12 | 0.60 ± 0.04 | 105.87 ± 7.92 |
| MG36PB | 5 | 1.29 ± 0.27 | 0.02 ± 0.01 | 0.05 ± 0.00 | 62.06 ± 4.81 | 19.56 ± 3.79 | 2.30 ± 0.60 | 2.92 ± 1.14 | 87.88 ± 4.08 |
| MG37PB | 5 | 3.98 ± 2.22 | 0.03 ± 0.02 | 0.08 ± 0.04 | 63.62 ± 5.44 | 23.06 ± 2.81 | 4.17 ± 1.61 | 1.44 ± 0.64 | 95.02 ± 5.97 |

"N" is the number tested

Example 7: Permeation Studies With Porcine Vaginal Tissue

A permeation study with exemplary test gel MG33PB and a 0.75 wt % MTZ control gel similar to that described in Example 6 was carried out in a Franz cell using porcine vaginal tissue from which excess muscle was removed. MTZ was extracted from tissue using Soluene. In this experiment, gels did not include $^{14}$C-labeled MTZ. MTZ recovery was measured via HPLC. The mean quantities of MTZ recovered from the surface of the vaginal tissue and from within the vaginal tissue 24 hr after application of test or control gel are provided in Table 27, below. In the data below, n=5, with one outlier from each of the test and control experiments having been eliminated.

TABLE 27

| | Mean MTZ Recovery (μg) | |
|---|---|---|
| | Surface (mean ± SEM) | Vaginal Tissue (mean ± SEM) |
| MG33PB | 0.175 ± 0.045 | 9.615 ± 2.825 |
| 0.75 wt % MTZ control | 0.000 ± 0.000 | 4.287 ± 0.707 |

The data are also represented graphically in FIG. 7. The cumulative amount of MTZ that permeated through the vaginal tissue as a function of time throughout the course of the experiment are illustrated in FIG. 8. In FIG. 8, data are represented as the mean (±SEM) amount of MTZ (in μg) that permeated per unit area of vaginal tissue (μg/cm$^2$). N=5 for both test and control batches.

In this experiment, only about 30% of the total amount of MTZ applied for both the test and control gels was recovered.

Only approximately 30% of the total quantity of MTZ was recovered from both the test and control arms of the experiment.

Example 8: An Exemplary High Dosage Mucoadhesive Aqueous-Based Gel Containing 1.3 wt % MTZ is Surprisingly Effective, and Surprisingly More Effective than an FDA-Approved 0.75 wt % MTZ Gel when Clinically Used to Treat Women Diagnosed with Bacterial Vaginosis Introduction. A clinical evaluation of a specific embodiment of a high dosage mucoadhesive MTZ aqueous-based gel containing 1.3 wt % MTZ, formulation MG33PB, was carried out to assess its safety and efficacy. In the study, MG33PB was evaluated against 0.75 wt % METROGEL VAGINAL® ("MGV") and different test groups were used to determine the efficacy of treatment after 1, 3, and 5 days.

General Methodology. A multicenter, randomized, investigator-blinded, dose-ranging efficacy and safety study of MG33PB (QD×1 day, QD×3 consecutive days, and QD×5 consecutive days) compared with MGV (QD×5 consecutive days) for the treatment of BV was conducted in accordance with the FDA Guidance (draft FDA guidance titled, "Guidance for Industry: Bacterial Vaginosis-Developing Antimicrobial Drugs for Treatment," draft dated July, 1998). Subjects were evaluated at 3 time points: one Screening/Baseline Visit, one Post-treatment Phone Call, and one End of Study [EOS]/Test-of-Cure [TOC] Visit). Subjects participated for up to 30 days. The study design is presented schematically in Table 28:

TABLE 28

| Screening/Baseline | Post treatment Phone Call | EOS/TOC Visit |
|---|---|---|
| Day 1 | Days 8 to 10 | Days 21 to 30 |
| Visit 1 | Phone Call | Visit 2 |

Study Population. Participants who met all of the inclusion criteria delineated below were permitted to participate in the study. Those who met any one of the exclusion criteria delineated below were not permitted to participate in the study.

Inclusion Criteria
1. Willing and able to give written informed consent.
2. Female at least 18 years of age.
3. In good general health, as confirmed by a medical history at screening visit with no known medical conditions that, in the Investigator's opinion, might interfere with study participation.
4. Willing and able to participate in the study as an outpatient, make required visits to the study center, and comply with all study requirements including concomitant medication and other treatment restrictions.
5. For women of childbearing potential, have a negative urine pregnancy test result prior to study treatment initiation.
6. Have a clinical diagnosis of BV, defined as having all of the following criteria:
   1. Off-white (milky or gray), thin, homogenous discharge,
   2. The presence of clue cells >20% of the total epithelial cells on microscopic examination of the saline wet mount,
   3. pH of vaginal fluid >4.7, and
   4. Positive 10% KOH whiff test.

7. Agree to abstain from sexual intercourse throughout the first 7 days of the study. Following the first 7 days, agree to use a non-lubricated condom when engaging in sexual intercourse.
8. Are willing to abstain from alcohol ingestion during the treatment period and for 1 day afterward.
9. Agree to refrain from the use of intravaginal products for the duration of the study (e.g., douches, feminine deodorant sprays, spermicides, lubricated condoms, tampons, and diaphragms).

Exclusion Criteria
1. Are pregnant, lactating, or planning to become pregnant during the study period.
2. Are menstruating at the time of the diagnosis or anticipate the onset of menses during the treatment phase of the study.
3. Experience a clinically important medical event within 90 days of the visit (e.g., stroke, myocardial infarction, etc.).
4. Have known or suspected other infectious causes of vulvovaginitis (e.g., Candidiasis, *Trichomonas vaginalis, Chlamydia trachomatis, Neisseria gonorrhoeae*, or active Herpes simplex) or any other vaginal or vulvar condition that, in the Investigator's opinion, will confound the interpretation of clinical response (*Chlamydia trachomatis* and *Neisseria gonorrhoeae* test results are not available at the time of randomization).
5. Have a Gram stain slide Nugent score of <4 (results are not available at the time of randomization but are utilized to determine post-study analysis populations).
6. Received antifungal or antimicrobial therapy (systemic or intravaginal) within 14 days of randomization. Antiviral therapies (non-intravaginal) are acceptable.
7. Have taken di sulfiram within 14 days of randomization.
8. Demonstrate a previous hypersensitivity reaction to metronidazole, either orally or topically administered, or any form of parabens.
9. Have a primary or secondary immunodeficiency.
10. Are being treated or are planning to be treated during the study period for cervical intra epithelial neoplasia (CIN) or cervical carcinoma.
11. Are using anticoagulation therapy with Coumadin (warfarin).
12. Are using systemic corticosteroids or systemic antibiotics.
13. Are previously enrolled in this study.
14. Participate in another clinical trial or have taken an experimental drug or device within the last 30 days.
15. Are unwilling or unable to comply with the requirements of the protocol.

Treatment Groups. After all screening/baseline evaluations and assessments were completed, subjects were instructed in the proper technique for application of study drug and were randomly assigned by an Unblinded Drug Dispensing Coordinator in a 1:1:1:1 ratio to one of the following treatments groups:
   MGV: QD×5 consecutive days,
   MG33PB: QD×1 day,
   MG33PB: QD×3 consecutive days, and
   MG33PB: QD×5 consecutive days.

Each subject received 1 kit of study drug. Each kit contained either:
   Study medication, MG33PB, supplied in one 70-gram tube with the appropriate number of applicators, or
   Comparator medication, MGV, supplied in one 70-gram tube, with five (5) applicators.

Various subgroup populations were assessed for outcome (discussed in more detail, below). The "Intent-to-Treat" (ITT) population included all subject randomized into the study. The "Modified Intent-to-Treat" (MITT) population included all subjects randomized who received any study medication, had at least 1 post-baseline visit/assessment, had a negative test for *Neisseria gonorrhoeae* and *Chlamydia trachomatis*, and a Gram stain slide Nugent Score of ≥4 at Visit 1. Subjects with missing primary efficacy data were counted as failures for the primary efficacy endpoint and were included in the MITT population. The "Per-Protocol" (PP) population included subjects in the MITT population who met the following criteria:
   Satisfy all inclusion and exclusion criteria and have no protocol violations,
   Start study medication on the day of or within two days after the day of randomization,
   Are compliant with study medication,
   Have no antimicrobial drug use (other than allowed per protocol) during study period (Randomization through the TOC visit),
   No additional intravaginal products during the duration of the study, and
   Have the TOC Gram's stain Nugent score result obtained between days 20 and 31, relative to the first day of treatment.
   A subject whose end of study visit was prior to day 21 was included in the PP population if data indicated that the subject was a clinical failure for bacterial vaginosis without another specified cause (i.e., *trichomonas, chlamydia,* gonorrhea).

The "Safety" population included all randomized subjects who applied any amount of study medication.

Blinding. Since the study medication and the comparator were dosed using different treatment regimens, an Investigator-blinded study design was utilized. Treatment assignment was concealed from Investigators and study coordinators, and an independent drug dispensing coordinator at each site performed treatment assignment and dispensing.

Restricted Medications/Treatments. The following medications, preparations, and treatments that could potentially affect the study results were prohibited during the study:
1. Alcohol ingestion during the treatment period and for 1 day afterward.
2. Disulfiram during the treatment period and for 1 day afterward.
3. Intravaginal products for the duration of the study (e.g., douches, feminine deodorant sprays, spermicides, lubricated condoms, tampons, and diaphragms).
4. Systemic or intravaginal antimicrobial therapies for the duration of the study, with the exception of oral antifungal therapy (e.g., oral fluconazole) to treat intercurrent conditions (e.g. Candidiasis). Anti-viral therapies (non-intravaginal) were acceptable.
5. Treatment for CIN or cervical carcinoma.
6. Coumadin or warfarin.
7. Systemic corticosteroids.

Efficacy and Safety Variables. Efficacy analyses were conducted on both the PP and MITT populations.

The primary efficacy variable was assessed at Visit 2 (EOS/TOC) and is evidence of a therapeutic cure. A subject considered to be therapeutically cured must have achieved both clinical cure and bacteriological cure at EOS/TOC.

Clinical cure was defined as resolution of the clinical findings from the Baseline Visit and was further defined as:
1. absence of an off-white (milky or gray), thin, homogeneous discharge;

2. negative 10% KOH whiff test;
3. absence of clue cells in saline wet mount; and
4. vaginal fluid pH of <4.7

In addition, the subject must not have received any antimicrobial drugs (other than allowed per protocol) during the study period and the Investigator must have answered "no" at EOS to the question "In your opinion, does the patient require additional treatment for BV infection at this time?"

Bacteriological cure was defined as a Nugent score of <4.

The key secondary efficacy variables for this study were:

Proportion of subjects with clinical cure at the TOC/EOS visit.

Proportion of subjects with bacteriological cure at TOC/EOS visit.

Time to resolution of symptoms (abnormal discharge and odor), defined as the time interval (in days) from randomization to the day indicating resolution of symptoms in the subject's diary.

Pelvic exam results including itching, irritation, and inflammation.

Subject questionnaire and diary data.

Subjects who were classified as clinical failures at an unscheduled interim visit had their clinical and bacteriological results and treatment assessments carried forward to the EOS/TOC Visit.

Safety analyses were conducted on the Safety population and included an evaluation of vaginosis history and prior treatment, pelvic examination, concomitant medication monitoring, and AE/SAE monitoring.

Statistical Methods and Analyses.

Study Populations for Analyses. The various study populations are defined above. The ITT population was used to summarize subject disposition, demographic and baseline characteristics, medical history, and prior/concomitant medications. The MITT population was used for supportive efficacy analyses. The PP population was used for the primary analyses. The Safety population was used for study drug exposure and all safety analyses. Subjects were analyzed as treated.

Statistical Analysis for Primary and Secondary Endpoints. For proportion variables, data were summarized by treatment group along with exact 95% confidence intervals (CIs). Subjects who received other antimicrobial drugs, i.e., other than those allowed per protocol, during the study (i.e., any time from the date of screening/randomization to the date of the last visit) were counted as failures.

The Kaplan-Meier survival curve for time to resolution of symptoms was plotted for all treatment groups.

No formal statistical testing was performed to compare treatment groups. Final selection of the treatment regimen was based on cure rates, consistency of results, safety, and convenience information.

Safety Analyses. Safety data was comprised of the assessment (number and %) of all treatment-emergent adverse events (TEAEs), any serious adverse events (AEs), treatment related TEAEs, severe TEAEs, and AEs leading to study discontinuation for each treatment group.

Investigators chose amongst the following terms to describe the severity of an AE: Mild, Moderate, or Severe. The relationship of each AE to the study drug was evaluated by the Investigator as: Not Related, Probably Not Related, Probably Related, or Related. Note: Treatment-related AEs include those that are categorized as Probably Related or Related.

Treatment-emergent adverse events (TEAEs) were defined as those AEs that either have an onset time on or after the start of study drug and no more than 30 days after the last dose of study drug, or that were ongoing at the time of study drug initiation and increased in severity or became closer in relationship to study drug during treatment or during the 30 day period after the last dose of study drug.

TEAEs were summarized by the overall incidence of at least one event, incidence by system organ class (SOC), and incidence by SOC and preferred term. TEAEs were also summarized by severity and by relationship to study product. Also, the following treatment-emergent AEs were summarized below: Serious TEAEs, treatment-related TEAEs, severe TEAEs and TEAEs leading to study discontinuation.

Results of Clinical Evaluation of Safety and Efficacy.

Disposition of Subjects. Disposition for the study subjects is displayed in Table 29, below. A total of 255 subjects were randomly assigned to the four study treatments and all but one subject (in the MGV group) was dosed and included in the Safety population. 234 subjects (91.8%) completed the study. Among the 21 (8.2%) subjects who discontinued early, 9 (3.5%) were lost to follow-up, 5 (2.0%) had a positive *Neisseria gonorrhoeae* and/or *Chlamydia trachomatis* screening test result.

There were 255 (100.0%) subjects in the ITT population, 228 (89.4%) subjects in the MITT population, and 189 (74.1%) subjects in the PP population. Twenty-seven (10.6%) subjects were excluded from the MITT population; the majority 23 (90.0%) because of their baseline Nugent scores. For the 66 (25.9%) subjects excluded from the PP population, the most common reason, occurring in 30 (11.8%) subjects, was because a Nugent score had not been performed within 20 to 31 days from the first dose of study medication. A summary of subject populations is provided in Table 30, below.

Demographics. At baseline, the mean age of subjects enrolled into the study was 35.1 (±9.93) years. Subjects were evenly divided between groups <35 years (51.4%) and >35 years (48.6%) and were balanced by age range across treatment groups. A summary of demographics is provided in Table 31, below.

TABLE 29

| Disposition of ITT Population Number of total subjects (% of total subjects) | | | | | |
|---|---|---|---|---|---|
| | MGV (QD × 5 Days) | MG33PB (QD × 1 Day) | MG33PB (QD × 3 Days) | MG33PB (QD × 5 Days) | Overall |
| Randomized | 66 (100.0) | 65 (100.0) | 60 (100.0) | 64 (100.0) | 255 (100.0) |
| Treated (safety population) | 65 (98.5) | 65 (100.0) | 60 (100.0) | 64 (100.0) | 254 (99.6) |
| Completed | 59 (89.4) | 57 (87.7) | 55 (91.7) | 63 (98.4) | 234 (91.8) |
| Discontinued | 7 (10.6) | 8 (12.3) | 5 (8.3) | 1 (1.5) | 21 (8.2) |
| Reason for discontinuation | | | | | |
| Investigator's request | 0 | 1 (1.5) | 0 | 0 | 1 (0.4) |
| Subject's request (not due to AE) | 0 | 0 | 1 (1.7) | 0 | 1 (0.4) |

TABLE 29-continued

Disposition of ITT Population Number of total subjects (% of total subjects)

|  | MGV (QD × 5 Days) | MG33PB (QD × 1 Day) | MG33PB (QD × 3 Days) | MG33PB (QD × 5 Days) | Overall |
|---|---|---|---|---|---|
| Non-compliance with study procedures | 1 (1.5) | 0 | 0 | 0 | 1 (0.4) |
| Subject lost to follow-up | 1 (1.5) | 4 (6.2) | 3 (5.0) | 1 (1.6) | 9 (3.5) |
| Positive infection test result | 4 (6.1) | 1 (1.5) | 0 | 0 | 5 (2.0) |
| Other (not due to AE) | 1 (1.5) | 2 (3.1) | 1 (1.7) | 0 | 4 (1.6) |
| Adverse event | 0 | 0 | 0 | 0 | 0 |
| Use of prohibited concomitant therapy | 0 | 0 | 0 | 0 | 0 |

\* Subjects had a positive screening test result for *Neisseria gonorrhoeae* and/or *Chlamydia trachomatis* that was not available until after randomization

TABLE 30

Disposition of Subject Populations Number of total subjects (% of total subjects)

|  | MGV (QD × 5 Days) | MG33PB (QD × 1 Day) | MG33PB (QD × 3 Days) | MG33PB (QD × 5 Days) | Overall |
|---|---|---|---|---|---|
| Safety Population | 65 (98.5) | 65 (100.0) | 60 (100.0) | 64 (100.0) | 254 (99.6) |
| ITT Population | 66 (100.0) | 65 (100.0) | 60 (100.0) | 64 (100.0) | 255 (100.0) |
| MITT population | 59 (89.4) | 59 (90.8) | 54 (90.0) | 56 (87.5) | 228 (89.4) |
| Excluded from MITT Population | 7 (10.6) | 6 (9.2) | 6 (10.0) | 8 (12.5) | 27 (10.6) |
| PP Population | 49 (74.2) | 43 (66.2) | 48 (80.0) | 49 (76.6) | 189 (74.1) |
| Excluded from PP Population | 17 (25.8) | 22 (33.8) | 12 (20.0) | 15 (23.4) | 66 (25.9) |
| Reason(s) excluded from PP Population* | | | | | |
| Did not start study medication on time | 4 (6.1) | 5 (7.7) | 4 (6.7) | 1 (1.6) | 14 (5.5) |
| Non-Compliant with study medication | 6 (9.1) | 7 (10.8) | 4 (6.7) | 2 (3.1) | 19 (7.5) |
| Did not satisfy all inclusion/exclusion criteria | 0 | 0 | 0 | 0 | 0 |
| Used anti-microbial drug(s) | 4 (6.1) | 3 (4.6) | 1 (1.7) | 2 (3.1) | 10 (3.9) |
| Took other intravaginal product during stlidv | 0 | 1 (1.5) | 0 | 1 (1.6) | 2 (0.8) |
| EOS Nugent not done within dose days 20-31 | 10 (15.2) | 12 (18.5) | 4 (6.7) | 4 (6.3) | 30 (11.8) |

*Subjects may have had multiple reasons for not being included

TABLE 31

Demographics: Intent-to-Treat Population Number of total subjects (% of total subjects)

|  | MGV (QD × 5 Days) | MG33PB (QD × 1 Day) | MG33PB (QD × 3 Days) | MG33PB (QD × 5 Days) | Overall |
|---|---|---|---|---|---|
| Age, years (n) | | | | | |
| Mean (SD) | 35.0 (9.30) | 35.0 (10.13) | 33.0 (9.01) | 37.4 (10.91) | 35.1 (9.93) |
| Median | 35.0 | 33.0 | 32.0 | 36.0 | 34.0 |
| Min, Max | 19, 60 | 19, 66 | 18, 59 | 21, 67 | 18, 67 |
| Age Group, years n (%) | | | | | |
| <35 | 32 (48.5) | 36 (55.4) | 35 (58.3) | 28 (43.8) | 131 (51.4) |
| >35 | 34 (51.5) | 29 (44.6) | 25 (41.7) | 36 (56.3) | 124 (48.6) |
| Sex, N (%) | | | | | |
| Female | 66 (100.0) | 65 (100.0) | 60 (100.0) | 64 (100.0) | 255 (100.0) |
| Race, N (%) | | | | | |
| White | 33 (50.0) | 33 (50.8) | 27 (45.0) | 28 (43.8) | 121 (47.5) |
| Black/African American | 32 (48.5) | 32 (49.2) | 32 (53.3) | 36 (56.3) | 132 (51.8) |
| Other | 1 (1.5) | 0 | 1 (1.7) | 0 | 2 (0.8) |

TABLE 31-continued

| Demographics: Intent-to-Treat Population Number of total subjects (% of total subjects) | | | | | |
|---|---|---|---|---|---|
| | MGV (QD × 5 Days) | MG33PB (QD × 1 Day) | MG33PB (QD × 3 Days) | MG33PB (QD × 5 Days) | Overall |
| Ethnicity, N (%) | | | | | |
| Hispanic/Latino | 12 (18.2) | 9 (13.8) | 10 (16.7) | 15 (23.4) | 46 (18.0) |
| Non-Hispanic/Latino | 54 (81.8) | 56 (86.2) | 50 (83.3) | 49 (76.6) | 209 (82.0) |

Abbreviations:
max = maximum;
min= minimum
SD = standard deviation.

Bacterial Vaginosis History and Prior Bacterial Vaginosis Treatment. Bacterial vaginosis (BV) history and prior treatment for BV are summarized in Table 32, below, for the ITT population.

TABLE 32

| Bacterial Vaginosis History and Prior Bacterial Vaginosis Treatment: Intent-to-Treat | | | | | |
|---|---|---|---|---|---|
| | MGV (QD × 5 Days) | MG33PB (QD × 1 Day) | MG33PB (QD × 3 Days) | MG33PB (QD × 5 Days) | Overall |
| Duration of current BV episode at baseline, n (%) | | | | | |
| ≤3 weeks | 23 (34.8) | 21 (32.3) | 22 (36.7) | 20 (31.3) | 86 (33.7) |
| >3 wks and <3 mos | 25 (37.9) | 28 (43.1) | 29 (48.3) | 27 (42.2) | 109 (42.7) |
| >3 mos | 18 (27.3) | 16 (24.6) | 9 (15.0) | 17 (26.6) | 60 (23.5) |
| Duration of current BV episode at baseline, n (%) | | | | | |
| N | 66 | 65 | 60 | 64 | 255 |
| Mean | — | — | 93.7 | 150.1 | 151.6 |
| (SD) | 231.5 (990.20) | 125.6 (288.63) | (244.45) | (459.59) | (583.78) |
| Median | 40.0 | 41.0 | 30.5 | 36.0 | 36.0 |
| Min, Max | 1,7924 | 1,2102 | 2, 1713 | 1,3534 | 1, 7924 |
| Had previous episode (s) of BV, n (%) | | | | | |
| Yes | 23 (34.8) | 27 (41.5) | 25 (41.7) | 20 (31.3) | 95 (37.3) |
| No | 43 (65.2) | 38 (58.5) | 35 (58.3) | 44 (68.8) | 160 (62.7) |

Abbreviations:
max = maximum;
min = minimum;
SD = standard deviation.

Overall, 95 (37.3%) subjects reported previous episodes of BV; the mean duration of the current BV episode was 151.6 days. The treatment groups were similar with respect to bacterial vaginosis history and baseline characteristics.

Efficacy Results. Summary of Cure Rates. Summaries of the cure rates (primary endpoint Therapeutic Cure Rate and secondary endpoints Clinical and Bacteriologic Cure rates) in the PP population and the MITT populations are presented in Table 33, below.

TABLE 33

| Summary of Cure Rates: Per-Protocol Population Number of total subjects (% of total subjects) | | | | |
|---|---|---|---|---|
| | MGV (QD × 5 Days) | MG33PB (QD × 1 Day) | MG33PB (QD × 3 Days) | MG33PB (QD × 5 Days) |
| Therapeutic cure | | | | |
| Cured, n (%) | 10 (20.4) | 13 (30.2) | 12 (25.0) | 16 (32.7) |
| Failed, n (%) | 39 (79.6) | 30 (69.8) | 36 (75.0) | 33 (67.3) |

TABLE 33-continued

Summary of Cure Rates: Per-Protocol Population Number of total subjects (% of total subjects)

|  | MGV (QD × 5 Days) | MG33PB (QD × 1 Day) | MG33PB (QD × 3 Days) | MG33PB (QD × 5 Days) |
|---|---|---|---|---|
| Clinical cure | | | | |
| Cured, n (%) | 14 (28.6) | 16 (37.2) | 17 (35.4) | 22 (44.9) |
| Failed, n (%) | 35 (71.4) | 27 (62.8) | 31 (64.6) | 27 (55.1) |
| Bacteriological cure | | | | |
| Cured, n (%) | 15 (30.6) | 13 (30.2) | 17 (35.4) | 23 (46.9) |
| Failed, n (%) | 34 (69.4) | 30 (69.8) | 31 (64.6) | 26 (53.1) |

As shown in Table 34, below, the results for the MITT population are similar to the PP population.

TABLE 34

Summary of Cure Rates: Modified Intent-to-Treat Population Number of total subjects (% of total subjects)

|  | MGV (QD × 5 Days) | MG33PB (QD × 1 Day) | MG33PB (QD × 3 Days) | MG33PB (QD × 5 Days) |
|---|---|---|---|---|
| Therapeutic cure | | | | |
| Cured, n (%) | 12 (20.3) | 15 (25.4) | 12 (22.2) | 17 (30.4) |
| Failed, n (%) | 47 (79.7) | 44 (74.6) | 42 (77.8) | 39 (69.6) |
| Clinical cure | | | | |
| Cured, n (%) | 17 (28.8) | 18 (30.5) | 17 (31.5) | 23 (41.1) |
| Failed, n (%) | 42 (71.2) | 41 (69.5) | 37 (68.5) | 33 (58.9) |
| Bacteriological cure | | | | |
| Cured, n (%) | 18 (30.5) | 18 (30.5) | 18 (33.3) | 26 (46.4) |
| Failed, n (%) | 41 (69.5) | 41 (69.5) | 36 (66.7) | 30 (53.6) |

Summary of Absent or Present by Each Therapeutic Cure Criteria at the End of Study/Test of Cure Visit. The results for absent or present at the EOS/TOC Visit for each of the 4 established therapeutic cure criteria are presented for the PP population in Table 35. Results are similar in the MITT population.

TABLE 35

Results for Therapeutic Cure Criteria at Test of Cure/End of Study: Per-Protocol Population Number of total subjects (% of total subjects)

|  | MGV (QD × 5 Days) | MG33PB (QD × 1 Day) | MG33PB (QD × 3 Days) | MG33PB (QD × 5 Days) |
|---|---|---|---|---|
| Vaginal discharge | | | | |
| Absent | 22 (44.9) | 24 (55.8) | 23 (47.9) | 38 (77.6) |
| Present | 27 (55.1) | 19 (44.2) | 25 (52.1) | 11 (22.4) |
| KOH whiff test | | | | |
| Absent | 26 (53.1) | 23 (53.5) | 33 (68.8) | 39 (79.6) |
| Present | 23 (46.9) | 20 (46.5) | 15 (31.3) | 10 (20.4) |
| Clue cells (% of vaginal epithelial cells) | | | | |
| <20% | 27 (55.1) | 23 (53.5) | 28 (58.3) | 40 (81.6) |
| ≥20% | 22 (44.9) | 20 (46.5) | 20 (41.7) | 9 (18.4) |
| Vaginal pH | | | | |
| <4.7 | 19 (38.8) | 18 (41.9) | 24 (50.0) | 28 (57.1) |
| ≥4.7 | 30 (61.2) | 25 (58.1) | 24 (50.0) | 21 (42.9) |

TABLE 35-continued

Results for Therapeutic Cure Criteria at Test of Cure/End of Study: Per-Protocol
Population Number of total subjects (% of total subjects)

| | MGV (QD × 5 Days) | MG33PB (QD × 1 Day) | MG33PB (QD × 3 Days) | MG33PB (QD × 5 Days) |
|---|---|---|---|---|
| Investigator questionnaire: Did the subject use other antimicrobial drugs (other than allowed per protocol) during the study period (systemic or intravaginal)? | | | | |
| Yes | 0 | 0 | 0 | 0 |
| No | 49 (100.0) | 43 (100.0) | 48 (100.0) | 49 (100.0) |
| Investigator questionnaire: In the Investigator's opinion, does the subject require additional treatment for bacterial vaginosis at this time? | | | | |
| Yes | 24 (49.0) | 20 (46.5) | 18 (37.5) | 9 (18.4) |
| No | 25 (51.0) | 23 (53.5) | 30 (62.5) | 40 (81.6) |
| Gram stain for Nugent Scoring | | | | |
| 0 to 3: BV negative | 15 (30.6) | 13 (30.2) | 17 (35.4) | 23 (46.9) |
| 4 to 10: BV positive | 34 (69.4) | 30 (69.8) | 31 (64.6) | 26 (53.1) |

Time to Resolution of Symptoms. In the PP population, the median time to resolution of both abnormal discharge and fishy odor and the median time to resolution of fishy odor alone are shorter in all 3 metronidazole 1.3% treatment groups compared to MGV 0.75% group (median times were 5 days versus 6 and 2 days versus 3, respectfully); the median time to resolution of abnormal discharge is equal across all treatments groups (median time is 3 days). A summary of time to resolution of symptom(s) is provided in Table 36 below.

TABLE 36

Time to Resolution of Symptoms
Number of total subjects (% of total subjects)

| | MGV (QD × 5 Days) | MG33PB (QD × 1 Day) | MG33PB (QD × 3 Days) | MG33PB (QD × 5 Days) |
|---|---|---|---|---|
| Time to resolution of symptoms (abnormal discharge and fishy odor) | | | | |
| Subject resolved, n (%) | 26 (53.1) | 25 (58.1) | 29 (60.4) | 28 (57.1) |
| Median days (95% CI)[a] | 6 (4, —) | 5 (3, —) | 5 (3, —) | 5 (4, —) |
| Time to resolution of abnormal discharge | | | | |
| Subjects resolved, n (%) | 43 (87.8) | 39 (90.7) | 45 (93.8) | 42 (85.7) |
| Median days (95% CI)[a] | 3 (3, 5) | 3 (2, 3) | 3 (2, 3) | 3 (2, 5) |
| Time to resolution of fishy odor | | | | |
| Subjects resolved, n (%) | 39 (79.6) | 33 (76.7) | 39 (81.3) | 42 (85.7) |
| Median days (95% CI)[a] | 3 (2, 3) | 2 (2, 3) | 2 (2, 3) | 2 (2, 3) |

[a]Product-limit (Kaplan-Meier) method estimates; 95% CI calculation is based on the Greenwood method Summary of Therapeutic Cure Rates by Subgroups. Therapeutic cure rates in the PP population are presented by subgroups (age group, race, ethnicity, duration of current BV episode at baseline, and previous episode of BV) in Table 37 below.

TABLE 37

Summary of Therapeutic Cure Rate by Age Group, Race, and Ethnicity:
Per-Protocol Population
Number of total subjects (% of total subjects)

| | MGV (QD × 5 Days) | MG33PB (QD × 1 Day) | MG33PB (QD × 3 Days) | MG33PB (QD × 5 Days) |
|---|---|---|---|---|
| Age group | | | | |
| <35 Years Old | 4/24 (16.7) | 8/26 (30.8) | 4/29 (13.8) | 9/21 (42.9) |
| ≥35 Years Old | 6/25 (24.0) | 5/17 (29.4) | 8/19 (42.1) | 7/28 (25.0) |

TABLE 37-continued

Summary of Therapeutic Cure Rate by Age Group, Race, and Ethnicity:
Per-Protocol Population
Number of total subjects (% of total subjects)

|  | MGV (QD × 5 Days) | MG33PB (QD × 1 Day) | MG33PB (QD × 3 Days) | MG33PB (QD × 5 Days) |
|---|---|---|---|---|
| Race | | | | |
| White | 7/23 (30.4) | 10/23 (43.5) | 5/23 (21.7) | 5/20 (25.0) |
| Black/African American | 3/26 (11.5) | 3/20 (15.0) | 7/25 (28.0) | 11/29 (37.9) |
| Ethnicity | | | | |
| Hispanic/Latino | 1/8 (12.5) | 3/5 (60.0) | 2/8 (25.0) | 5/11 (45.5) |
| Non Hispanic/Latino | 9/41 (22.0) | 10/38 (26.3) | 10/40 (25.0) | 11/38 (28.9) |
| Duration of current BV episode at baseline | | | | |
| ≤3 weeks | 2/16 (12.5) | 6/14 (42.9) | 3/15 (20.0) | 7/13 (53.8) |
| >3 weeks and ≤3 months | 5/19 (26.3) | 3/18 (16.7) | 8/25 (32.0) | 5/22 (22.7) |
| >3 months | 3/14 (21.4) | 4/11 (36.4) | 1/8 (12.5) | 4/14 (28.6) |
| Previous episode (s) of BV | | | | |
| Yes | 5/18 (27.8) | 6/21 (28.6) | 3/19 (15.8) | 6/16 (37.5) |
| No | 5/31 (16.1) | 7/22 (31.8) | 9/29 (31.0) | 10/33 (30.3) |

No significant trends in achievement of therapeutic cure were evident from the analyses by subgroup.

Subject Questionnaire Results. At the end of study, all subjects were asked to complete a questionnaire. The following questions specifically asked of subjects to provide their feedback on use of the study drug:

How easy was the study drug to apply?
How convenient was the length of treatment with study drug?
How satisfied were you with the treatment you received?
If you had BV symptoms in the future, would you prefer to be treated with the current study drug or would you prefer another treatment?

A summary of the results is provided in Table 38 below.

TABLE 38

Subject End-of-Study Questionnaire Results: Per-Protocol Population Number of total subjects (% of total subjects)

| Question | MGV (QD × 5 Days) | MG33PB (QD × 1 Day) | MG33PB (QD × 3 Days) | MG33PB (QD × 5 Days) |
|---|---|---|---|---|
| How easy was the study drug to apply? | | | | |
| Somewhat easy | 0 | 1 (2.3) | 1 (2.1) | 1 (2.0) |
| Easy | 15 (30.6) | 4 (9.3) | 9 (18.8) | 12 (24.5) |
| Very Easy | 33 (67.3) | 38 (88.4) | 34 (70.8) | 33 (67.3) |
| Missing | 1 (2.0) | 0 | 4 (8.3) | 3 (6.1) |
| How convenient was the length of treatment with study drug? | | | | |
| Not convenient | 1 (2.0) | 0 | 0 | 1 (2.0) |
| Somewhat convenient | 8 (16.3) | 3 (7.0) | 5 (10.4) | 7 (14.3) |
| Convenient | 22 (44.9) | 5 (11.6) | 17 (35.4) | 22 (44.9) |
| Very Convenient | 17 (34.7) | 35 (81.4) | 22 (45.8) | 16 (32.7) |
| Missing | 1 (2.0) | 0 | 4 (8.3) | 3 (6.1) |
| How satisfied were you with the treatment you received? | | | | |
| Not satisfied | 3 (6.1) | 3 (7.0) | 2 (4.2) | 0 |
| Somewhat satisfied | 8 (16.3) | 5 (11.6) | 4 (8.3) | 3 (6.1) |
| Satisfied | 15 (30.6) | 8 (18.6) | 13 (27.1) | 15 (30.6) |
| Very Satisfied | 22 (44.9) | 27 (62.8) | 25 (52.1) | 28 (57.1) |
| Missing | 1 (2.0) | 0 | 4 (8.3) | 3 (6.1) |
| If you had Bacterial Vaginosis symptoms in the future, would you prefer to be treatment with this study drug or would you prefer another treatment? | | | | |
| Prefer current study drug | 24 (49.0) | 28 (65.1) | 26 (54.2) | 36 (73.5) |
| Prefer another treatment | 8 (16.3) | 6 (14.0) | 8 (16.7) | 4 (8.2) |
| No preference | 16 (32.7) | 9 (20.9) | 10 (20.8) | 6 (12.2) |
| Missing | 1 (2.0) | 0 | 4 (8.3) | 3 (6.1) |

Among the 4 treatment groups, the highest proportion of subjects rating the treatment as "very easy to apply", "very convenient" (for the length of treatment) and "very satisfied" was in the MG33PB 1-day group (data not shown).

Safety Results. Drug Exposure. Subjects in this 30-day study received either MGV QD×5 consecutive days; MG33PB QD×1 day; MG33PB QD×3 consecutive days; or MG33PB QD×5 consecutive days. A summary of mean days of study drug exposure for the safety population is provided in Table 39 below.

TABLE 39

Mean Days of Study Drug Exposure: Safety Population Number of total subjects (% of total subjects)

| | MGV (QD × 5 Days) | MG33PB (QD × 1 Day) | MG33PB (QD × 3 Days) | MG33PB (QD × 5 Days) | Overall |
|---|---|---|---|---|---|
| Mean (SD) | 4.9 (0.53) | 1.1 (1.03) | 3.0 (0.00) | 5.1 (0.76) | 3.6 (1.76) |

The majority of subjects in all treatment groups reported no or minimal leakage of study product.

Summary of Adverse Events. Overall, 92 (36.2%) subjects reported adverse events (AEs). All adverse events were treatment emergent (TEAEs). Twenty-nine (11.4%) subjects across the four treatment groups had TEAEs which are assessed by the Investigator as related to study drug. A summary of AEs is provided in Table 40 below.

Treatment-Emergent Adverse Effects. The most frequently reported system-organ classes (SOCs) with TEAEs overall were Infections and Infestations (47 [18.5%] subjects), Nervous System Disorders (32 [12.6%] subjects), and Reproductive System and Breast Disorders (27 [10.6%] subjects). A summary of all TEAES by system-organ class (SOC) is provided in Table 41 below.

TABLE 40

Overall Summary of Adverse Events: Safety Population Number of total subjects (% of total subjects)

| | MGV (QD × 5 Days) | MG33PB (QD × 1 Day) | MG33PB (QD × 3 Days) | MG33PB (QD × 5 Days) | Overall |
|---|---|---|---|---|---|
| Subjects with any AE[a] | 28 (43.1) | 23 (35.4) | 19 (31.7) | 22 (34.4) | 92 (36.2) |
| Subjects with any TEAE[b] | 28 (43.1) | 23 (35.4) | 19 (31.7) | 22 (34.4) | 92 (36.2) |
| Subjects with TEAE related to study drug | 7 (10.8) | 8 (12.3) | 8 (13.3) | 6 (9.4) | 29 (11.4) |
| Subjects with severe TEAE related to study drug | 0 | 1 (1.5) | 0 | 0 | 1 (0.4) |
| Subjects with any serious TEAE | 0 | 1 (1.5) | 0 | 0 | 1 (0.4) |
| Subjects with relate! serious TEAE | 0 | 0 | 0 | 0 | 0 |
| Subjects who discontinued the study due to any TEAE | 0 | 0 | 0 | 0 | 0 |
| Subjects who had a TEAE with fatal outcome | 0 | 0 | 0 | 0 | 0 |

[a]If subject has 1 or more events in any category, the subject is counted once in that category.
bATEAE is an AE onset time on or after the start of study drug and no more than 30 days after the last dose.
[c]Related AEs are AEs with one of the following relationships to the study drug: 'Probably Related' or 'Related'.

TABLE 41

Treatment-Emergent Adverse Events by System-Organ-Class: Safety Population Number of total subjects (% of total subjects)

| System-Organ Class, n (%) | MGV (QD × 5 Days) | MG33PB (QD × 1 Day) | MG33PB (QD × 3 Days) | MG33PB (QD × 5 Days) | Overall |
|---|---|---|---|---|---|
| Infections and infestations | 14 (21.5) | 13 (20.0) | 14 (233) | 6 (9.4) | 47 (18.5) |
| Nervous system disorders | 11 (16.9) | 4 (6.2) | 6 (10.0) | 11 (17.2) | 32 (12.6) |

TABLE 41-continued

Treatment-Emergent Adverse Events by System-Organ-Class: Safety Population
Number of total subjects (% of total subjects)

| System-Organ Class, n (%) | MGV (QD × 5 Days) | MG33PB (QD × 1 Day) | MG33PB (QD × 3 Days) | MG33PB (QD × 5 Days) | Overall |
|---|---|---|---|---|---|
| Reproductive system and breast disorders | 8 (12.3) | 6 (9.2) | 6 (10.0) | 7 (10.9) | 27 (10.6) |
| Gastrointestinal disorders | 3 (4.6) | 3 (4.6) | 4 (6.7) | 6 (9.4) | 16 (6.3) |
| Respiratory, thoracic and mediastinal | 3 (4.6) | 0 | 3 (5.0) | 1 (1.6) | 7 (2.8) |
| Musculoskeletal and connective tissue | 1 (1.5) | 1 (1.5) | 1 (1.7) | 1 (1.6) | 4 (1.6) |
| Psychiatric disorders | 1 (1.5) | 2 (3.1) | 1 (1.7) | 0 | 4 (1.6) |
| Blood and lymphatic system disorders | 0 | 2 (3.1) | 0 | 1 (1.6) | 3 (1.2) |
| General disorders and administration site | 0 | 2 (3.1) | 0 | 1 (1.6) | 3 (1.2) |
| Immune system disorders | 1 (1.5) | 0 | 0 | 2 (3.1) | 3 (1.2) |
| Injury, poisoning and procedural | 0 | 1 (1.5) | 0 | 1 (1.6) | 2 (0.8) |
| Metabolism and nutrition disorders | 1 (1.5) | 1 (1.5) | 0 | 0 | 2 (0.8) |
| Renal and urinary disorders | 1 (1.5) | 0 | 1 (1.7) | 0 | 2 (0.8) |
| Vascular disorders | 0 | 0 | 0 | 1 (1.6) | 1 (0.4) |

The most frequently reported TEAEs with an incidence >2.0% of subjects overall by preferred term, regardless of relationship to study medication was vulvovaginal candidiasis (25 [9.8%] subjects) and headache (21 [8.3%] subjects). A summary of all TEAEs, regardless of relationship to study medication, by preferred term and those reported in >2.0% of subjects overall in decreasing order is provided in Table 42 below.

The most frequently reported of these TEAEs considered probably related or was related to study drug are vulvovaginal candidiasis in the SOC category Infections and Infestations and vulvovaginal pruritus and burning sensation in the Reproductive System and Breast Disorders SOC. A summary of TEAEs by SOC, preferred term, and relationship to study drug with an incidence of at least 6.0% in Overall is provided in Table 43 below.

TABLE 42

Treatment-Emergent Adverse Events by Preferred Team with an Incidence > Overall: Safety Population Number of total subjects (% of total subjects)

| System-Organ-Class Preferred Term | MGV (QD × 5 Days) | MG33PB (QD × 1 Day) | MG33PB (QD × 3 Days) | MG33PB (QD × 5 Days) | Overall |
|---|---|---|---|---|---|
| Vulvovaginal candidiasis | 9 (13.8) | 8 (12.3) | 8 (13.3) | 0 | 25 (9.8) |
| Headache | 9 (13.8) | 3 (4.6) | 5 (8.3) | 4 (6.3) | 21 (8.3) |
| Nasopharyngitis | 1 (1.5) | 2 (3.1) | 3 (5.0) | 1 (1.6) | 7 (2.8) |
| Vulvovaginal pruritus | 1 (1.5) | 2 (3.1) | 4 (6.7) | 0 | 7 (2.8) |
| Pelvic pain | 3 (4.6) | 1 (1.5) | 0 | 2 (3.1) | 6 (2.4) |
| Vulvovaginal burning | 2 (3.1) | 2 (3.1) | 1 (1.7) | 1 (1.6) | 6 (2.4) |
| Nausea | 0 | 1 (1.5) | 0 | 4 (63) | 5 (2.0) |

TABLE 43

Treatment-Emergent Adverse Events by System-Organ-Class, Preferred Term, and Related* Relationship to Study Drug with an Incidence ≥6.0% in System-Organ-Class Overall: Safety Population
Number of total subjects (% of total subjects)

| System-Organ-Class Preferred Term Relationship | MGV (QD × 5 Days) | MG33PB (QD × 1 Day) | MG33PB (QD × 3 Days) | MG33PB (QD × 5 Days) | Overall |
|---|---|---|---|---|---|
| Any System/Any Term | 28 (43.1) | 23 (35.4) | 19 (31.7) | 22 (34.4) | 92 (36.2) |
| Related/Probably Related | 7 (10.8) | 8 (12.3) | 8 (13.3) | 6 (9.4) | 29 (11.4) |
| All Gastrointestinal disorders | 3 (4.6) | 3 (4.6) | 4 (6.7) | 6 (9.4) | 16 (6.3) |
| Probably Related | 1 (1.5) | 0 | 2 (3.3) | 4 (6.3) | 7 (2.8) |
| Nausea | 0 | 0 | 0 | 2 (3.1) | 2 (0.8) |
| Abdominal pain | 0 | 0 | 1 (1.7) | 1 (1.6) | 2 (0.8) |
| Abdominal discomfort | 0 | 0 | 1 (1.7) | 0 | 1 (0.4) |
| Abdominal pain upper | 0 | 0 | 0 | 1 (1.6) | 1 (0.4) |
| Abdominal distension | 1 (1.5) | 0 | 0 | 0 | 1 (0.4) |

TABLE 43

Treatment-Emergent Adverse Events by System-Organ-Class, Preferred Term, and Related*
Relationship to Study Drug with an Incidence ≥ 6.0% in System-Organ-Class Overall: Safety
Population Number of total subjects (% of total subjects)

| System-Organ-Class Preferred Term Relationship | MGV (QD × 5 Days) | MG33PB (QD × 1 Day) | MG33PB (QD × 3 Days) | MG33PB (QD × 5 Days) | Overall |
|---|---|---|---|---|---|
| Abdominal pain lower | 0 | 0 | 0 | 1 (1.6) | 1 (0.4) |
| Flatulence | 1 (1.5) | 0 | 0 | 0 | 1 (0.4) |
| Infections and infestations | 14 (21.5) | 13 (20.0) | 14 (23.3) | 6 (9.4) | 47 (18.5) |
| Probably Related | 3 (4.6) | 5 (7.7) | 5 (8.3) | 0 | 13 (5.1) |
| Vulvovaginal Candidiasis | 3 (4.6) | 5 (7.7) | 5 (8.3) | 0 | 13 (5.1) |
| Nervous system disorders | 11 (16.9) | 4 (6.2) | 6 (10.0) | 11 (17.2) | 32 (12.6) |
| Probably Related | 1 (1.5) | 1 (1.5) | 1 (1.7) | 1 (1.6) | 4 (1.6) |
| Headache | 1 (1.5) | 1 (1.5) | 1 (1.7) | 0 | 3 (1.2) |
| Dysgeusia | 0 | 0 | 0 | 1 (1.6) | 1 (0.4) |
| Reproductive system and breast disorders | 8 (12.3) | 6 (9.2) | 6 (10.0) | 7 (10.9) | 27 (10.6) |
| Related/Probably Related | 5 (7.7) | 3 (4.6) | 3 (5.0) | 3 (4.7) | 14 (5.5) |
| Vulvovaginal pruritus | 1 (1.5) | 2 (3.1) | 2 (3.3) | 0 | 5 (2.0) |
| Pelvic Pain | 0 | 0 | 0 | 1 (1-6) | 1 (0.4) |
| Vulvovaginal burning sensation | 2 (3.1) | 2 (3.1) | 1 (1.7) | 0 | 5 (2.0) |
| Vaginal haemorrhage | 0 | 0 | 1 (1.7) | 0 | 1 (0.4) |
| Vulvovaginal discomfort | 1 (1.5) | 0 | 0 | 1 (1.6) | 2 (0.8) |
| Vaginal discharge | 1 (1.5) | 0 | 1 (1.7) | 0 | 2 (0.8) |
| Vaginal odor | 0 | 0 | 1 (1.7) | 0 | 1 (0.4) |
| Vulval oedema | 0 | 1 (1.5) | 0 | 0 | 1 (0.4) |
| Vulvovaginal dryness | 1 (1.5) | 0 | 0 | 0 | 1 (0.4) |
| Vulvovaginal pain | 0 | 0 | 0 | 1 (1.6) | 1 (0.4) |

*Related included: Related and Probably Related

The majority of the adverse events were of mild or moderate intensity. A total of five subjects reported six severe events adverse events including: hypoglycemia, dizziness, abdominal pain, tooth abscess, vulval edema and vaginal burning sensation. One subject (#2904, 1.3% for 1 day) reported two severe events that were considered related to study product; vaginal burning sensation and vulval edema beginning on day 3 of the study. These events occurred concurrently with vulvovaginal pruritus, headache, back pain, and vulvovaginal candidiasis. No difference between treatment groups in the incidence of severe AEs was observed.

Serious Adverse Events. There was one SAE during this study, hypoglycemia in 1 (1.5%) subject in the MG33PB QD×1 day treatment group.

Summary. In this Example, the efficacy and safety of a 1.3% vaginal gel for bacterial vaginosis (test gel MG33PB) was explored. It was found that the MG33PB once per day for a total of 1, 3 or 5 days yielded rates of therapeutic cure similar to, or numerically better than, the marketed MGV 0.75% vaginal gel (MGV) applied once per day for a total of 5 days (Tables 33-36). No trends in efficacy were observed from analysis of the subgroups analyzed (Table 37). The highest proportion of subjects rating the treatment as "very easy to apply", "very convenient for the length of treatment" and "very satisfied" was in the MG33PB 1-day group (Table 38). The majority of adverse events were found to be mild and moderate in intensity (Tables 40-43). Surprisingly, it was discovered that a 5 day treatment regimen with MG33PB resulted in no vulvovaginal candidiasis being observed post treatment (Table 42).

Example 9: Antimicrobial Efficacy in an In Vitro Skin Infection Model

The antimicrobial efficacy of several exemplary high dosage MTZ gels against *Gardnerella vaginalis* was demonstrated in an in vitro experiment. In the experiment, ATP was recovered from infected skin treated with test gels and quantitated. The lower the amount of ATP recovered, the more effective the gel against the infection.

Two studies were carried out. A pilot study and a full scale study. The general method for the pilot study was as follows:

Fresh epidermal membrane was prepared according to a standard protocol and stored frozen at −20° C. until required.

The membrane was cut into 3 mm×3 mm segments, heat treated at 60° C. for 15 min (previous experiments have demonstrated this to be the optimum time of heating, to reduce background interference from epidermal membrane, data not presented) and infected using 10 μL of *Gardnerella vaginalis* (approx 5×10$^7$ cfu) cell suspensions. Viable counts were performed to obtain the number of cell forming units after the preparation of the cell suspensions.

ChubTur® cells were set up, 3 mL of Ringers was added to the cells to ensure a humidity controlled environment.

After 24 h incubation at 35° C., 10 μL of test gel was applied onto the epidermal membrane surface.

Following incubation of the inoculated epidermal membrane, dosing was carried out by applying 2 μL of test gel to the epidermal membrane samples (n=3 for each gel and time point upon initiation; multiple time points are not measured from the same sample.

Following dosing, the samples were analyzed for the presence of ATP from viable organism after 4, 8 and 24 h.

Positive and negative controls were included. The negative controls comprised epidermal membrane samples with no organism or formulation added at t=0, and the positive controls comprised epidermal membrane samples with organism only (no formulations) added at t=0.

For the full scale study, the following changes were made to the protocol:

The initial infection of the epidermal membrane and the anaerobic incubation time before dosing was reduced to 30 min.

The exposure time to gels was reduced to 2 h to minimize the natural decrease in organism viability with time.

Efficacy of the gels was tested 2 h after application of gel onto epidermal membrane samples infected with *G. vaginalis* by removing the ChubTur® cells from incubation and performing ATP assay.

Results. Pilot Study. FIG. 9 shows the variation in ATP release (for a 10 application dose) from *Gardnerella vaginalis* infected EP samples, on application of exemplary active gel MG32PB (n=3, upon initiation) and its comparison with un-treated infected EP samples. Corresponding placebos, MG32PB-P, and controls were tested at n=2. The lower the amount of ATP recovered, the higher the efficacy of the test gel against the test organism.

From the data presented in FIG. 10, it is observed that the positive control (infected, untreated epidermal membrane) as expected, gives a high recovery of ATP while a lower amount of background interference is observed for the negative controls (un-infected, un-treated epidermal membrane). The dosing time with formulation also shows an effect on the ATP recovery. It is seen that following 24 hour dosing the levels of ATP reduces close to the background ATP (negative control) level. This phenomenon, although to a lesser extent, is also observed for the 8 hour time point. From this pilot study, it was determined that the initial incubation time (4, 8 and 24 hour) should be reduced in order to decrease the effect of natural cell death over time. The dosing time was reduced to 2 hour for the full scale study.

Results. Full Scale Study. FIG. 11 shows the variation in ATP release from *Gardnerella vaginalis* (ATCC 14018) infected epidermal membrane samples, on application of the test gels, (n=6, upon initiation for active test gels and n=3 for placebos) and their comparison with the commercial comparator, Metrogel®. Positive controls (*Gardnerella vaginalis* infected epidermal membrane samples without any treatment) and negative controls (epidermal membrane samples with no infection or treatment) were also included.

The data presented in FIG. 11 show that a reduction in ATP recovery is observed for the infected skin samples, treated with the active test gels when compared to the recovery of ATP from infected skin samples treated with the corresponding placebo gels. Formulation MG32PB showed a significant difference in terms of efficacy, with respect to the ATP levels recovered (data not shown) between the active and placebo. There was a significant difference (p<0.05) showing a larger reduction in ATP recovery for the active of MG32PB compared to the infected control, indicating good efficacy of the formulation.

Infected skin samples treated with exemplary test gel MG33PB showed significantly lower (p<0.05) ATP recovery for both the active and placebo compared to the infected control. The high efficacy of formulation MG33PB, placebo was surprising considering the main difference between this formulation and the other formulations is Polycarbophil AA-1, a bioadhesive polymer, an excipient, only present in MG33PB formulation.

Formulation MG35PB had little or no effect in reducing organism viability for the active when compared to the infected samples not previously treated with any formulations.

Formulations MG32PB-A, MG33PB-A and MG33PB-P, all indicated a comparable (P<0.05) level of activity against *Gardnerella vaginalis* on human epidermal membrane. However, Metrogel® was significantly (p<0.05) more efficacious when compared to MG32PB-P, MG35PB-A and MG35PB-P.

Summary. MG33PB-A and MG32PB-A were observed to have higher efficacy than other formulations. However, it was also surprisingly discovered that MG33PB-P (having no metronidazole) was just as effective as the MG33PB (1.3% metronidazole) against *Gardnerella vaginalis*.

Example 10: In Vitro Evaluation of Novel Metronidazole Formulations for Antimicrobial Efficacy Using a Disc Diffusion Zone of Inhibition Assay Introduction. A study was performed to determine the minimal amount of benzyl alcohol necessary to inhibit microbial growth. In the study, antimicrobial efficacy of three placebo and one active high dosage MTZ gels against *Gardnerella vaginalis* were tested a disc diffusion zone of inhibition assay.

The gels tested are provided in Table 44, below:

TABLE 44

Theoretical Compositions of Formulations for In Vitro Antimicrobial Efficacy

| | Composition (% w/w) | | | |
|---|---|---|---|---|
| | MG33PGP 0% BA | MG33PGP 1% BA | MG33PGP 2% BA | MG33PG 2% BA |
| Metronidazole | 0.00 | 0.00 | 0.00 | 1.30 |
| Deionized Water | 57.90 | 56.90 | 55.90 | 54.60 |
| Polycarbophil AA-1 | 2.00 | 2.00 | 2.00 | 2.00 |
| Methyl paraben | 0.08 | 0.08 | 0.08 | 0.08 |
| Propyl paraben | 0.02 | 0.02 | 0.02 | 0.02 |
| Benzyl alcohol | 0.00 | 1.00 | 2.00 | 2.00 |
| Propylene glycol | 15.00 | 15.00 | 15.00 | 15.00 |
| Polyethylene glycol 400 | 25.00 | 25.00 | 25.00 | 25.00 |
| Total | 100.00 | 100.00 | 100.00 | 100.00 |

"P" designates a placebo gel;
"BA" is benzyl alcohol

For the assay, 3 ml of a *Gardnerella vaginalis* suspension adjusted to approximately $1 \times 10^9$ cfu/ml was prepared. A 100 µl aliquot of the suspension was pipetted onto the surface of the pre-poured Columbia blood agar (CBA) plates and the suspension spread evenly over the surface of the agar with a sterile spreader. The agar plate was then left to dry under the laminar flow cabinet. The zone of inhibition assay was then carried out by applying 20 µl of the test gel to the surface of a ¼ antibiotic assay disc (n=6 for each gel, note; the disc does not contain any antibiotics) and allowed to air dry for a period of 1 min under the laminar flow cabinet. The disc was then inverted and placed onto the surface of the plate pre-seeded with *Gardnerella vaginalis* and incubated in anaerobic jars at 35° C. for 48 h. Conditions were maintained as anaerobic by the use of AnaeroGen™ gas packs. Following incubation, the zone of inhibition for all of the formulations was measured with calipers.

Results.

The results, shown in FIG. 12, indicate MG33PB is efficacious against *Gardnerella vaginalis* where zones of inhibition are observed on CBA plates (data not shown). No activity was seen with any of the placebos MG33PB placebo (0%, 1% and 2% BA) as indicated by no zones of inhibition observed on the plates compared to the active formulation.

Summary.

MG33PB is efficacious against *Gardnerella vaginalis* as compared to placebo gels that do not contain MTZ.

The disclosures of the patents, patent documents, articles, abstracts and other publications cited herein are incorporated herein by reference in their entireties as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An intravaginal aqueous based gel composition comprising:
   a) metronidazole in a concentration of about 1.3% to about 1.5% by weight of the aqueous based gel composition;
   b) about 1% to about 3% by weight of the aqueous based gel composition of one or more mucoadhesive gelling polymers;
   c) about 30% to about 60% of water by weight of the aqueous based gel composition; and
   d) a ternary solvent system in a concentration of about 30% to about 60% by weight of the aqueous based gel composition, wherein the ternary solvent system comprises:
      i) one or more lower aromatic alcohols selected from the group consisting of benzyl alcohol, 2-methylbenzyl alcohol, phenoxyethanol, and mixtures thereof;
      ii) one or more lower alkylene diols selected from the group consisting of ethane-1,2-diol (ethylene glycol), propane-1,2-diol (propylene glycol), and mixtures thereof; and
      iii) one or more polyoxyalkylenes selected from the group consisting of polyoxyethylene (polyethylene glycol), polyoxypropylene, (polypropylene glycol) and mixtures thereof;
   said aqueous based gel composition exhibiting a viscosity ranging from about 200,000 mPa·s to about 400,000 mPa·s, measured at 25° C. using the controlled shear rate method, a Bohlin CVO 100 rheometer and the rheometer settings of Table 11 and having an aqueous phase with a pH ranging from about 3.0 to about 5.0.

2. The gel composition of claim 1 wherein the one or more mucoadhesive gelling polymers are selected from the group consisting of hydroxyethylcellulose, a carbomer, a polycarbophil, and mixtures thereof.

3. A method of treating a subject with bacterial vaginosis, comprising applying intravaginally to the subject a single administration of the aqueous-based gel composition of claim 1.

4. A method of treating a subject with bacterial vaginosis, comprising administering intravaginally to the subject a single dose aqueous based metronidazole gel composition wherein the single dose aqueous based metronidazole gel composition is administered once a day for one, two or three days, and the single dose aqueous based metronidazole gel composition comprises:
   i) 60-70 mg of metronidazole in a concentration of about 1.3% to about 1.5% by weight of the aqueous based metronidazole gel composition;
   ii) about 30% to about 60% of water by weight of the single dose aqueous based metronidazole gel composition;
   iii) about 1% to about 3% by weight of the single dose aqueous based metronidazole gel composition of at least one mucoadhesive gelling polymer; and
   iv) about 30% to about 60% of a ternary solvent system by weight of the single dose aqueous based metronidazole gel composition, the ternary solvent system comprising:
      1) one or more lower aromatic alcohols selected from the group consisting of benzyl alcohol, 2-methylbenzyl alcohol, phenoxyethanol, and mixtures thereof;
      2) one or more lower alkylene diols selected from the group consisting of ethane-1,2-diol (ethylene glycol), propane-1,2-diol (propylene glycol), and mixtures thereof; and
      3) one or more polyoxyalkylenes selected from the group consisting of polyoxyethylene (polyethylene glycol), polyoxypropylene, (polypropylene glycol) and mixtures thereof;
   wherein the single dose aqueous based metronidazole gel exhibits:
      a) a pH ranging from about 3.0 to about 5.0; and
      b) a viscosity of about 200,000 mPa·s to about 400,000 mPa·s at 25° C. using a controlled shear rate ramp method, a Bohlin CVO 100 rheometer and the rheometer settings of Table 11.

5. The method of claim 4 wherein the one or more mucoadhesive gelling polymers are selected from the group consisting of hydroxyethylcellulose, a carbomer, a polycarbophil, and mixtures thereof.

6. The intravaginal aqueous based gel composition of claim 1 wherein the one or more lower aromatic alcohols comprises about 1% to about 5% of weight of the ternary solvent system.

7. The method of claim 4 wherein the one or more lower aromatic alcohols comprises about 1% to about 5% by weight of the ternary solvent system.

8. An intravaginal aqueous based gel composition comprising:
   a) metronidazole in a concentration of about 1.3% to about 1.5% by weight of the aqueous based gel composition;
   b) about 1% to about 3% by weight of the aqueous based gel composition of one or more mucoadhesive gelling polymers selected from the group consisting of hydroxyethylcellulose, a polycarbophil, and mixtures thereof;
   c) about 30% to about 60% of water by weight of the aqueous based gel composition; and
   d) a ternary solvent system in a concentration of about 30% to about 60% by weight of the aqueous based gel composition, wherein the ternary solvent system consists of:
      i) about 1.3% to about 2.5% by weight of the aqueous based gel composition of one or more lower aromatic alcohols selected from the group consisting of benzyl alcohol, 2-methylbenzyl alcohol, phenoxyethanol, and mixtures thereof;

ii) about 3% to about 20% by weight of the aqueous based gel composition of one or more lower alkylene diols selected from the group consisting of ethane-1,2-diol (ethylene glycol), propane-1,2-diol (propylene glycol), and mixtures thereof; and iii) about 10% to about 50% by weight of the aqueous based gel composition of one or more polyoxyalkylenes selected from the group consisting of polyoxyethylene (polyethylene glycol), polyoxypropylene, (polypropylene glycol) and mixtures thereof;

said aqueous based gel composition exhibiting a viscosity ranging from about 200,000 mPa·s to about 400,000 mPa·s, measured at 25° C. using a controlled shear rate method, a Bohlin CVO 100 rheometer and the rheometer settings of Table 11 and having an aqueous phase with a pH ranging from about 3.0 to about 5.0.

9. The intravaginal aqueous based gel composition of claim 8 wherein the one or more mucoadhesive gelling polymers is a polycarbophil and the ternary solvent system consists of:

i) about 1.3% to about 2.5% by weight of the aqueous based gel composition of benzyl alcohol;

ii) about 3% to about 20% by weight of the aqueous based gel composition of propylene glycol; and iii) about 10% to about 50% by weight of the aqueous based gel composition of polyethylene glycol.

\* \* \* \* \*